United States Patent
Kopec et al.

(10) Patent No.: US 10,407,479 B2
(45) Date of Patent: Sep. 10, 2019

(54) MUTANT FGF-21 PEPTIDE PEGYLATED CONJUGATES AND USES THEREOF

(71) Applicant: 89Bio Ltd., Herzliya (IL)

(72) Inventors: Karla K. Kopec, West Chester, PA (US); Patrick Mengyuan Liu, Rockville, MD (US)

(73) Assignee: 89bio Ltd., Herzliya (IL)

( * ) Notice: Subject to any disclaimer, the term of this patent is extended or adjusted under 35 U.S.C. 154(b) by 0 days.

(21) Appl. No.: 16/225,640

(22) Filed: Dec. 19, 2018

(65) Prior Publication Data

US 2019/0185533 A1 Jun. 20, 2019

Related U.S. Application Data

(63) Continuation of application No. PCT/IB2018/001112, filed on Sep. 4, 2018.

(60) Provisional application No. 62/553,970, filed on Sep. 4, 2017.

(51) Int. Cl.
| | | |
|---|---|---|
| *A61K 38/18* | (2006.01) | |
| *C07K 14/50* | (2006.01) | |
| *A61P 3/10* | (2006.01) | |
| *A61K 47/60* | (2017.01) | |

(52) U.S. Cl.
CPC .......... *C07K 14/50* (2013.01); *A61K 38/1825* (2013.01); *A61K 47/60* (2017.08); *A61P 3/10* (2018.01)

(58) Field of Classification Search
None
See application file for complete search history.

(56) References Cited

U.S. PATENT DOCUMENTS

| | | | | |
|---|---|---|---|---|
| 9,187,532 | B2* | 11/2015 | DeFrees | ................. C07K 1/047 |
| 9,200,049 | B2 | 12/2015 | DeFrees | |
| 9,631,004 | B2* | 4/2017 | Morin | .................... C07K 14/50 |
| 9,975,936 | B2* | 5/2018 | Cujec | .................... C07K 14/50 |
| 10,189,883 | B2* | 1/2019 | Morin | .................... C07K 14/50 |
| 2004/0082038 | A1 | 4/2004 | Lee et al. | |

OTHER PUBLICATIONS

Sanyal, Arun et al., "Pegbelfermin (BMS-986036), a PEGylated fibroblast growth factor 21 analogue, in patients with non-alcoholic steathohepatitis: a randomised, double-blind, placebo-controlled, phase 2a trial", www.thelancet.com; Dec. 13, 2018, pp. 1-13, http://dx.doi.org/10.1016/S0140-6736(18)31785-9.

Charles, Edgar D., et al., "Pegbelfermin (BMS-986036), PEGylated FGF21, in Patients with Obesity and Type 2 Diabetes: Results from a Randomized Phase 2 Study", www.obestityjournal.org, Obesity, vol. 27, No. 11, Jan. 2019, pp. 41-49.

Molecular Cell Biology—NCBI Bookshelf, "Protein Glycosylation in the ER and Golgi Complex", https://www.ncbi.nlm.nih.gov/books/NBK21744[Apr. 18, 2019 4:38:49 PM] (10 pages).

Xu, Jing, et al., Polyethylene Glycol Modified FGF21 Engineered to Maximize Potency and Minimize Vacuole Formation, Bioconjugate Chemistry, American Chemical Society, pubs.acs.org/bc (Apr. 16, 2013), 11 pages.

Camacho, Raul C., et al., "Pegylated Fgf21 rapidly normalizes insulin-stimulated glucose utilization in diet-induced insulin resistant mice", European Journal of Pharmacology 715 (2013) pp. 41-45.

Ye, Xianlong, et al., "Long-lasting hypaglycemic effect of modified FGF-21 analog with polyethylene glycol in type 1 diabetic mice and its systematic toxicity", European Journal of Pharmacology, 781 (2016) pp. 198-208.

Huang, Zhifeng, et al., "A Better Anti-Diabetic Recombinant Human Fibroblast Growth Factor 21 (rhFGF21) Modified with Polyethylene Glycol", PLos ONE, Jun. 2011, vol. 6, Issue 6, e20669, www.plosone.org, pp. 1-13.

* cited by examiner

*Primary Examiner* — Christine J Saoud

(74) *Attorney, Agent, or Firm* — Greenberg Traurig, LLP

(57) ABSTRACT

The present invention relates to a mutant Fibroblast Growth Factor-21 (FGF-21) peptide conjugate comprising a PEG moiety attached to a mutant FGF-21 peptide via a glycosyl linker and uses thereof. Further provided is a method for producing the mutant FGF-21 peptide conjugate and a pharmaceutical composition and container comprising said mutant FGF-21 peptide conjugate.

27 Claims, 21 Drawing Sheets

Specification includes a Sequence Listing.

Fig. 2

| Sequence motif | Overall isolated yield (mg/L) |
|---|---|
| Wild-type | 16 |
| P$^5$TSSP | 29.8 |
| P$^5$TQAP | 11.1 |
| P$^3$TP | 18.6 |
| M$^1$FPTP | 20.4 |
| P$^{120}$TINT | 38 |
| P$^{120}$TSVG | 20 |
| P$^{120}$TET | 23.2 |
| P$^{125}$TQA | 33.1 |
| P$^{125}$TEI | 26.24 |
| P$^{129}$TP | 28.8 |
| P$^{139}$TP | 35.9 |
| P$^{148}$TP | 42 |
| P$^{151}$TINT | 15.8 |
| P$^{151}$TTVS | 70 |
| P$^{156}$TP | 19.8 |
| P$^{159}$TVG | 46.5 |
| P$^{159}$TINT | 20.8 |
| TETP$^{166}$ | 27.6 |
| P$^{166}$TSMV | 46 |
| P$^{166}$TSVG | 18.24 |
| P$^{166}$TQGAM | 24.8 |
| P$^{172}$TQGAS | 25.9 |
| P$^{172}$TQGAM | 52.6 |
| P$^{178}$TQ | 13.6 |
| P$^{178}$TINT | 32.8 |

Non-Reducing SDS-PAGE of Mutant FGF-21 Peptide Conjugate Samples Stored for 1 Week at (2-8) °C and 40 °C Concentration of sub-visible particles ≥ 10 μm as a function of Polysorbate 20 concentration.

*p<0.05, ***p<0.001 vs. vehicle (anova 1-way + Dunnett's post-test)
££p<0.01, £££p<0.001 vs. vehicle (Kruskal-Wallis + Dunns post-test)

- NaCl 0.9%
- TEV- 47948, 20µg/kg
- TEV- 47948, 100µg/kg
- TEV- 47948, 500µg/kg
- obeticholic acid + NaCl 0.9%

*p<0.05, p<0.01, *p<0.001 vs. vehicle

*p<0.05, ***p<0.001 vs. vehicle

*p<0.05, p<0.01, *p<0.001 vs. vehicle

***p<0.001 vs. vehicle

SEQUENCE LISTING

```
<160> NUMBER OF SEQ ID NOS: 30

<210> SEQ ID NO 1
<211> LENGTH: 182
<212> TYPE: PRT
<213> ORGANISM: Homo sapiens

<400> SEQUENCE: 1

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 2
```

```
<211> LENGTH: 182
<212> TYPE: PRT
<213> ORGANISM: Artificial
<220> FEATURE:
<223> OTHER INFORMATION: mutant

<400> SEQUENCE: 2
```

| Met | His | Pro | Ile | Pro | Asp | Ser | Ser | Pro | Leu | Leu | Gln | Phe | Gly | Gly | Gln |
|---|---|---|---|---|---|---|---|---|---|---|---|---|---|---|---|
| 1 | | | | 5 | | | | | 10 | | | | | 15 | |

| Val | Arg | Gln | Arg | Tyr | Leu | Tyr | Thr | Asp | Asp | Ala | Gln | Gln | Thr | Glu | Ala |
|---|---|---|---|---|---|---|---|---|---|---|---|---|---|---|---|
| | | | 20 | | | | | 25 | | | | | 30 | | |

| His | Leu | Glu | Ile | Arg | Glu | Asp | Gly | Thr | Val | Gly | Gly | Ala | Ala | Asp | Gln |
|---|---|---|---|---|---|---|---|---|---|---|---|---|---|---|---|
| | | | 35 | | | | | 40 | | | | | 45 | | |

| Ser | Pro | Glu | Ser | Leu | Leu | Gln | Leu | Lys | Ala | Leu | Lys | Pro | Gly | Val | Ile |
|---|---|---|---|---|---|---|---|---|---|---|---|---|---|---|---|
| | 50 | | | | | 55 | | | | | 60 | | | | |

| Gln | Ile | Leu | Gly | Val | Lys | Thr | Ser | Arg | Phe | Leu | Cys | Gln | Arg | Pro | Asp |
|---|---|---|---|---|---|---|---|---|---|---|---|---|---|---|---|
| 65 | | | | | 70 | | | | | 75 | | | | | 80 |

| Gly | Ala | Leu | Tyr | Gly | Ser | Leu | His | Phe | Asp | Pro | Glu | Ala | Cys | Ser | Phe |
|---|---|---|---|---|---|---|---|---|---|---|---|---|---|---|---|
| | | | | 85 | | | | | 90 | | | | | 95 | |

| Arg | Glu | Leu | Leu | Leu | Glu | Asp | Gly | Tyr | Asn | Val | Tyr | Gln | Ser | Glu | Ala |
|---|---|---|---|---|---|---|---|---|---|---|---|---|---|---|---|
| | | | | 100 | | | | | 105 | | | | | 110 | |

| His | Gly | Leu | Pro | Leu | His | Leu | Pro | Gly | Asn | Lys | Ser | Pro | His | Arg | Asp |
|---|---|---|---|---|---|---|---|---|---|---|---|---|---|---|---|
| | | | | 115 | | | | | 120 | | | | | 125 | |

| Pro | Ala | Pro | Arg | Gly | Pro | Ala | Arg | Phe | Leu | Pro | Leu | Pro | Gly | Leu | Pro |
|---|---|---|---|---|---|---|---|---|---|---|---|---|---|---|---|
| | 130 | | | | | 135 | | | | | 140 | | | | |

| Pro | Ala | Leu | Pro | Glu | Pro | Pro | Gly | Ile | Leu | Ala | Pro | Gln | Pro | Pro | Asp |
|---|---|---|---|---|---|---|---|---|---|---|---|---|---|---|---|
| 145 | | | | | 150 | | | | | 155 | | | | | 160 |

| Val | Gly | Ser | Ser | Asp | Pro | Leu | Ser | Met | Val | Gly | Pro | Thr | Gln | Gly | Ala |
|---|---|---|---|---|---|---|---|---|---|---|---|---|---|---|---|
| | | | | 165 | | | | | 170 | | | | | 175 | |

| Ser | Pro | Ser | Tyr | Ala | Ser |
|---|---|---|---|---|---|
| | | | 180 | | |

```
<210> SEQ ID NO 3
<211> LENGTH: 182
<212> TYPE: PRT
<213> ORGANISM: Artificial
<220> FEATURE:
<223> OTHER INFORMATION: mutant

<400> SEQUENCE: 3
```

| Met | His | Pro | Ile | Pro | Asp | Ser | Ser | Pro | Leu | Leu | Gln | Phe | Gly | Gly | Gln |
|---|---|---|---|---|---|---|---|---|---|---|---|---|---|---|---|
| 1 | | | | 5 | | | | | 10 | | | | | 15 | |

| Val | Arg | Gln | Arg | Tyr | Leu | Tyr | Thr | Asp | Asp | Ala | Gln | Gln | Thr | Glu | Ala |
|---|---|---|---|---|---|---|---|---|---|---|---|---|---|---|---|
| | | | 20 | | | | | 25 | | | | | 30 | | |

| His | Leu | Glu | Ile | Arg | Glu | Asp | Gly | Thr | Val | Gly | Gly | Ala | Ala | Asp | Gln |
|---|---|---|---|---|---|---|---|---|---|---|---|---|---|---|---|
| | | | 35 | | | | | 40 | | | | | 45 | | |

| Ser | Pro | Glu | Ser | Leu | Leu | Gln | Leu | Lys | Ala | Leu | Lys | Pro | Gly | Val | Ile |
|---|---|---|---|---|---|---|---|---|---|---|---|---|---|---|---|
| | 50 | | | | | 55 | | | | | 60 | | | | |

| Gln | Ile | Leu | Gly | Val | Lys | Thr | Ser | Arg | Phe | Leu | Cys | Gln | Arg | Pro | Asp |
|---|---|---|---|---|---|---|---|---|---|---|---|---|---|---|---|
| 65 | | | | | 70 | | | | | 75 | | | | | 80 |

| Gly | Ala | Leu | Tyr | Gly | Ser | Leu | His | Phe | Asp | Pro | Glu | Ala | Cys | Ser | Phe |
|---|---|---|---|---|---|---|---|---|---|---|---|---|---|---|---|
| | | | | 85 | | | | | 90 | | | | | 95 | |

| Arg | Glu | Leu | Leu | Leu | Glu | Asp | Gly | Tyr | Asn | Val | Tyr | Gln | Ser | Glu | Ala |
|---|---|---|---|---|---|---|---|---|---|---|---|---|---|---|---|
| | | | | 100 | | | | | 105 | | | | | 110 | |

| His | Gly | Leu | Pro | Leu | His | Leu | Pro | Gly | Asn | Lys | Ser | Pro | His | Arg | Asp |
|---|---|---|---|---|---|---|---|---|---|---|---|---|---|---|---|
| | | | | 115 | | | | | 120 | | | | | 125 | |

| Pro | Ala | Pro | Arg | Gly | Pro | Ala | Arg | Phe | Leu | Pro | Leu | Pro | Gly | Leu | Pro |
|---|---|---|---|---|---|---|---|---|---|---|---|---|---|---|---|

```
                130                 135                 140
Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Thr Gln Gly Ala
                165                 170                 175

Met Pro Ser Tyr Ala Ser
            180
```

<210> SEQ ID NO 4
<211> LENGTH: 182
<212> TYPE: PRT
<213> ORGANISM: Artificial
<220> FEATURE:
<223> OTHER INFORMATION: mutant

<400> SEQUENCE: 4

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Thr Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 5
<211> LENGTH: 182
<212> TYPE: PRT
<213> ORGANISM: Artificial
<220> FEATURE:
<223> OTHER INFORMATION: mutant

<400> SEQUENCE: 5

```
Met His Pro Ile Pro Thr Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 6
<211> LENGTH: 182
<212> TYPE: PRT
<213> ORGANISM: Artificial
<220> FEATURE:
<223> OTHER INFORMATION: mutant

<400> SEQUENCE: 6

```
Met His Pro Thr Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
         50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 7
<211> LENGTH: 182
<212> TYPE: PRT
<213> ORGANISM: Artificial
<220> FEATURE:
<223> OTHER INFORMATION: mutant

<400> SEQUENCE: 7

Met His Pro Ile Pro Asp Ser Ser Pro Thr Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 8
<211> LENGTH: 182
<212> TYPE: PRT
<213> ORGANISM: Artificial
<220> FEATURE:
<223> OTHER INFORMATION: mutant

<400> SEQUENCE: 8

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Thr Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

```
Ser Pro Ser Tyr Ala Ser
            180

<210> SEQ ID NO 9
<211> LENGTH: 182
<212> TYPE: PRT
<213> ORGANISM: Artificial
<220> FEATURE:
<223> OTHER INFORMATION: mutant

<400> SEQUENCE: 9

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Thr Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 10
<211> LENGTH: 182
<212> TYPE: PRT
<213> ORGANISM: Artificial
<220> FEATURE:
<223> OTHER INFORMATION: mutant

<400> SEQUENCE: 10

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Thr
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
```

```
                      100                 105                 110
His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 11
<211> LENGTH: 182
<212> TYPE: PRT
<213> ORGANISM: Artificial
<220> FEATURE:
<223> OTHER INFORMATION: mutant

<400> SEQUENCE: 11

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Thr Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 12
<211> LENGTH: 182
<212> TYPE: PRT
<213> ORGANISM: Artificial
<220> FEATURE:
<223> OTHER INFORMATION: mutant

<400> SEQUENCE: 12

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Thr His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 13
<211> LENGTH: 182
<212> TYPE: PRT
<213> ORGANISM: Artificial
<220> FEATURE:
<223> OTHER INFORMATION: mutant

<400> SEQUENCE: 13

Met His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Thr Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 14
<211> LENGTH: 182

```
<212> TYPE: PRT
<213> ORGANISM: Artificial
<220> FEATURE:
<223> OTHER INFORMATION: mutant

<400> SEQUENCE: 14

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro Thr Arg Asp
        115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 15
<211> LENGTH: 182
<212> TYPE: PRT
<213> ORGANISM: Artificial
<220> FEATURE:
<223> OTHER INFORMATION: mutant

<400> SEQUENCE: 15

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Thr Pro Arg Gly Pro Ala Arg Phe Leu Pro Leu Pro Gly Leu Pro
130                 135                 140
```

```
Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 16
<211> LENGTH: 182
<212> TYPE: PRT
<213> ORGANISM: Artificial
<220> FEATURE:
<223> OTHER INFORMATION: mutant

<400> SEQUENCE: 16

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Thr Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
            165                 170                 175

Ser Pro Ser Tyr Ala Ser
            180

<210> SEQ ID NO 17
<211> LENGTH: 182
<212> TYPE: PRT
<213> ORGANISM: Artificial
<220> FEATURE:
<223> OTHER INFORMATION: mutant

<400> SEQUENCE: 17

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
```

```
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Thr Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 18
<211> LENGTH: 182
<212> TYPE: PRT
<213> ORGANISM: Artificial
<220> FEATURE:
<223> OTHER INFORMATION: mutant

<400> SEQUENCE: 18

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Thr Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 19
<211> LENGTH: 182
<212> TYPE: PRT
<213> ORGANISM: Artificial
<220> FEATURE:
<223> OTHER INFORMATION: mutant

<400> SEQUENCE: 19
```

```
Met His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
             20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Thr Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 20
<211> LENGTH: 183
<212> TYPE: PRT
<213> ORGANISM: Artificial
<220> FEATURE:
<223> OTHER INFORMATION: mutant

<400> SEQUENCE: 20

Met His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
             20                  25                  30

His Leu Glu Ile Arg Glu Asp Gly Thr Val Gly Gly Ala Ala Asp Gln
         35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Thr Pro Ala Leu Pro Glu Pro Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175
```

Arg Ser Pro Ser Tyr Ala Ser
            180

<210> SEQ ID NO 21
<211> LENGTH: 182
<212> TYPE: PRT
<213> ORGANISM: Artificial
<220> FEATURE:
<223> OTHER INFORMATION: mutant

<400> SEQUENCE: 21

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Thr Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 22
<211> LENGTH: 182
<212> TYPE: PRT
<213> ORGANISM: Artificial
<220> FEATURE:
<223> OTHER INFORMATION: mutant

<400> SEQUENCE: 22

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Thr Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 23
<211> LENGTH: 183
<212> TYPE: PRT
<213> ORGANISM: Artificial
<220> FEATURE:
<223> OTHER INFORMATION: mutant

<400> SEQUENCE: 23

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Thr Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
        180

<210> SEQ ID NO 24
<211> LENGTH: 182
<212> TYPE: PRT
<213> ORGANISM: Artificial
<220> FEATURE:
<223> OTHER INFORMATION: mutant

<400> SEQUENCE: 24

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln

```
                35                  40                  45
Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
130                 135                 140

Pro Ala Leu Pro Glu Pro Pro Thr Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 25
<211> LENGTH: 183
<212> TYPE: PRT
<213> ORGANISM: Artificial
<220> FEATURE:
<223> OTHER INFORMATION: mutant

<400> SEQUENCE: 25

Met His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
                 35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
                115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Thr Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
                180

<210> SEQ ID NO 26
<211> LENGTH: 182
<212> TYPE: PRT
```

```
<213> ORGANISM: Artificial
<220> FEATURE:
<223> OTHER INFORMATION: mutant

<400> SEQUENCE: 26

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Thr
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 27
<211> LENGTH: 182
<212> TYPE: PRT
<213> ORGANISM: Artificial
<220> FEATURE:
<223> OTHER INFORMATION: mutant

<400> SEQUENCE: 27

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140
```

```
Pro Ala Leu Pro Glu Pro Gly Ile Leu Ala Pro Gln Pro Pro Asp
145                 150                 155                 160

Val Gly Ser Ser Asp Pro Thr Ser Met Val Gly Pro Ser Gln Gly Arg
                165                 170                 175

Ser Pro Ser Tyr Ala Ser
            180
```

<210> SEQ ID NO 28
<211> LENGTH: 182
<212> TYPE: PRT
<213> ORGANISM: Artificial
<220> FEATURE:
<223> OTHER INFORMATION: mutant

<400> SEQUENCE: 28

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Thr Tyr Ala Ser
            180
```

<210> SEQ ID NO 29
<211> LENGTH: 28
<212> TYPE: DNA
<213> ORGANISM: Artificial Sequence
<220> FEATURE:
<223> OTHER INFORMATION: PCR Primer

<400> SEQUENCE: 29
gaggtcatat gcatccaatt ccagattc          28

<210> SEQ ID NO 30
<211> LENGTH: 26
<212> TYPE: DNA
<213> ORGANISM: Artificial Sequence
<220> FEATURE:
<223> OTHER INFORMATION: PCR Primer

<400> SEQUENCE: 30
attcctcgag ttattaagag gcgtag            26

MUTANT FGF-21 PEPTIDE PEGYLATED CONJUGATES AND USES THEREOF

RELATED APPLICATIONS

This application is a continuation of International PCT Application No. PCT/IB2018/00112, filed Sep. 4, 2018, which claims priority of U.S. Provisional Application No. 62/553,970, filed Sep. 4, 2017, the entirety of which are incorporated herein by reference for all purposes.

FIELD OF THE INVENTION

The present invention relates to a mutant Fibroblast Growth Factor-21 (FGF-21) peptide conjugate comprising a polyethylene glycol (PEG) moiety attached to a mutant FGF-21 peptide via a glycosyl moiety and therapeutic uses thereof. A method for producing the mutant FGF-21 peptide conjugate and a pharmaceutical composition and container comprising the mutant FGF-21 peptide conjugate are also encompassed herein.

BACKGROUND OF THE INVENTION

FGF-21 is an endocrine hormone that is naturally found as a monomeric non-glycosylated protein. Together with FGF-19 and FGF-23, FGF-21 belongs to the endocrine-acting sub-family while the remaining of the 18 mammalian FGF ligands are grouped into five paracrine-acting sub-families. Endocrine-acting FGFs, in contrast to paracrine-acting FGFs, exhibit only low affinity for heparin-sulfate and are thus able to enter the blood circulation. Thereby, endocrine FGFs are able to regulate metabolic processes, such as bile acid homeostasis, hepatic glucose and protein metabolism (FGF-19), glucose and lipid metabolism (FGF-21) and vitamin D and phosphate homeostasis (FGF-23).

SUMMARY OF THE INVENTION

Mutant FGF-21 peptide conjugates having surprising properties are described herein. Also described herein are pharmaceutical compositions comprising at least one of the mutant FGF-21 peptide conjugates described herein and pharmaceutical containers comprising same. More particularly, a mutant Fibroblast Growth Factor-21 (FGF-21) peptide conjugate comprising a mutant FGF-21 peptide comprising at least one threonine residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and a 20 kDa polyethylene glycol (PEG), wherein the 20 kDa PEG is covalently attached to the mutant FGF-21 peptide at the at least one threonine residue via a glycosyl moiety. Further provided are a method for producing the mutant FGF-21 peptide conjugate and uses thereof in the treatment of at least one of diabetes and related diseases, particularly diabetes type 2, non-alcoholic steatohepatitis (NASH) or metabolic syndrome. In a more particular embodiment, the diabetes type 2, NASH, or metabolic syndrome are treated in a human subject. Also provided is a method for treating diabetes and related diseases in a subject in need of such treatment, particularly diabetes type 2, NASH and/or metabolic syndrome, and more particularly diabetes type 2, NASH, and/or metabolic syndrome in a human subject. Also encompassed herein is the mutant FGF-21 peptide conjugate for use in treating diabetes type 2, NASH and/or metabolic syndrome, and more particularly diabetes type 2, NASH, and/or metabolic syndrome in a human subject. In another aspect, the mutant FGF-21 peptide conjugate is used in the preparation of a medicament for the treatment of diabetes type 2, NASH and/or metabolic syndrome, and more particularly diabetes type 2, NASH, and/or metabolic syndrome in a human subject.

In contrast to the general teachings in the art, the present inventors surprisingly found that PEGylation close to the C-terminus is tolerated and protein conjugates comprising same are biologically active in vitro and in vivo. It was also noted that attachment of a 20 kDa PEG residue to a mutant FGF-21 peptide generated a mutant FGF-21 peptide conjugate having surprising therapeutic properties as demonstrated in a variety of in vitro and in vivo assays. Such surprising properties include an improved half-life, which is estimated to be ~80 hours in humans, and the ability to reduce at least one of HbA1c (a stable indicator of glycemic index), serum triglyceride levels, or serum insulin levels in a subject in need thereof. Such subjects include, without limitation, a subject who is suspected of having diabetes and/or a related disease/s (e.g., diabetes type 2, NASH, and/or metabolic syndrome) or who has diabetes and/or a related disease/s (e.g., diabetes type 2, NASH, and/or metabolic syndrome). Mutant FGF-21 peptide conjugates comprising a 20 kDa PEG residue also exhibit high bioavailability as reflected by 38% bioavailability in mice and rats, and 56% bioavailability in monkeys.

In an aspect, a mutant Fibroblast Growth Factor-21 (FGF-21) peptide conjugate is described herein comprising
  i) a mutant FGF-21 peptide comprising the amino acid sequence of SEQ ID NO: 2,
  ii) a glycosyl moiety, and
  iii) a 20 kDa polyethylene glycol (PEG),
  wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG. In a particular embodiment thereof, the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof. In another particular embodiment, the glycosyl moiety comprises at least one of an N-acetylgalactosamine (GalNAc) residue, a galactose (Gal) residue, a sialic acid (Sia), or a combination thereof. In a more particular embodiment thereof, the at least one Sia residue is a nine-carbon carboxylated sugar. Still more particularly, the at least one Sia residue is N-acetyl-neuraminic acid (2-keto-5-acetamido-3,5-dideoxy-D-glycero-D-galacto-nonulopyranos-1-onic acid (Neu5Ac), N-glycolylneuraminic acid (Neu5Gc), 2-keto-3-deoxy-nonulosonic acid (KDN), or a 9-substituted sialic acid. In a more particular embodiment, the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac. In an even more particular embodiment, the glycosyl moiety comprises the structure -GalNAc-Sia-.

In an aspect, the mutant FGF-21 peptide conjugate described herein comprising the 20 kDa PEG moiety is attached to the glycosyl moiety by a covalent bond to a linker, wherein the linker comprises at least one amino acid residue. Exemplary amino acids, include: polar, but neutral amino acids (e.g., serine, threonine, cysteine, tyrosine, asparagine, and glutamine) and non-polar amino acids with relatively simple side chains (e.g. glycine, alanine, valine, leucine). In a particular embodiment, the at least one amino acid residue is at least one glycine (Gly). In a still more particular embodiment, the mutant FGF-21 peptide conjugate comprises the structure -GalNAc-Sia-Gly-PEG (20 kDa).

In an even more particular embodiment, the mutant FGF-21 peptide conjugate comprises the structure:

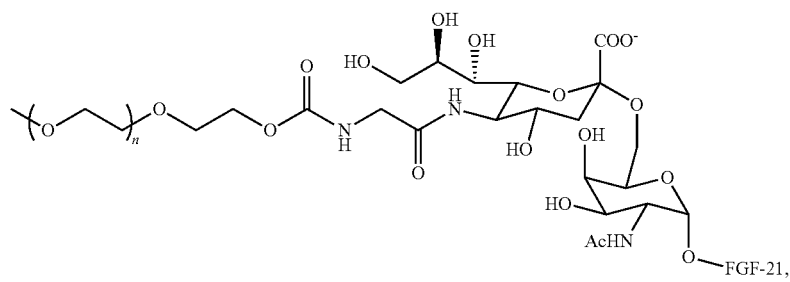

wherein n is an integer selected from 450 to 460.

A mutant FGF-21 peptide conjugate described herein may comprise a 20 kDa PEG which is a linear or branched PEG. In a more particular embodiment, the 20 kDa PEG is a linear PEG. In a still more particular embodiment, the 20 kDa PEG is a 20 kDa methoxy-PEG.

In another aspect, a pharmaceutical composition comprising any one of or at least one of the mutant FGF-21 peptide conjugates described herein and a pharmaceutically acceptable carrier is presented. The mutant FGF-21 peptide conjugate may be present in the pharmaceutical composition in a concentration in a range from 0.1 mg/mL to 50 mg/mL, particularly from 1 mg/mL to 45 mg/mL, more particularly from 10 mg/mL to 40 mg/mL, most particularly in a concentration of 26±4 mg/mL. In a particular embodiment, the pharmaceutical composition further comprises a buffering agent, particularly a Tris buffer. In another embodiment, the buffering agent is present in a concentration from 1 mM to 100 mM, particularly from 2 mM to 75 mM, more particularly from 5 mM to 50 mM, even more particularly from 10 mM to 25 mM, most particularly of 16±2 mM. More particularly, the pH is in the range from 6.0 to 8.5, particularly from 6.5 to 8.0, more particularly from 6.75 to 8.0, and most particularly is 7.5±0.3. In another particular embodiment, the pharmaceutical composition further comprises a salt, particularly an inorganic salt, more particularly NaCl. More particularly, the salt is present in a concentration from 30 mM to 200 mM, particularly from 40 mM to 150 mM, more particularly from 50 mM to 100 mM, most particularly of 56±2 mM. The pharmaceutical composition may further comprise a tonicity modifying agent. Such tonicity modifying agents include, without limitation, glycerol, amino acids, sodium chloride, proteins, sugars and sugar alcohols, particularly the tonicity modifying agent is a sugar, more particularly the tonicity modifying agent is sucrose. In another embodiment, the the tonicity modifying agent is present in a concentration of 50 mM to 200 mM, more particularly in a concentration of 100 mM to 175 mM, even more particularly is present in a concentration of 135 mM to 160 mM, and most particularly in a concentration of 150±2 mM. In another embodiment, the pharmaceutical composition further comprises a surfactant, particularly a non-ionic surfactant, wherein the surfactant or non-ionic surfactant is a polysorbate-based non-ionic surfactant, particularly polysorbate 20 or polysorbate 80, more particularly polysorbate 20. In a particular embodiment, the surfactant or non-ionic surfactant is present in a concentration of 0.01 mg/mL to 1 mg/mL, particularly in a concentration of 0.05 to 0.5 mg/mL and more particularly in a concentration of 0.2±0.02 mg/mL.

In an exemplary embodiment, the pharmaceutical composition comprises 0.1 mg/mL to 50 mg/mL of mutant FGF-21 peptide conjugate, 1 mM to 100 mM buffering agent, particularly Tris buffer, 30 mM to 200 mM mM salt, particularly NaCl, 50 mM to 200 mM tonicity modifying agent, particularly sucrose, and 0.01 mg/mL to 1 mg/mL surfactant or non-ionic surfactant, particularly polysorbate 20, and has a pH of 6.0 to 8.5.

Also encompassed herein is a pharmaceutical container comprising any one of or at least one of a mutant FGF-21 peptide conjugate described herein or a pharmaceutical composition comprising same. Exemplary such pharmaceutical containers include, without limitation, a syringe, vial, infusion bottle, ampoule, carpoule, a syringe equipped with a needle protection system, or a carpoule within an injection pen.

In a further aspect, a method of producing a mutant FGF-21 peptide conjugate described herein is presented, comprising the steps of:

(1) recombinantly producing the mutant FGF-21 peptide in an expression host; and (2) enzymatically attaching to the mutant FGF-21 peptide of step (1) a PEG-glycosyl moiety, wherein the PEG has 20 kDa, thereby forming the mutant FGF-21 peptide conjugate. In a particular embodiment, the expression host is *Escherichia coli*. In another particular embodiment of the method, step (2) comprises a step (2a) of contacting the mutant FGF-21 peptide with a GalNAc donor and a GalNAc transferase under conditions suitable to transfer GalNAc from the GalNAc donor to the threonine at amino acid position 173 of SEQ ID NO: 2. In a still more particular embodiment, the GalNAc donor is UDP-GalNAc. In yet another particular embodiment, the GalNAc transferase is MBP-GalNAcT2. In another particular embodiment of the method, step (2) further comprises a step (2b) of contacting the product of step (1) or of step (2a), if present, with a 20 kDa PEG-Sia donor and a sialyl-transferase under conditions suitable to transfer 20 kDa PEG-Sia from the 20 kDa PEG-Sia donor to the threonine residue at amino acid position 173 of SEQ ID NO: 2 or to the GalNAc attached to the threonine residue at amino acid position 173 of SEQ ID NO: 2 if step (2a) is present. In a further particular embodiment of the method, the 20 kDa PEG-Sia donor is 20 kDa PEG-Sia-CMP. In a still more particular embodiment of the method, the sialyltransferase is ST6GalNAc1. In an even more particular embodiment of the method, the 20 kDa PEG-Sia donor comprises the structure

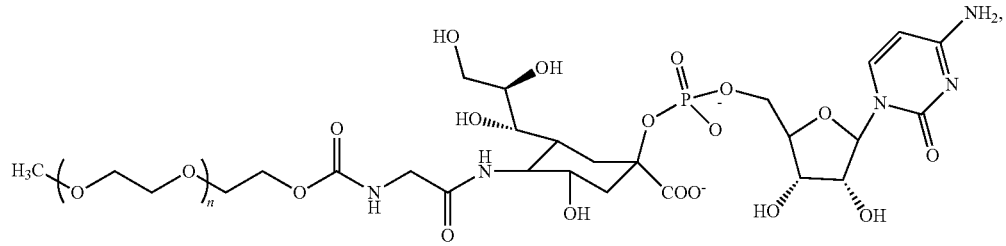

wherein n is an integer selected from 450 to 460.

In another particular embodiment of the method, the method further comprises a step (3), after step (1) and prior to step (2), of purifying the mutant FGF-21 peptide after recombinant production. The method may further comprise a step (4), after step (2), of purifying the mutant FGF-21 peptide conjugate formed in step (2). In a particular embodiment, step (3) comprises subjecting the mutant FGF-21 peptide and/or step (4) comprises subjecting the mutant FGF-21 peptide conjugate to a method selected from the group consisting of ion exchange chromatography, affinity chromatography, filtration and combinations thereof. The step of purifying may comprise one or more steps of ion exchange chromatography, particularly two steps of ion exchange chromatography. In a particular embodiment thereof, the ion exchange chromatography is an anion exchange chromatography, particularly a strong anion exchange chromatography. In a particular embodiment thereof, the anion exchange chromatography employs a member selected from the group consisting of a hydrophilic polyvinyl ether base matrix, polystyrene/divinyl benzene polymer matrix, trimethylammoniumethyl (TEAE), diethylaminoethanol (DEAE), agarose, a quaternary ammonium (Q) strong anion exchange chromatography and combinations thereof. In another particular embodiment thereof, step (3) comprises two anion exchange chromatography steps using a hydrophilic polyvinyl ether base matrix. In another particular embodiment thereof, step (4) comprises two quaternary ammonium (Q) strong anion exchange chromatography steps. In particular embodiment, arginine is added in step (2) and/or, if present, in step (3), particularly at least 400 mM arginine. In another particular embodiment, the method further comprises a step (5), after step (3) and prior to step (2), of endotoxin removal, wherein the product of step (3) is filtered using an endotoxin removal filter.

Also encompassed herein is a mutant FGF-21 peptide conjugate obtainable by any one of the methods described herein.

In another aspect, a method for treating diabetes or a diabetes related disease is presented, comprising administering to a subject in need thereof an amount of a mutant FGF-21 peptide conjugate described herein or obtainable by a method described herein or a pharmaceutical composition comprising same. The diabetes or the diabetes related disease may comprise at least one of diabetes type 2, non-alcoholic steatohepatitis (NASH), or metabolic syndrome.

In a particular embodiment, the subject is a human subject. In a more particular embodiment, the administering reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein.

Also encompassed herein is any one of the mutant FGF-21 peptide conjugates described herein or a pharmaceutical composition comprising same for use in a method for treating diabetes or a diabetes related disease. The diabetes or the diabetes related disease may comprise at least one of diabetes type 2, non-alcoholic steatohepatitis (NASH), or metabolic syndrome. In a particular embodiment, the diabetes or the diabetes related disease afflicts a human subject. In a more particular embodiment, the use reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein.

In another aspect, use of a mutant FGF-21 peptide conjugate described herein in the preparation of a medicament for use in a method for treating diabetes or a diabetes related disease is presented. The diabetes or the diabetes related disease may comprise at least one of diabetes type 2, non-alcoholic steatohepatitis (NASH), or metabolic syndrome. In a particular embodiment, the diabetes or the diabetes related disease afflicts a human subject. In a more particular embodiment, the use reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein.

In another aspect, a mutant Fibroblast Growth Factor-21 (FGF-21) peptide conjugate is presented comprising
i) a mutant FGF-21 peptide comprising the amino acid sequence of SEQ ID NO: 2,
ii) a glycosyl moiety, wherein the glycosyl moiety comprises the structure -GalNAc-Sia-, and
iii) a 30 kDa polyethylene glycol (PEG),
wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 30 kDa PEG by a covalent bond between a second site of the glycosyl moiety and the 30 kDa PEG. In a particular embodiment, the 30 kDa PEG moiety is attached to the glycosyl moiety by a covalent bond to a linker, wherein the linker comprises at least one amino acid residue. Exemplary amino acids, include: polar, but neutral amino acids (e.g., serine, threonine, cysteine, tyrosine, asparagine, and glutamine) and non-polar amino acids with relatively simple side chains (e.g. glycine, alanine, valine, leucine). In a particular embodiment, the at least one amino acid residue is at least one glycine (Gly). In a still more particular embodiment, the mutant FGF-21 peptide conjugate comprises the structure -GalNAc-Sia-Gly-PEG (30 kDa). A mutant FGF-21 peptide conjugate described herein may comprise a 30 kDa PEG which is a linear or branched PEG. In a more particular embodiment, the 30 kDa PEG is a linear PEG. In a still more particular embodiment, the 30 kDa PEG is a 30 kDa methoxy-PEG.

BRIEF DESCRIPTION OF THE DRAWINGS

FIG. 2: Overall isolated yield after purification and formulation of exemplary wild-type/native FGF-21 and mutants given in mg protein FGF-21 per Liter of fermentate-shake flask.

| Sample | Composition |
|---|---|
| 'pH 5' sample | 2 mg/mL gPEG-FGF21, 20 mM acetate, 125 mM NaCl, pH 5.0 |
| 'pH 6' sample | 2 mg/mL gPEG-FGF21, 20 mM histidine, 125 mM NaCl, pH 6.0 |
| 'pH 7' sample | 2 mg/mL gPEG-FGF21, 20 mM phosphate, 125 mM NaCl, pH 7.0 |

As can be seen from the gel image that samples having a pH of 7 contain the fewest aggregates (bands at higher molecular weight) and other degradation products (bands at lower molecular weight) when compared to samples having a pH of 5 or 6.

Figure 7:
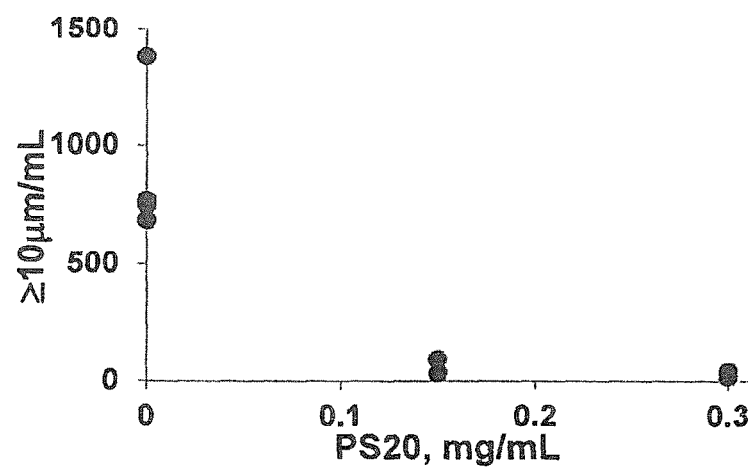

FIG. 7: Concentration of sub-visible particles 10 μm as a function of Polysorbate 20 concentration.

Figure 8:
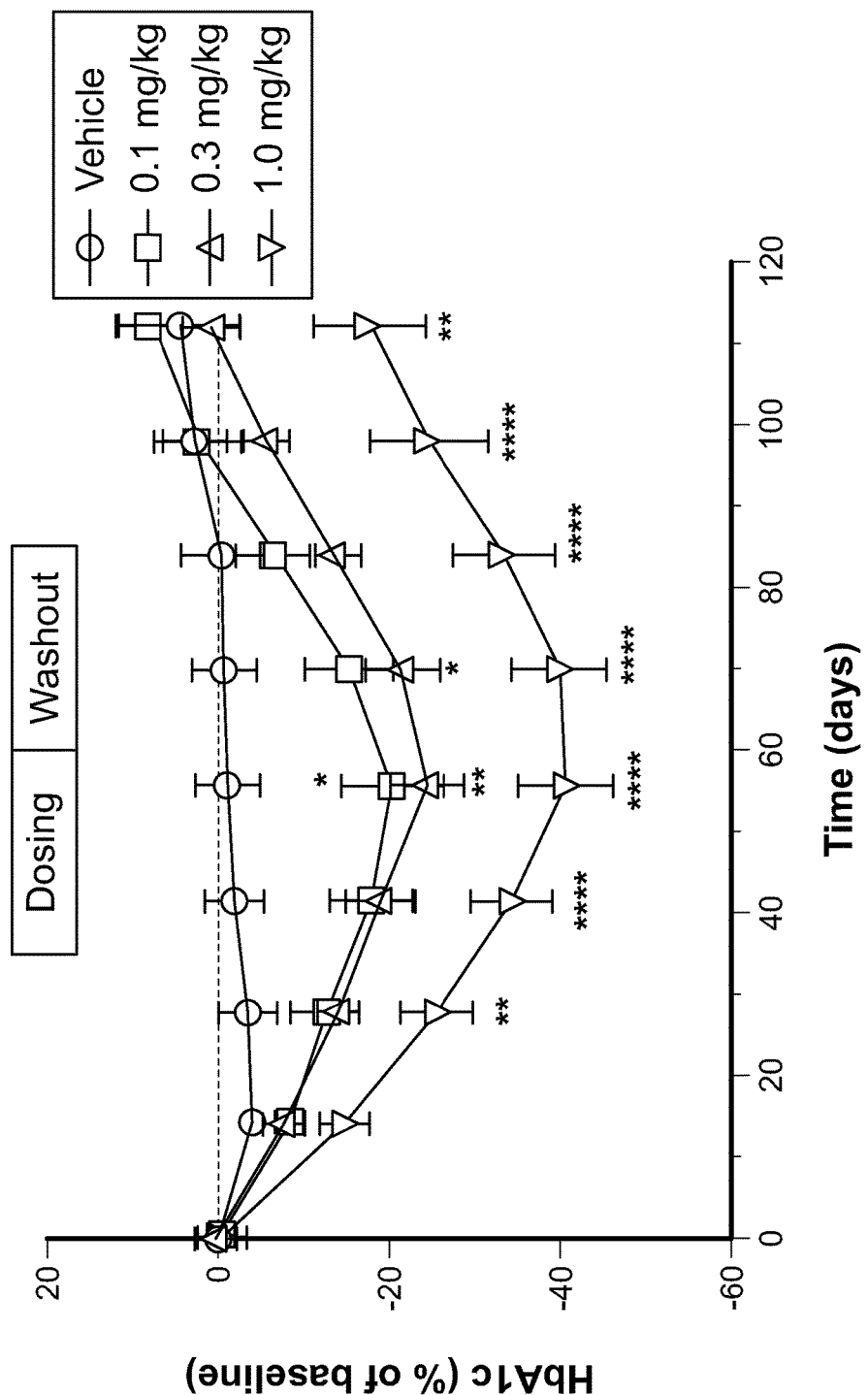

FIG. 8: Effect of the mutant 20 kDa PEG-FGF-21 (P(172)TQGAS) peptide conjugate on HbA1c in diabetic Cynomolgus monkeys (cf. Example 12).

Figure 9:
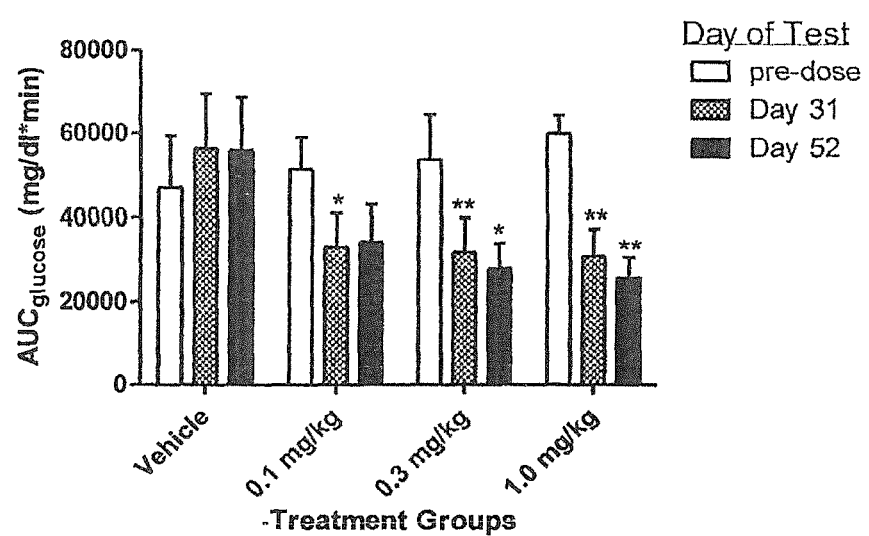

FIG. 9: Effect of the mutant FGF-21 peptide conjugate on oral glucose tolerance test (OGTT) (cf. Example 12). Data are shown as the area under the curve (AUC) for each treatment. *$p<0.05$, **$p<0.01$.

Figure 10:
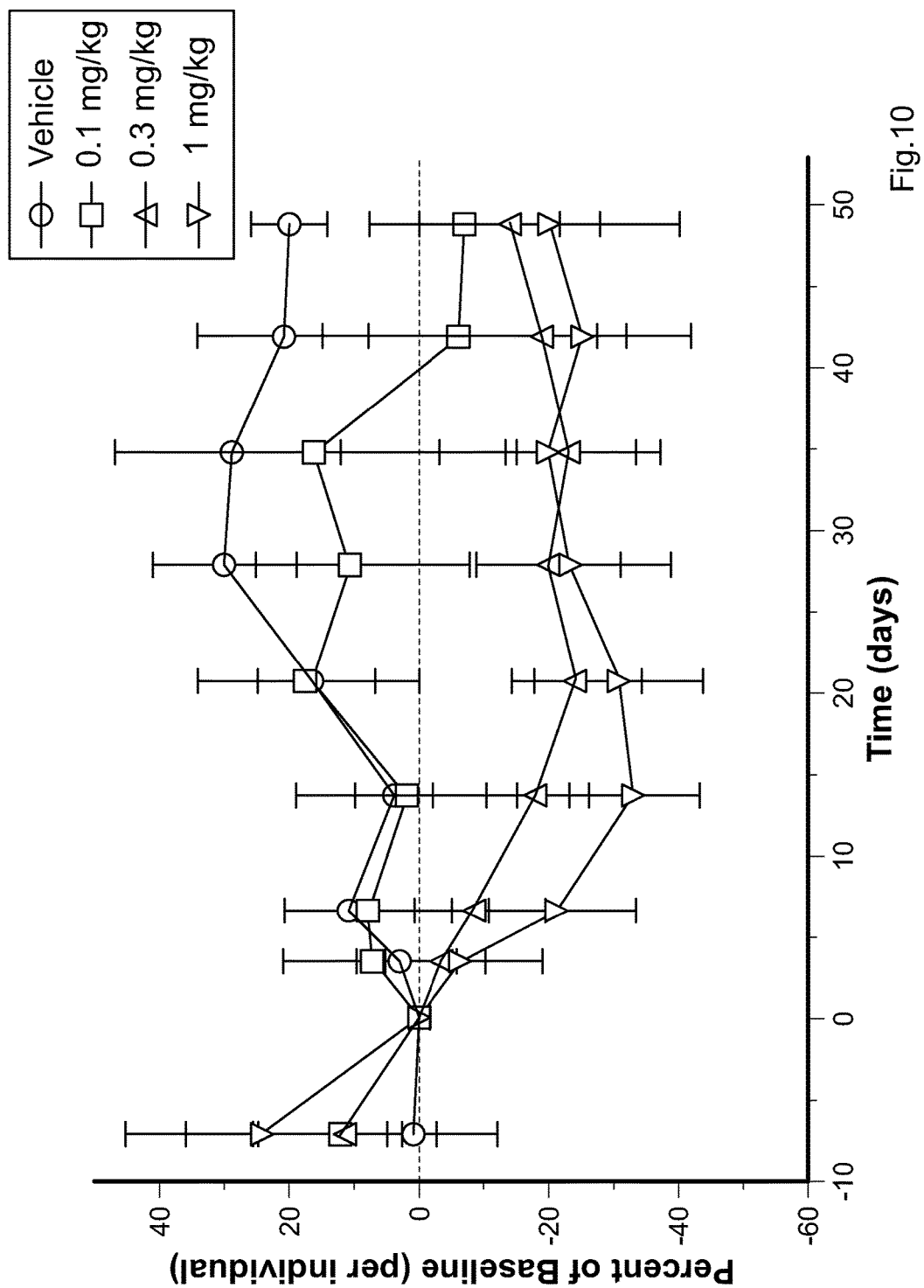

FIG. 10: Effect of the mutant FGF-21 peptide conjugate on serum ALT concentration in diabetic Cynomolgus monkeys.

Figure 11:
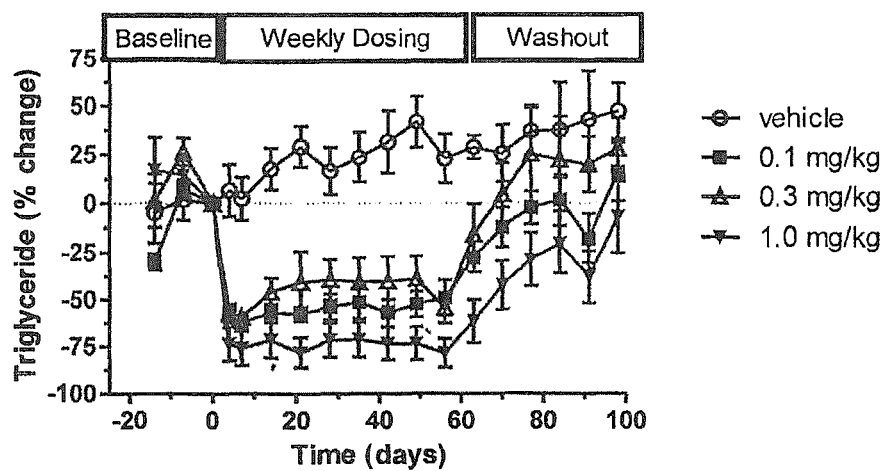

FIG. 11: Triglyceride levels in diabetic Cynomolgus monkeys treated with the mutant FGF-21 peptide conjugate.

Figure 12:
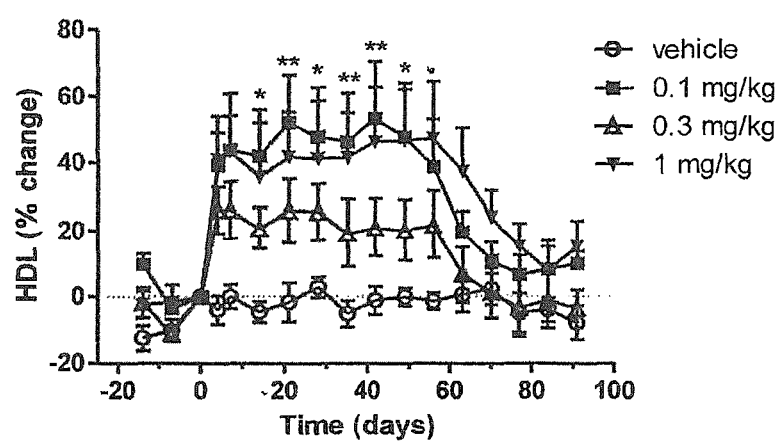

FIG. 12: HDL cholesterol levels in diabetic Cynomolgus monkeys treated with the mutant FGF-21 peptide conjugate.

Figure 13:
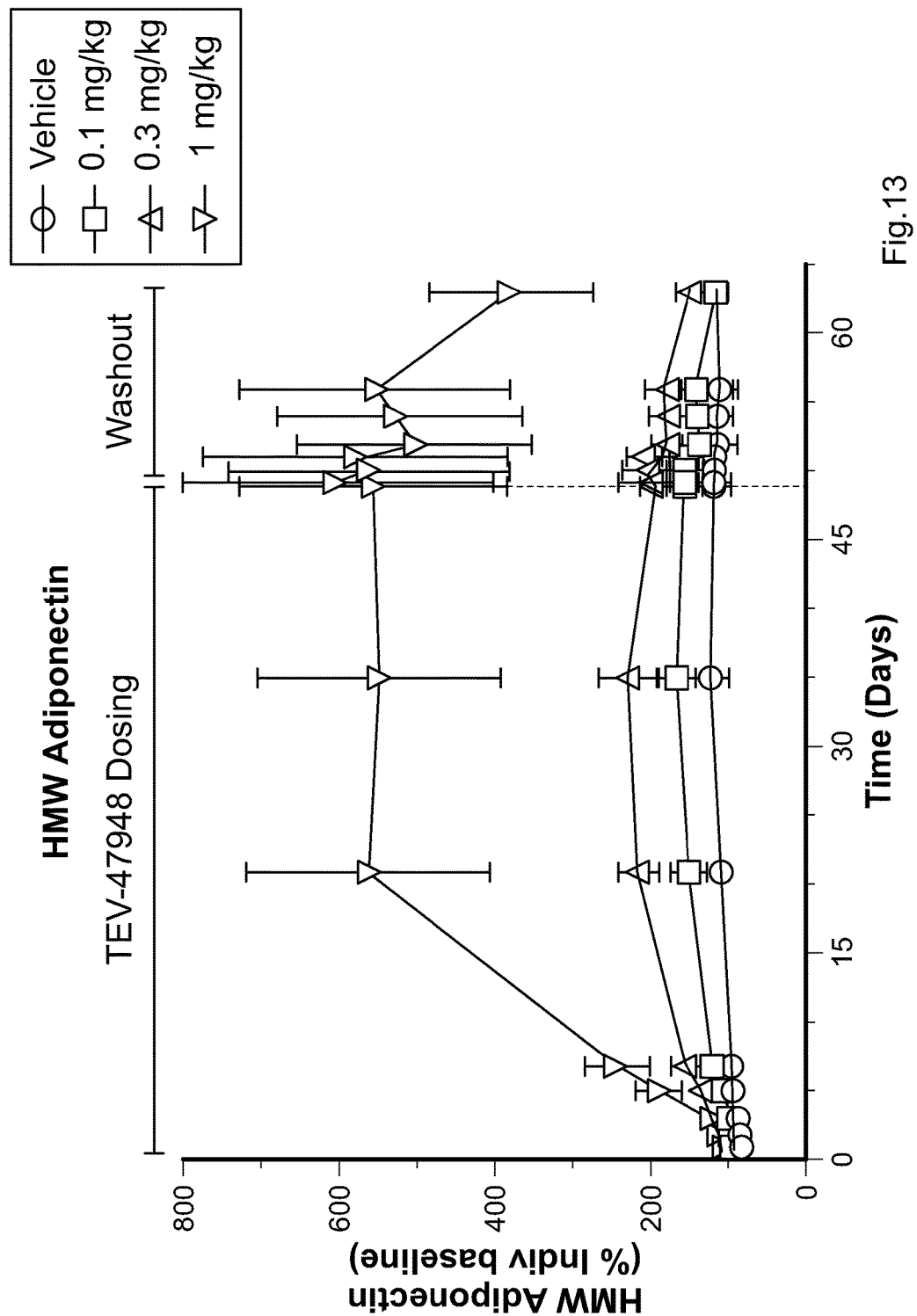

FIG. 13: Adiponectin levels in diabetic Cynomolgus monkeys treated with the mutant FGF-21 peptide conjugate.

Figure 14:
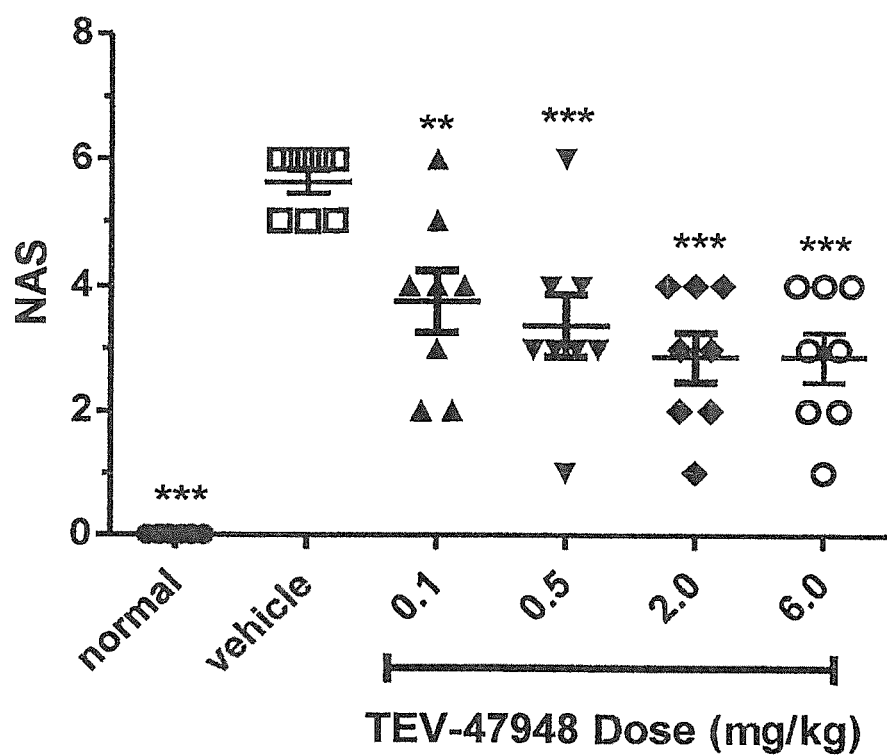
Figure 15:
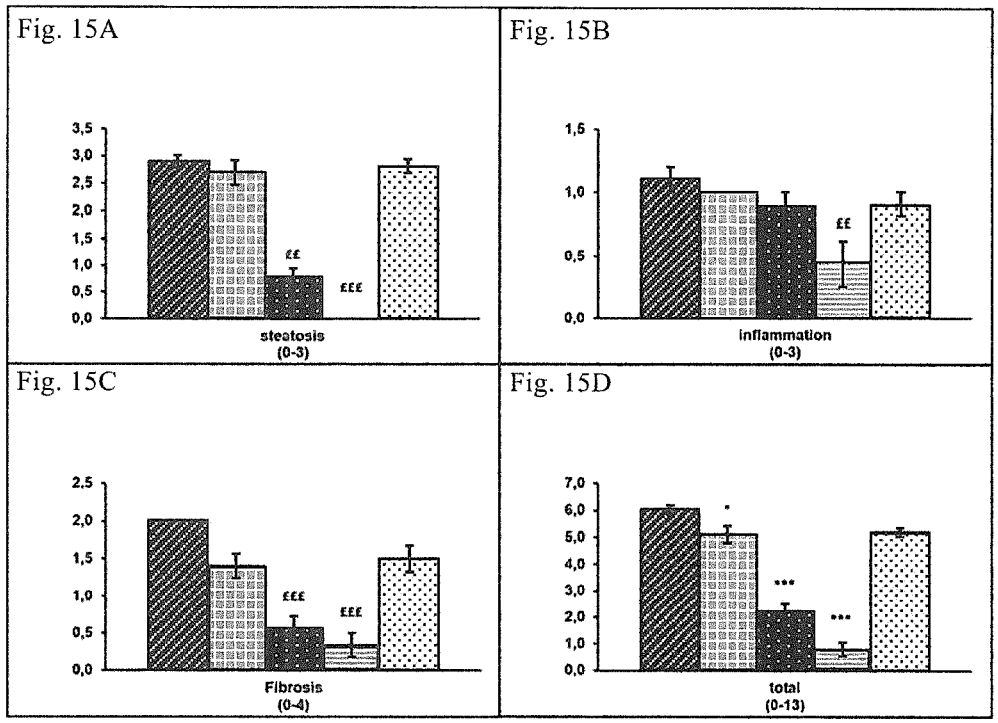
Figure 16:
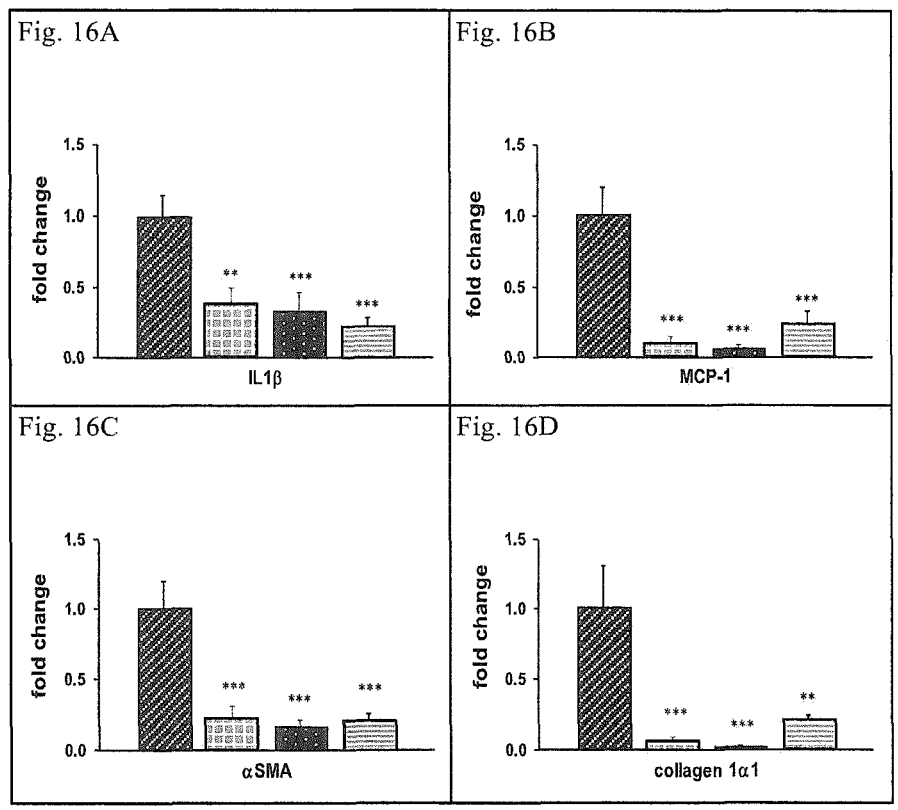

FIG. 14: NAFLD Activity Score in the STAM Model after treatment with the mutant FGF-21 peptide conjugate (referred to herein as TEV-47948). NAS=NAFLD Activity Score.

FIG. 15A-D: Mutant FGF-21 peptide conjugate (referred to herein as TEV-47948) significantly reduces NAFLD Activity Score (NAS) in the DIN (Diet induced NASH model) Model as reflected by a reduction in steatosis (A), inflammation (B), and fibrosis (C). Reduction in total NAS score is shown in (D).

FIG. 16A-D: Mutant FGF-21 peptide conjugate (referred to herein as TEV-47948) significantly reduces pro-inflammatory cytokine expression in the DIN Model as reflected by a reduction in interleukin 1 beta (IL1β) (A), monocyte chemoattractant protein-1 (MCP-1) (B), and alpha-smooth muscle actin (aSMA) (C), and collagen 1αl (D).

Figure 17:
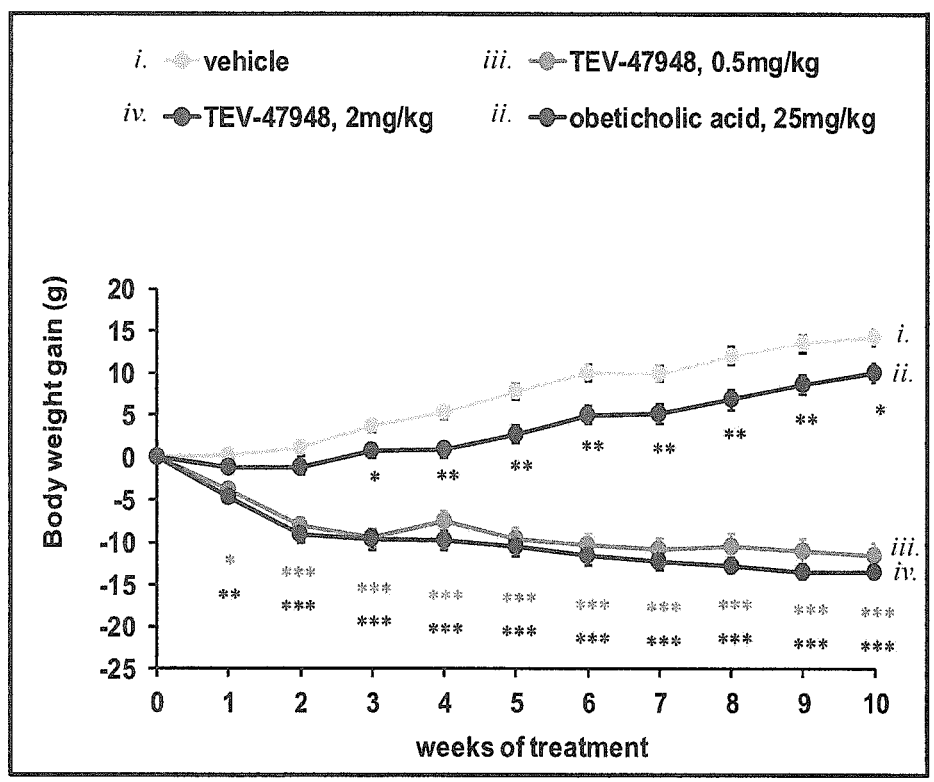

FIG. 17: Mutant FGF-21 peptide conjugate (referred to herein as TEV-47948) reduces body weight in the DIN Model.

Figure 18:
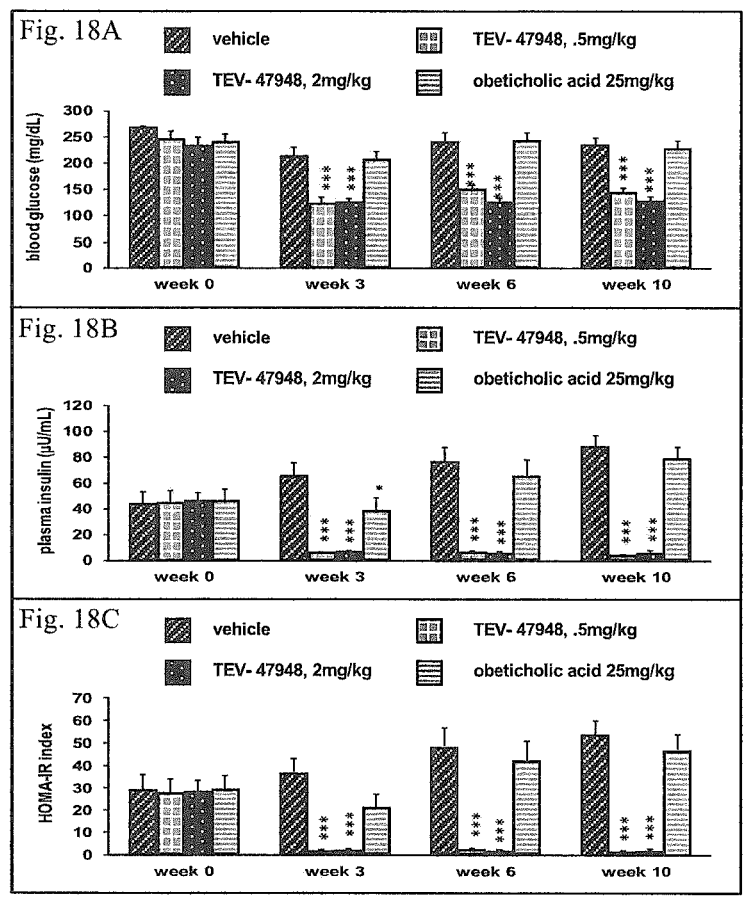

FIG. 18A-C: Mutant FGF-21 peptide conjugate (referred to herein as TEV-47948) significantly reduces glucose levels (A), plasma insulin (B), and Homeostatic Model Assessment of Insulin Resistance (HOMA-IR) (C) in the DIN Model.

Figure 19:
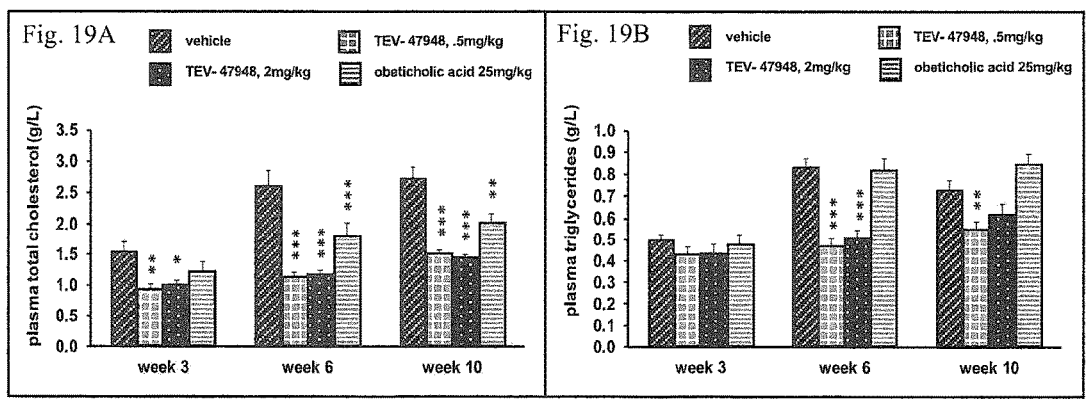

FIG. 19A-B: Mutant FGF-21 peptide conjugate (referred to herein as TEV-47948) significantly reduces total cholesterol levels (A) and total triglycerides (B) in the DIN Model.

Figure 20:
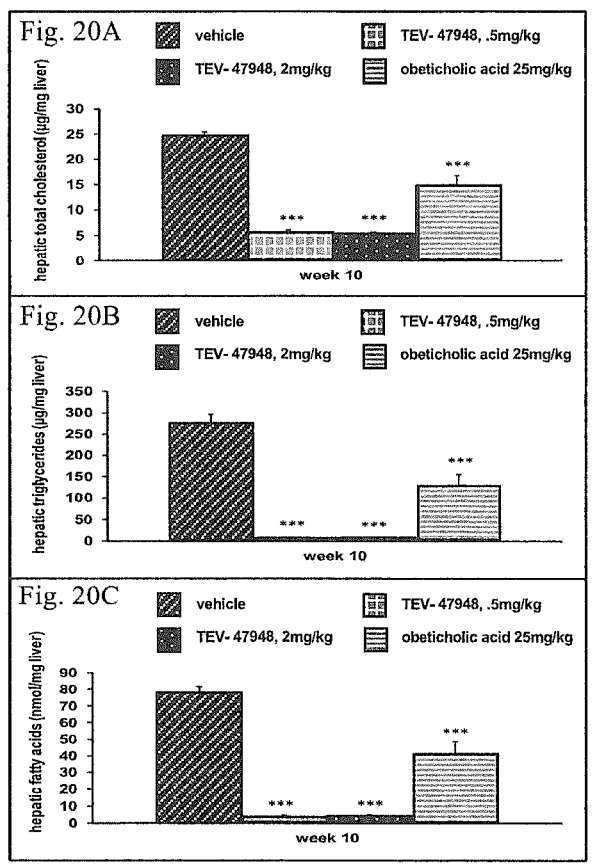

FIG. 20A-C: Mutant FGF-21 peptide conjugate (referred to herein as TEV-47948) significantly reduces hepatic cholesterol levels (A), hepatic triglycerides (B), and hepatic fatty acids (C) in the DIN Model.

Figure 21:
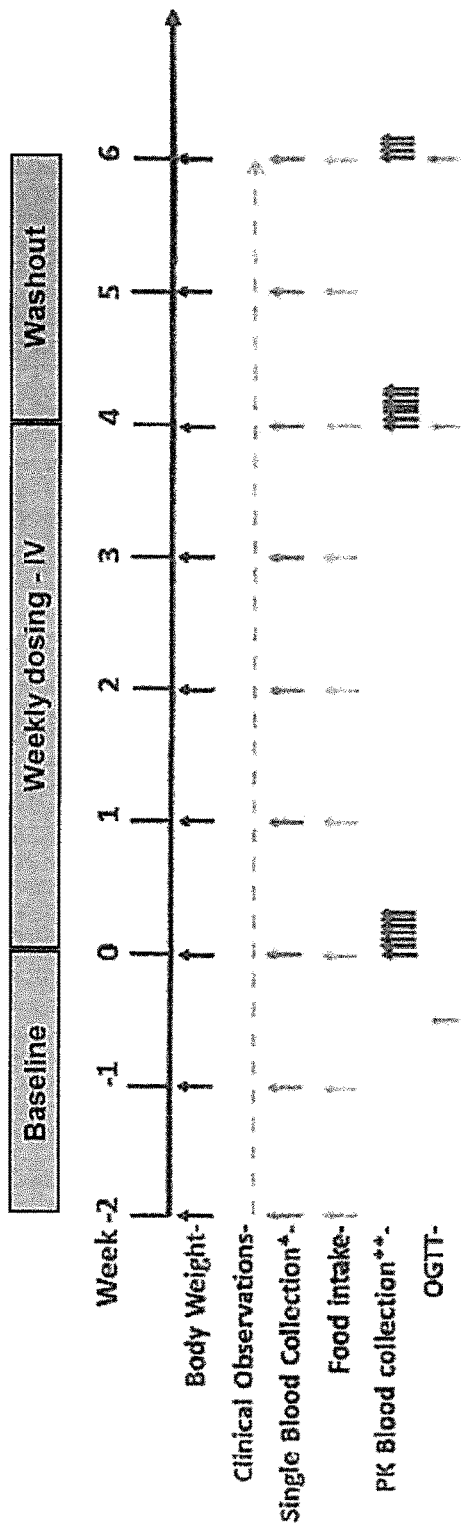

FIG. 21: A flowchart of the experimental design and data collection for Example 14.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive.

Definitions

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

Enzyme: Enzymes are catalytically active biomolecules that perform biochemical reactions such as the transfer of glycosyl moieties or modified glycosyl moieties from the respective glycosyl donors to an amino acid of FGF-21 or to another glycosyl moiety attached to the peptide.

Protein: A protein typically comprises one or more peptides or polypeptides. A protein is typically folded into a 3-dimensional form, which may be required for the protein to exert its biological function. The sequence of a protein or peptide is typically understood to be in the order, i.e. the succession of its amino acids.

Recombinant protein: The term "recombinant protein" refers to proteins produced in a heterologous system, that is, in an organism that naturally does not produce such a protein, or a variant of such a protein, i.e. the protein or peptide is "recombinantly produced". Typically, the heterologous systems used in the art to produce recombinant proteins are bacteria (e.g., *Escherichia* (*E.*) *coli*), yeast (e.g., *Saccharomyces* (*S.*) *cerevisiae*) or certain mammalian cell culture lines.

Expression host: An expression host denotes an organism which is used for recombinant protein production. General expression hosts are bacteria, such as *E. coli*, yeasts, such as *Saccharomyces cerevisiae* or *Pichia pastoris*, or also mammal cells, such as human cells.

RNA, mRNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Sequence of a nucleic acid molecule/nucleic acid sequence: The sequence of a nucleic acid molecule is typically understood to be in the particular and individual order, i.e. the succession of its nucleotides.

Sequence of amino acid molecules/amino acid sequence: The sequence of a protein or peptide is typically understood to be in the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence, such as a native or wild type sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences particularly relates to the percentage of nucleotides/amino acids of a sequence, which have the same position in two or more sequences having the same length. Gaps are usually regarded as non-identical positions, irrespective of their actual position in an alignment.

Newly introduced amino acids: "Newly introduced amino acids" denote amino acids which are newly introduced into an amino acid sequence in comparison to a native/wild type amino acid sequence. Usually by mutagenesis, the native amino acid sequence is changed in order to have a certain amino acid side chain at a desired position within the amino acid sequence. In the present invention, in particular the amino acid threonine is newly introduced into the amino acid sequence on the C-terminal side adjacent to a proline residue.

Functional group: The term is to be understood according to the skilled person's general understanding in the art and denotes a chemical moiety which is present on a molecule, in particular on the peptide or amino acid of the peptide or glycosyl residue attached to the peptide, and which may participate in a covalent or non-covalent bond to another chemical molecule, i.e. which allows e.g. the attachment of a glycosyl residue or PEG.

Native amino acid sequence: The term is to be understood according to the skilled person's general understanding in the art and denotes the amino acid sequence in the form of its occurrence in nature without any mutation or amino acid amendment by man. It is also called "wild-type sequence". "Native FGF-21" or "wild-type FGF-21" denotes FGF-21 having the amino acid sequence as it occurs in nature, such as the (not mutated) amino acid sequence of human FGF-21 as depicted in SEQ ID NO: 1. The presence or absence of an N-terminal methionine, which depends on the used expression host, usually does not change the status of a protein being considered as having its natural or native/wild-type sequence.

Mutated: The term is to be understood according to the skilled person's general understanding in the art. An amino acid sequence is called "mutated" if it contains at least one additional, deleted or exchanged amino acid in its amino acid sequence in comparison to its natural or native amino acid sequence, i.e. if it contains an amino acid mutation. Mutated proteins are also called mutants. In the present invention, a mutated FGF-21 peptide is particularly a peptide having an amino acid exchange adjacent to a proline residue on the C-terminal side of the proline residue. Thereby a consensus sequence for O-linked glycosylation is introduced into FGF-21 such that the mutant FGF-21 peptide comprises a newly introduced O-linked glycosylation side. Amino acid exchanges are typically denoted as follows: $S^{173}T$ which means that the amino acid serine at position 173, such as in the amino acid sequence of SEQ ID NO: 1, is exchanged by the amino acid threonine.

Pharmaceutically effective amount: A pharmaceutically effective amount in the context of the invention is typically understood to be an amount that is sufficient to induce a pharmaceutical effect.

Therapy/treatment: The term "therapy" refers to "treating" or "treatment" of a disease or condition, inhibiting the disease (slowing or arresting its development), providing relief from the symptoms or side-effects of the disease (including palliative treatment), and relieving the disease (causing regression of the disease).

Therapeutically effective amount: is an amount of a compound that is sufficient to treat a disease or condition, inhibit the disease or condition, provide relief from symptoms or side-effects of the disease, and/or cause regression of the disease or condition.

Half-life: The term "half-life", as used herein in the context of administering a mutant FGF-21 peptide and/or conjugate thereof, is defined as the time required for the plasma concentration of a drug, i.e. of the mutant FGF-21 peptide and/or conjugate, in a subject to be reduced by one half.

O-linked glycosylation: "O-linked glycosylation" takes place at serine or threonine residues (Tanner et al., Biochim. Biophys. Acta. 906:81-91 (1987); and Hounsell et al, Glycoconj. J. 13:19-26 (1996)). In the present invention, O-linked glycosylation sites, which are amino acid motifs in the amino acid sequence of a peptide which are recognized by glycosyl transferases as attachment points for glycosyl residues, include the amino acid motif proline-threonine (PT) not present in the native/wild-type amino acid sequence. In particular, the threonine residue is newly introduced adjacent to a proline and on the C-terminal side of a proline residue. The glycosyl moiety is then attached to the —OH group of the threonine residue by the glycosyl transferase.

Newly introduced O-linked glycosylation side: "Newly introduced O-linked glycosylation side" denotes an O-linked glycosylation side which did not exist in the native or wild-type FGF-21 before introducing a threonine adjacent to and on the C-terminal side of a proline residue as described herein.

Adjacent: Adjacent denotes the amino acid immediately next to another amino acid in the amino acid sequence, either on the N-terminal or on the C-terminal side of the respective amino acid. In the present invention, e.g. the newly introduced threonine residue is adjacent to a proline residue on the C-terminal side of a proline residue.

Glycosyl moiety: A glycosyl moiety is a moiety consisting of one or more, identical or different glycosyl residues which links the mutant FGF-21 peptide to a polyethylene glycol (PEG), thereby forming a conjugate comprising a peptide, glycosyl moiety and PEG. The glycosyl moiety can be a mono-, di-, tri-, or oligoglycosyl moiety. The glycosyl moiety may comprise one or more sialic acid residues, one or more N-acetylgalactosamine (GalNAc) residues, one or more galactose (Gal) residues and others. The glycosyl moiety may be modified, such as with a PEG or methoxy-PEG (m-PEG), an alkyl derivative of PEG.

Glycoconjugation: "Glycoconjugation", as used herein, refers to the enzymatically mediated conjugation of a PEG-modified glycosyl moiety to an amino acid or glycosyl residue of a (poly)peptide, e.g. a mutant FGF-21 of the present invention. A subgenus of "glycoconjugation" is "glyco-PEGylation" in which the modifying group of the modified glycosyl moiety is PEG or m-PEG. The PEG may be linear or branched. Typically, a branched PEG has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched PEG can be represented in general form as R(-PEG-OX)m in which R represents the core moiety, such as glycerol or pentaerythritol, X represents a capping group or an end group, and m represents the number of arms. The terms "glyco-PEG" and "glycosyl-PEG" are used interchangeably and denote a chemical moiety consisting of PEG or methoxy-PEG (mPEG or m-PEG), one or more glycosyl residues (or glycosyl moieties), and optionally a linker between PEG/methoxy-PEG and the glycosyl moieties, such as an amino acid, e.g. glycine. An example of a glycosyl-PEG/glyco-PEG moiety is PEG-sialic acid (PEG-Sia). It should be noted that the terms "glyco-PEG" and "glycosyl-PEG" as well as "PEG-sialic acid" and "PEG-Sia" as well as similar terms for glyco-PEG moieties may or may not include a linker between PEG and the glycosyl moiety or moieties, i.e. "PEG-sialic acid" encompasses e.g. PEG-sialic acid as well as PEG-Gly-sialic acid as well as mPEG-Gly-sialic acid.

Sequence motif: A sequence motif denotes a short amino acid sequence, such as that comprising only two amino acids, which is present at any possible position in a longer amino acid sequence, such as in the amino acid sequence of human FGF-21. Sequence motifs are e.g. denoted as $P^{172}T$ which means that the proline at position 172 is followed C-terminally immediately by a threonine residue.

Sialic acid: The term "sialic acid" or "Sia" refers to any member of a family of nine-carbon carboxylated sugars. The most common member of the sialic acid family is N-acetylneuraminic acid (2-keto-5-acetamido-3,5-dideoxy-D-glycero-D-galacto-nonulopyranos-1-onic acid (often abbreviated as Neu5Ac, NeuAc, or NANA). A second member of the family is N-glycolylneuraminic acid (Neu5Gc or NeuGc), in which the N-acetyl group of NeuAc is hydroxylated. A third sialic acid family member is 2-keto-3-deoxynonulosonic acid (KDN) (Nadano et al. (1986) J. Biol. Chem. 261:11550-11557). Also included are 9-substituted sialic acids such as a 9-0-$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see e.g. Varki, Glycobiology 2:25-40 (1992)).

Pharmaceutically acceptable excipient: "Pharmaceutically acceptable" excipient includes any material, which when combined with the mutant FGF-21 peptide conjugate of the invention retains the conjugates' activity and is non-reactive with a subject's immune systems. Examples include, but are not limited to, any of the standard pharmaceutical excipients such as a phosphate buffered saline solution, water, salts, emulsions such as oil/water emulsion, and various types of wetting agents.

Pharmaceutical container: A "pharmaceutical container" is a container which is suitable for carrying a pharmaceutical composition and typically made of an inert material and sterile.

Administering: The term "administering" means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g. oral, nasal, vaginal, rectal, or transdermal). Parenteral administration includes e.g. intravenous, intramuscular, intraarteriole, intradermal, subcutaneous, intraperitoneal, intraventricular and intracranial. Other modes of delivery include, but are not limited to, the use of liposomal formulations, intravenous infusion, transdermal patches, etc.

Diabetes and diabetes related diseases: "Diabetes" is a well-known and well-characterized disease often referred to as diabetes mellitus. The term describes a group of metabolic diseases in which the person has high blood glucose levels (blood sugar), either because insulin production is inadequate, or because the body's cells do not respond properly to insulin, or both. Patients with high blood sugar will typically experience polyuria (frequent urination), they will become increasingly thirsty (polydipsia) and hungry (polyphagia). "Diabetes related diseases" are diseases characterized by the same symptoms such as obesity, polyuria, polydipsia and polyphagia.

Diabetes type 2: "Diabetes type 2" is the most common form of diabetes/diabetes mellitus. Diabetes type 2 most commonly develops in adulthood and is more likely to occur in people who are overweight and physically inactive. Unlike type 1 diabetes, which currently cannot be prevented, many of the risk factors for type 2 diabetes can be modified. The International Diabetes Foundation lists four symptoms that signal the need for diabetes testing: a) frequent urination, b) weight loss, c) lack of energy and d) excessive thirst. Insulin resistance is usually the precursor to diabetes type 2 a condition in which more insulin than usual is needed for glucose to enter the cells. Insulin resistance in the liver results in more glucose production while resistance in peripheral tissues means glucose uptake is impaired.

Non-alcoholic steatohepatitis (NASH): a condition where fat is deposited in the liver with subsequent liver damage and inflammation.

Metabolic syndrome: a defined cluster of risk factors (biochemical and physiological changes) that are associated with the development of type 2 diabetes and cardiovascular disease.

DETAILED DESCRIPTION OF THE INVENTION

Recombinant FGF-21 has been shown to influence plasma glucose and insulin levels, to reduce hepatic and circulating triglycerides and cholesterol levels, and to improve insulin sensitivity, energy expenditure, hepatic steatosis and obesity in a range of insulin-resistant animal models. For this reason, FGF-21 is an interesting target for the treatment of human Type 2 diabetes, Nonalcoholic Steatohepatitis (NASH) and associated metabolic diseases.

Natural FGF-21 has a comparatively short half-life in vivo, with a reported circulating half-life ranging from 0.5 to 4 hours in rodents and non-human primates, which limits its clinical applicability. The half-life of recombinant human FGF-21 is 1-2 hours. To improve pharmacokinetic properties of FGF-21, various half-life extension strategies have been developed.

Abbreviations used herein include: PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc, sialyl or N-acetylneuraminyl; Sia, sialyl or N-acetylneuraminyl; and derivatives and analogues thereof.

PEGylation

One method to prolong a protein's half-life is the attachment of one or more PEG moieties to the protein, which attachment increases the protein's biophysical solubility and stability in general. This approach has proven to be of particular value with respect to increasing the therapeutic half-life of proteins having properties suitable for treating subjects in need thereof. Native FGF-21, however, lacks a specific protein PEGylation site. Chemical PEGylation absent a specific protein PEGylation site is not site-specific and typically results in the generation of an inhomogeneous product population requiring extensive purification to achieve a homogeneous and high purity product—a prerequisite for market approval as a pharmaceutical composition. Accordingly, site-specific PEGylation of FGF-21 is desirable for generating site-specific PEGylated FGF-21 peptides having improved half-life and good biological activity.

Enzyme-based syntheses have the advantages of regioselectivity and stereoselectivity. Moreover, enzymatic syntheses may be performed with unprotected substrates. One possible method to attach PEG residues site-specifically to a protein is glycoPEGylation. In glycoPEGylation, a PEG moiety may be transferred to an amino acid or glycosyl residue attached to an amino acid of the protein or peptide using a glycosyltransferase. The general final structure is protein-glycosyl moiety—optional further linker—PEG. A more particular final structure is protein—(N-, C- or internal) amino acid of the protein—one or more glycosyl residues—optional linker (e.g., amino acid linker)—linear or branched PEG moiety of various lengths, wherein the glycosyl moiety may comprise one or more glycosyl residues. The one or more glycosyl residues comprising at least part of the structure linking the protein to the PEG moiety may be any possible glycosyl residue. A diverse array of methods for glycoPEGylating proteins are known in the art and are described in detail herein below.

In protein PEGylation, the larger the conjugated PEG moiety, the longer the expected half-life of a PEG-conjugated protein. This is due to the relatively enhanced ability of larger PEG moieties to protect conjugated proteins from proteases present in the blood stream. Large PEG moieties confer a larger effective radius to a PEG-conjugated protein than smaller PEG moieties. Larger proteins are also degraded in and removed from the blood stream more slowly than smaller proteins because they enter the kidney more slowly or are prevented from entering the kidney completely. Accordingly, skilled persons favor PEGylation processes that call for attaching a longer PEG residue of higher molecular weight (e.g., ≥30 kDa PEG), a higher number of PEG residues in total, and/or more highly branched PEG residues to a protein in order to create a PEGylated protein having superior properties relative to the same protein conjugated to a shorter/smaller PEG moiety.

A considerable disadvantage associated with pegylation is, however, the potential for steric hindrance whereby a conjugated PEG moiety physically blocks an active site of the protein that is important or essential for protein activity. For example, a PEG moiety may specifically block a receptor binding site of a protein for its receptor, which in turn, leads to a significant and detrimental loss in protein activity. To avoid such potential inhibitory effects of pegylation, persons skilled in the art avoid attaching PEG near amino acids involved in receptor binding.

With respect to FGF-21, the C-terminus is critical for β-Klotho binding and the N-terminus is important for FGFR activation. Moreover, in silico modeling of FGF-21 based on the crystal structures of other FGF-21 family proteins and in vitro potency assays demonstrated that PEGylation of amino acid residues located in the putative receptor binding domains were inactive, while PEGylation at distal sites produced the most active analogs. Furthermore, greater than 100-fold loss of potency was observed in a cell based potency assay when a PEG moiety was placed at position 180 in FGF-21. Fusion of FGF-21 to the Fc portion of an antibody was also examined, and fusion at the C-terminus of FGF-21 produced a much weaker analog than fusion at the N-terminus. In contrast, N-terminally PEGylated FGF-21 has been generated and shown to be biologically active. Based on knowledge in the field, therefore, a skilled person would avoid PEGylation close to the C-terminus of FGF-21 in light of the role this region of the protein plays in binding and signaling.

Against this backdrop, the present inventors set out to generate a plurality of mutant Fibroblast Growth Factor-21 (FGF-21) peptide conjugates, each comprising i) a mutant FGF-21 peptide comprising at least one threonine (T) residue adjacent to at least one proline (P) residue on the C-terminal side of said at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and ii) a 20 kDa polyethylene glycol (PEG), wherein said 20 kDa PEG is covalently attached to said mutant FGF-21 peptide at said at least one threonine residue via at least one glycosyl moiety.

In a particular embodiment, the mutant FGF-21 peptide conjugate comprises a mutant FGF-21 peptide comprising the amino acid sequence PT. In particular embodiments thereof, the mutant FGF-21 peptide comprises at least one amino acid sequence selected from the group consisting of P172T, P156T, P5T, P3T, P9T, P50T, P61T, P79T, P91T, P116T, P129T, P131T, P134T, P139T, P141T, P144T, P145T, P148T, P150T, P151T, P158T, P159T, P166T, P178T and combinations thereof, wherein the positions of proline and threonine are based on the amino acid sequence as depicted in SEQ ID NO: 1. In a more particular embodiment, the mutant FGF-21 peptide comprises at least one amino acid sequence selected from the group consisting of P172T, P156T, P5T and combinations thereof, particularly consisting of P172T, P156T and combinations thereof, wherein the positions of proline and threonine are based on the amino acid sequence as depicted in SEQ ID NO: 1. In a still more particular embodiment, the proline residue is located between amino acid 145 and the C-terminus of the mutant FGF-21 peptide, wherein the position of amino acid 145 is based on the amino acid sequence as depicted in SEQ ID NO: 1.

In another particular embodiment, the mutant FGF-21 peptide comprises the amino acid sequence P172T, wherein the positions of proline and threonine are based on the amino acid sequence as depicted in SEQ ID NO: 1.

In another particular embodiment, the mutant FGF-21 peptide comprises the mutations S173T and R176A, wherein the positions of the amino acids S and R are based on the amino acid sequence as depicted in SEQ ID NO: 1, particularly the mutant FGF-21 peptide comprises the amino acid sequence as depicted in SEQ ID NO: 2.

In another particular embodiment, the mutant FGF-21 peptide comprises the mutation Q157T, wherein the position of the amino acid Q is based on the amino acid sequence as depicted in SEQ ID NO: 1, particularly the mutant FGF-21 peptide comprises the amino acid sequence as depicted in SEQ ID NO: 4.

In another particular embodiment, the mutant FGF-21 peptide comprises the mutation D6T, wherein the position of the amino acid D is based on the amino acid sequence as depicted in SEQ ID NO: 1, particularly the mutant FGF-21 peptide comprises the amino acid sequence as depicted in SEQ ID NO: 5.

In other particular embodiments, the mutant FGF-21 peptide comprises an amino acid sequence selected from the group consisting of SEQ ID NOs: 2 to 28, particularly an amino acid sequence selected from the group consisting of SEQ ID NOs: 2 to 5, more particularly an amino acid sequence selected from the group consisting of SEQ ID NOs: 2 to 4, and most particularly the mutant FGF-21 peptide comprises the amino acid sequence as depicted in SEQ ID NO: 2.

In other particular embodiments, the mutant FGF-21 peptide conjugate comprises at least one glycosyl moiety comprising N-acetylgalactosamine (GalNAc), galactose (Gal) and/or sialic acid (Sia). In a particular embodiment thereof, the at least one glycosyl moiety comprises the structure -GalNAc-Sia-.

In other particular embodiments, the mutant FGF-21 peptide conjugate comprises a 20 kDa PEG moiety which is attached to the at least one glycosyl moiety via an amino acid residue, particularly glycine (Gly). In an even more particular embodiment, the mutant FGF-21 peptide conjugate comprises the structure -GalNAc-Sia-Gly-PEG(20 kDa). Still more particularly, the mutant FGF-21 peptide conjugate comprises the structure:

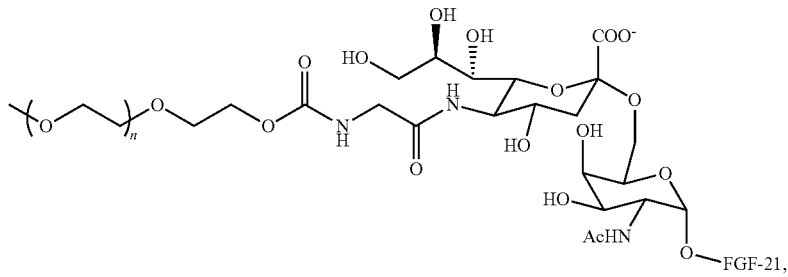

wherein n is an integer selected from 450 to 460.

In other particular embodiments, the mutant FGF-21 peptide conjugate comprises a 20 kDa PEG which is a linear or branched PEG, particularly a linear PEG. Still more particularly, the 20 kDa PEG is a 20 kDa methoxy-PEG.

Also encompassed herein is a pharmaceutical composition comprising at least one mutant FGF-21 peptide conjugate described herein and a pharmaceutically acceptable carrier. In a particular embodiment, the mutant FGF-21 peptide conjugate is present in a concentration in the range from 0.1 mg/mL to 50 mg/mL, particularly from 1 mg/mL to 45 mg/mL, more particularly from 10 mg/mL to 40 mg/mL, most particularly in a concentration of 26±4 mg/mL. The buffering agent may be a Tris buffer. The buffering agent may be present in a concentration from 1 mM to 100 mM, particularly from 2 mM to 75 mM, more particularly from 5 mM to 50 mM, even more particularly from 10 mM to 25 mM, most particularly of 16±2 mM. The pH may be in the range from 6.0 to 8.5, particularly from 6.5 to 8.0, more particularly from 6.75 to 8.0, and most particularly is 7.5±0.3. The pharmaceutical composition may further comprise a salt, particularly an inorganic salt, more particularly NaCl. The pharmaceutical composition may comprise a salt which is present in a concentration from 30 mM to 200 mM, particularly from 40 mM to 150 mM, more particularly from 50 mM to 100 mM, most particularly of 56±2 mM. The pharmaceutical composition may further comprise a tonicity modifying agent. Suitable tonicity modifying agents include glycerol, amino acids, sodium chloride, proteins, or sugars and sugar alcohols, particularly the tonicity modifying agent is a sugar, and more particularly the tonicity modifying agent is sucrose. The tonicity modifying agent is present in a concentration of 50 mM to 200 mM, more particularly in a concentration of 100 mM to 175 mM, even more particularly is present in a concentration of 135 mM to 160 mM, and most particularly in a concentration of 150±2 mM. The pharmaceutical composition may further comprise a surfactant, particularly a non-ionic surfactant. The surfactant or non-ionic surfactant may be a polysorbate-based non-ionic surfactant, particularly polysorbate 20 or polysorbate 80, and more particularly polysorbate 20. The surfactant or non-ionic surfactant may be present in a concentration of 0.01 mg/mL to 1 mg/mL, particularly in a concentration of 0.05 to 0.5 mg/mL and more particularly in a concentration of 0.2±0.02 mg/mL.

In a particular embodiment, the pharmaceutical composition comprises 0.1 mg/mL to 50 mg/mL of mutant FGF-21 peptide conjugate, 1 mM to 100 mM buffering agent, particularly Tris buffer, 30 mM to 200 mM mM salt, particularly NaCl, 50 mM to 200 mM tonicity modifying agent, particularly sucrose, and 0.01 mg/mL to 1 mg/mL surfactant or non-ionic surfactant, particularly polysorbate 20, and has a pH of 6.0 to 8.5.

A pharmaceutical container comprising at least one of the mutant FGF-21 peptide conjugates described herein and/or a pharmaceutical composition comprising same are also encompassed herein. Suitable pharmaceutical containers include, without limitation, a syringe, vial, infusion bottle, ampoule, carpoule, a syringe equipped with a needle protection system, and a carpoule within an injection pen.

Also encompassed herein is a method of producing the mutant FGF-21 peptide conjugate according to any one of embodiments 1 to 17, comprising the steps of: (1) recombinantly producing the mutant FGF-21 peptide in an expression host; and (2) enzymatically attaching to the mutant FGF-21 peptide of step (1) a PEG-glycosyl moiety, wherein the PEG has 20 kDa, thereby forming the mutant FGF-21 peptide conjugate. In a particular embodiment, the expression host is *Escherichia coli*. In a more particular embodiment, step (2) comprises a step (2a) of contacting the mutant FGF-21 peptide with a GalNAc donor and a GalNAc transferase under conditions suitable to transfer GalNAc from the GalNAc donor to the at least one threonine residue of the mutant FGF-21 peptide. In a still more particular embodiment, the GalNAc donor is UDP-GalNAc. In another particular embodiment, the GalNAc transferase is MBP-GalNAcT2. In another particular embodiment, step (2) further comprises a step (2b) of contacting the product of step (1) or of step (2a), if present, with a 20 kDa PEG-Sia donor and a sialyltransferase under conditions suitable to transfer 20 kDa PEG-Sia from the 20 kDa PEG-Sia donor to the at least one threonine residue of the mutant FGF-21 peptide or to the GalNAc at the mutant FGF-21 peptide if step (2a) is present. In a more particular embodiment, the 20 kDa PEG-Sia donor is 20 kDa PEG-Sia-CMP. In a still more particular embodiment, the sialyltransferase is ST6GalNAc1. In a still further particular embodiment, the 20 kDa PEG-Sia donor comprises the structure

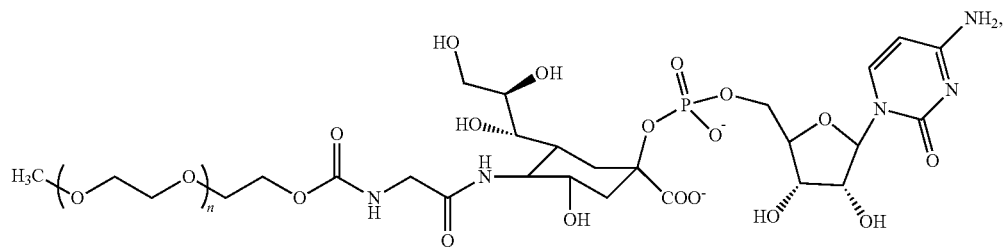

wherein n is an integer selected from 450 to 460.

In another particular embodiment, the method further comprises a step (3), after step (1) and prior to step (2), of purifying the mutant FGF-21 peptide after recombinant production. In a more particular embodiment, the method further comprises a step (4), after step (2), of purifying the mutant FGF-21 peptide conjugate formed in step (2). In another particular embodiment, the method, wherein step (3) comprises subjecting the mutant FGF-21 peptide and/or step (4) comprises subjecting the mutant FGF-21 peptide conjugate, the method may comprise ion exchange chromatography, affinity chromatography, filtration or combinations thereof. More particularly, wherein the step of purifying comprises one or more steps of ion exchange chromatography, it particularly comprises two steps of ion exchange chromatography. In another particular embodiment, wherein the ion exchange chromatography is an anion exchange chromatography, it is more particularly a strong anion exchange chromatography. More particularly, wherein the anion exchange chromatography employs a member, it is selected from the group consisting of a hydrophilic polyvinyl ether base matrix, polystyrene/divinyl benzene polymer matrix, trimethylammoniumethyl (TEAE), diethylaminoethanol (DEAE), agarose, a quaternary ammonium (Q) strong anion exchange chromatography and combinations thereof. In another particular embodiment, wherein in step (3) two anion exchange chromatography steps are performed, such steps use a hydrophilic polyvinyl ether base matrix. Still more particularly, wherein in step (4) quaternary ammonium (Q) strong anion exchange chromatography steps are performed, two quaternary ammonium (Q) strong anion exchange chromatography steps are performed. More particularly, wherein arginine is added in step (2) and/or, if present, in step (3), it is particularly at least 400 mM arginine. In a more particular embodiment, the method may further comprise a step (5), after step (3) and prior to step (2), of endotoxin removal, wherein the product of step (3) is filtered using an endotoxin removal filter.

In a further aspect, a mutant FGF-21 peptide conjugate obtainable by the above methods is encompassed, as are pharmaceutical compositions thereof that further comprise a pharmaceutically acceptable excipient or carrier.

In another aspect, a method for treating diabetes and related diseases, particularly diabetes type 2, non-alcoholic steatohepatitis (NASH) and/or metabolic syndrome is presented, the method comprising administering to a subject in need thereof a therapeutically effective amount of a mutant FGF-21 peptide conjugate described herein or a pharmaceutical composition comprising at least one of the mutant FGF-21 peptide conjugates described herein. In a particular embodiment, the subject in need thereof is a human subject.

Methods for Glycosylation and Glycoconjugation of FGF-21 Peptides

Post-expression in vitro modification of peptides and proteins is commonly used to produce glycopeptides and glycoproteins. A diverse array of enzymes that transfer saccharide donor moieties is available, thereby making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; WO 05/089102; WO 06/050247; WO 12/016984; US2002/142370; US2003/040037; US2003/180835; US2004/063911; US2003/207406; and US2003/124645, each of which is incorporated herein by reference.

Due to the versatility of the enzymes and methods available for adding and/or modifying glycosyl residues on a peptide, the glycosyl linking groups can have substantially any structure. Accordingly, glycosyl linking groups can comprise virtually any mono- or oligo-saccharide. The glycosyl linking groups can be attached to an amino acid either through the side chain or through the peptide backbone. Alternatively the glycosyl linking groups can be attached to the peptide through a saccharyl moiety, which moiety can be a portion of an O-linked or N-linked glycan structure on the peptide.

In accordance with the above, the present inventors set out to make conjugates of glycosylated mutant FGF-21, which have glycosylation sites that do not exist in the corresponding wild-type FGF-21 sequence. Such conjugates were formed by the enzymatic attachment of a modified sugar to the glycosylated FGF-21 peptide. The modified sugar, when interposed between the peptide and the modifying group on the sugar may be referred to herein as "a glycosyl linking group." Taking advantage of the exquisite selectivity of enzymes, such as glycosyltransferases, the present inventors generated mutant FGF-21 peptides having a desired group at one or more specific locations. More particularly, the present inventors used glycosyltransferases to attach modified sugars to carbohydrate moieties on mutant FGF-21 glycopeptides.

FGF-21 Conjugates

In another aspect, exemplary conjugates of a modified sugar and a mutant FGF-21 peptide are presented. See, for example, Examples 1-7 herein below. More particularly, mutant FGF-21 peptide conjugates were made comprising a mutant FGF peptide and at least one modified sugar, wherein a first of the at least one modified sugars is linked to an amino acid of the peptide through a glycosyl linking group. As described herein, the amino acid to which the glycosyl linking group is attached is mutated to create a site recognized by the glycosyltransferase.

In another exemplary embodiment, a mutant FGF-21 peptide conjugate can comprise a mutant FGF-21 peptide and a glycosyl group attached to the mutated amino acid residue of the mutant FGF-21 peptide.

In an exemplary embodiment, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

Modified Sugars

In an exemplary embodiment, mutant FGF-21 peptides are reacted with a modified sugar, thus forming a peptide conjugate. A modified sugar comprises a "sugar donor moiety" as well as a "sugar transfer moiety". The sugar donor moiety is any portion of the modified sugar that will be attached to the peptide, either through a glycosyl moiety or amino acid moiety, as a conjugate described herein. The sugar donor moiety includes those atoms that are chemically altered during their conversion from the modified sugar to the glycosyl linking group of the mutant FGF-21 peptide conjugate. The sugar transfer moiety is any portion of the modified sugar that will be not be attached to the peptide as a conjugate described herein.

For modified sugars described herein, the saccharyl moiety may be a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the saccharyl moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any saccharyl moiety can be utilized as the sugar donor moiety of the modified sugar. The saccharyl moiety can be a known sugar, such as mannose, galactose or glucose, or a species having the stereochemistry of a known sugar. The general formulae of these modified sugars are:

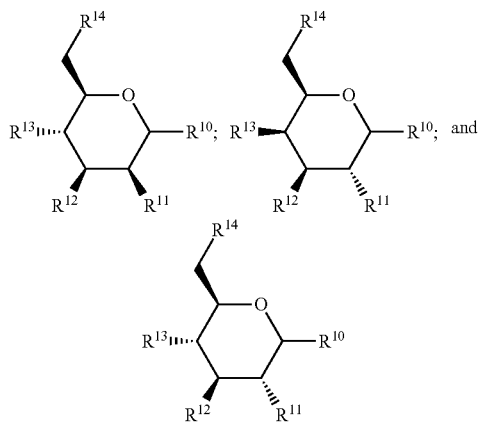

Other saccharyl moieties that are useful in methods described herein include, but are not limited to fucose and sialic acid, as well as amino sugars such as glucosamine, galactosamine, mannosamine, the 5-amine analogue of sialic acid and the like. The saccharyl moiety can be a structure found in nature or it can be modified to provide a site for conjugating the modifying group. For example, in one embodiment, the modified sugar provides a sialic acid derivative in which the 9-hydroxy moiety is replaced with an amine. The amine is readily derivatized with an activated analogue of a selected modifying group. Examples of modified sugars useful in methods described herein are presented in PCT Patent Application No. PCT/US05/002522, which is incorporated herein by reference in its entirety.

In a further exemplary embodiment, the invention utilizes modified sugars in which the 6-hydroxyl position is converted to the corresponding amine moiety, which bears a linker-modifying group cassette such as those set forth above. Exemplary glycosyl groups that can be used as the core of these modified sugars include Gal, GalNAc, Glc, GlcNAc, Fuc, Xyl, Man, and the like. A representative modified sugar according to this embodiment is set forth below:

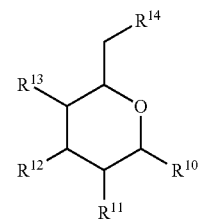

in which $R^{11}$-$R^{14}$ are members independently selected from H, OH, C(O)CH$_3$, NH, and NH C(O)CH$_3$. $R^{10}$ is a link to, e.g., another glycosyl residue (—O-glycosyl). $R^{14}$ is $OR^1$, $NHR^1$ or NH-L-$R^1$. $R^1$ and NH-L-$R^1$ are as described herein.

In a still further exemplary embodiment, the glycosyl groups used as the core of modified sugars in which the 6-hydroxyl position is converted to the corresponding amine moiety include Gal and/or GalNAc.

Glycosyl Linking Groups

In an exemplary embodiment, mutant FGF-21 peptide conjugates comprising a modified sugar described herein and a mutant FGF peptide are presented. In this embodiment, the sugar donor moiety (such as the saccharyl moiety and the modifying group) of the modified sugar becomes a "glycosyl linking group". The "glycosyl linking group" can alternatively refer to the glycosyl moiety which is interposed between the peptide and the modifying group.

In the exemplary embodiments that follow, the invention is illustrated by reference to the use of selected derivatives of furanose and pyranose. Those of skill in the art will appreciate that the structures and compositions set forth are generally applicable across the genus of glycosyl linking groups and modified sugars. The glycosyl linking group can, therefore, comprise virtually any mono- or oligo-saccharide.

In an exemplary embodiment, methods described herein utilize a glycosyl linking group that has the formula:

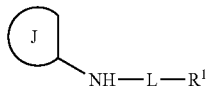

in which J is a glycosyl moiety, L is a bond or a linker and $R^1$ is a modifying group, e.g., a polymeric modifying group. Exemplary bonds are those that are formed between an NH$_2$ moiety on the glycosyl moiety and a group of complementary reactivity on the modifying group. For example, when $R^1$ includes a carboxylic acid moiety, this moiety may be activated and coupled with the $NH_2$ moiety on the glycosyl residue affording a bond having the structure $NHC(O)R^1$. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the conjugates, e.g., between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

An exemplary species of $NH-L-R^1$ has the formula: $-NH\{C(O)(CH_2)_aNH\}_s\{C(O)(CH_2)_b(OCH_2CH_2)_cO(CH_2)_d\cdot NH\}_tR^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —$CH_2$. As is understood in the art, one or more of the bracketed moieties corresponding to indices s and t can be replaced with a substituted or unsubstituted alkyl or heteroalkyl moiety.

More particularly, compounds described herein may comprise NH-L-R', wherein NH-L-R' is: $NHC(O)(CH_2)_aNHC(O)(CH_2)_b(OCH_2CH_2)_cO(CH_2)_dNHR^1$, $NHC(O)(CH_2)_b(OCH_2CH_2)_cO(CH_2)_dNHR^1$, $NHC(O)O(CH_2)_b(OCH_2CH_2)_cO(CH_2)_dNHR^1$, $NH(CH_2)_aNHC(O)(CH_2)_b(OCH_2CH_2)_cO(CH_2)_dNHR^1$, $NHC(O)(CH_2)_aNHR^1$, $NH(CH_2)_aNHR^1$, and $NHR^1$. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD, 25 kD, 30 kD, 35 kD, 40 kD, 45 kD, 50 kD, 55 kD, 60 kD or 65 kD.

In a more particular embodiment, the c is selected such that the PEG moiety ranges from 15-25 kD, 16-25 kD, 17-25 kD, 18-25 kD, 19-25 kD, 20-25 kD, 21-25 kD, 22-25 kD, 23-25 kD, 24-25 kD, 15-20 kD, 16-20 kD, 17-20 kD, 18-20 kD, 19-20 kD, 20-30 kD, 21-30 kD, 22-30 kD, 23-30 kD, 24-30 kD, 25-30 kD, 26-30 kD, 27-30 kD, 28-30 kD, 29-30 kD. In a still more particular embodiment, the c is selected such that the PEG moiety is 20 kD, 22 kD, 23 kD, 24 kD, 25 kD, 26 kD, 27 kD, 28 kD, 29 kD, or 30 kD.

For the purposes of clarity, the glycosyl linking groups in the remainder of this section are based on a sialyl moiety. However, one of skill in the art will recognize that another glycosyl moiety, such as mannosyl, galactosyl, glucosyl, or fucosyl, could be used in place of the sialyl moiety.

In an exemplary embodiment, the glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. In an exemplary embodiment, the invention provides a peptide conjugate comprising an intact glycosyl linking group having a formula that is selected from:

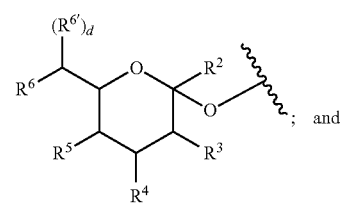

I

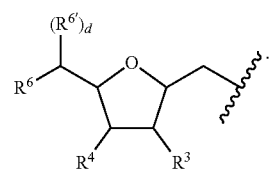

II

In Formulae I $R^2$ is H, $CH_2OR^7$, $COOR^7$ or $OR^7$, in which $R^7$ represents H, substituted or unsubstituted alkyl or substituted or unsubstituted heteroalkyl. When $COOR^7$ is a carboxylic acid or carboxylate, both forms are represented by the designation of the single structure COO⁻ or COOH. In Formulae I and II, the symbols $R^3$, $R^4$, $R^5$, $R^6$ and $R^{6'}$ independently represent H, substituted or unsubstituted alkyl, $OR^8$, $NHC(O)R^9$. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes a modifying group. This modifying group can be a polymeric modifying moiety e.g., PEG, linked through a bond or a linking group. In an exemplary embodiment, $R^6$ and $R^{6'}$, together with the carbon to which they are attached are components of the pyruvyl side chain of sialic acid. In a further exemplary embodiment, the pyruvyl side chain is functionalized with the polymeric modifying group. In another exemplary embodiment, $R^6$ and $R^{6'}$, together with the carbon to which they are attached are components of the side chain of sialic acid and the polymeric modifying group is a component of $R^5$.

Exemplary modifying group-intact glycosyl linking group cassettes according to this motif are based on a sialic acid structure, such as those having the formulae:

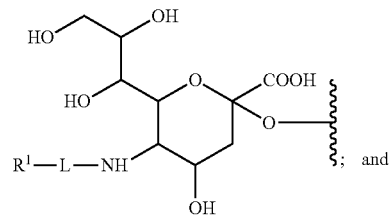

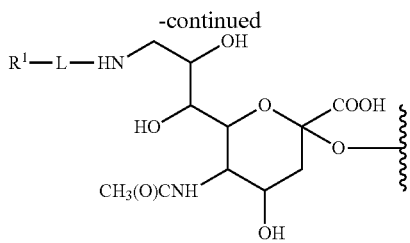

In the formulae above, $R^1$ and L are as described above. Further detail about the structure of exemplary $R^1$ groups is provided below.

In still a further exemplary embodiment, the conjugate is formed between a peptide and a modified sugar in which the modifying group is attached through a linker at the 6-carbon position of the modified sugar. Thus, illustrative glycosyl linking groups according to this embodiment have the formula:

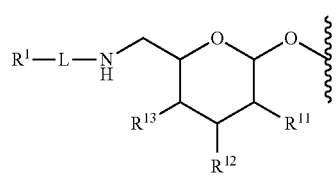

in which the radicals are as discussed above. Glycosyl linking groups include, without limitation, glucose, glucosamine, N-acetyl-glucosamine, galactose, galactosamine, N-acetylgalactosamine, mannose, mannosamine, N-acetylmannosamine, and the like.

In one embodiment, the present invention provides a mutant FGF-21 peptide conjugate comprising the following glycosyl linking group:

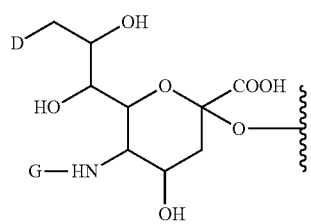

wherein D is a member selected from —OH and $R^1$-L-HN—; G is a member selected from H and $R^1$-L- and —C(O)($C_1$-$C_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is and when G is —C(O)($C_1$-$C_6$)alkyl, D is $R^1$-L-NH—.

The invention provides a peptide conjugate that includes a glycosyl linking group having the formula:

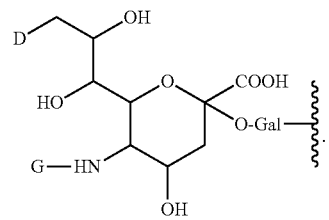

In other embodiments, the glycosyl linking group has the formula:

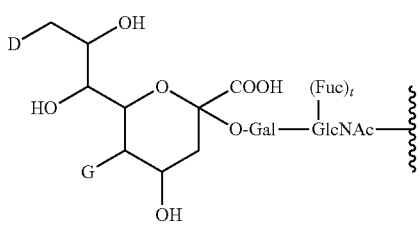

in which the index t is 0 or 1.

In a still further exemplary embodiment, the glycosyl linking group has the formula:

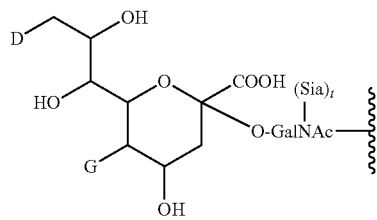

in which the index t is 0 or 1.

In yet another embodiment, the glycosyl linking group has the formula:

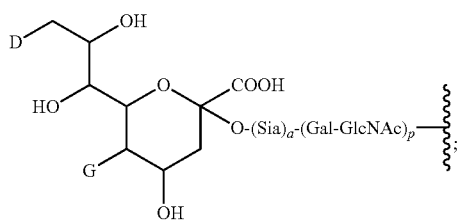

in which the index p represents and integer from 1 to 10; and a is either 0 or 1.

In an exemplary embodiment, a glycoPEGylated peptide conjugate is selected from the formulae set forth below:

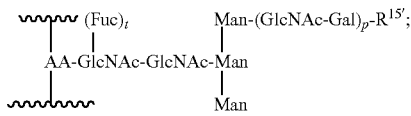

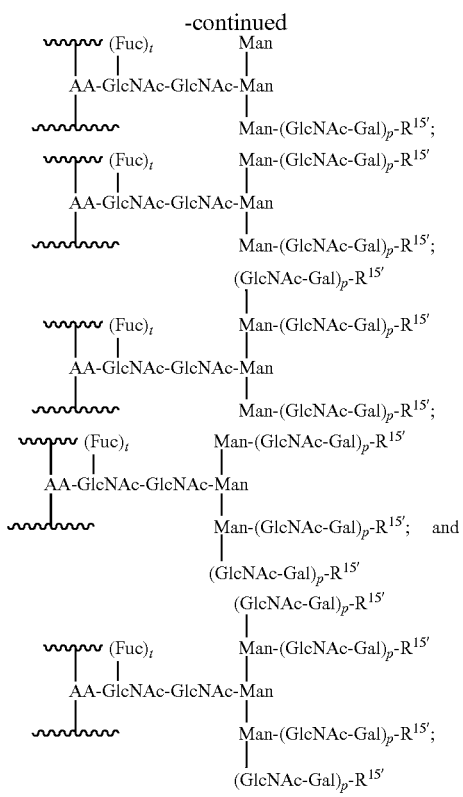

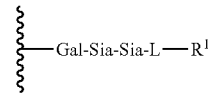

An exemplary species according to this motif is prepared by conjugating Sia-L-R¹ to a terminal sialic acid of a glycan using an enzyme that forms Sia-Sia bonds, e.g., CST-11, ST8Sia-II, ST8Sia-III and ST8Sia-IV.

In another exemplary embodiment, the glycans on the peptide conjugates have a formula that is selected from the group:

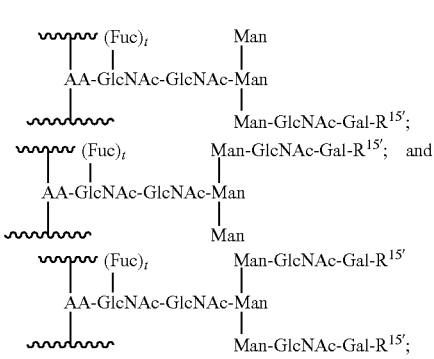

and combinations thereof.

In each of the formulae above, $R^{15'}$ is as discussed above. Moreover, an exemplary mutant FGF-21 peptide conjugate described herein will include at least one glycan with an IC moiety having a structure according to Formulae I or II.

In another exemplary embodiment, the glycosyl linking group comprises at least one glycosyl linking group having the formula:

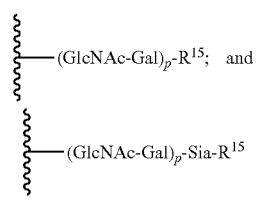

wherein $R^{15}$ is said sialyl linking group; and the index p is an integer selected from 1 to 10.

In an exemplary embodiment, the glycosyl linking moiety has the formula:

In the formulae above, the index t is an integer from 0 to 1 and the index p is an integer from 1 to 10. The symbol $R^{15'}$ represents H, OH (e.g., Gal-OH), a sialyl moiety, a sialyl linking group (i.e., sialyl linking group-polymeric modifying group (Sia-L-R'), or a sialyl moiety to which is bound a polymer modified sialyl moiety (e.g., Sia-Sia-L-R') ("Sia-SiaP")). Exemplary polymer modified saccharyl moieties have a structure according to Formulae I and II. An exemplary peptide conjugate of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3- to the galactose residue. In another exemplary embodiment, the sialic acid is linked α2,6- to the galactose residue.

In an exemplary embodiment, the sialyl linking group is a sialyl moiety to which is bound a polymer modified sialyl moiety (e.g., Sia-Sia-L-R¹) ("Sia-SiaP"). Here, the glycosyl linking group is linked to a galactosyl moiety through a sialyl moiety:

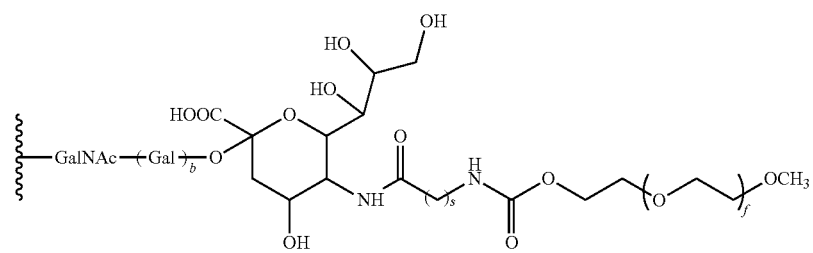

in which b is an integer from 0 to 1. The index s represents an integer from 1 to 10; and the index f represents an integer from 1 to 2500.

In an exemplary embodiment, the polymeric modifying group is PEG. In another exemplary embodiment, the PEG moiety has a molecular weight of 20-30 kDa. In exemplary embodiments, the PEG moiety has a molecular weight of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa. In another exemplary embodiment, the PEG moiety has a molecular weight of 20 kDa. In another exemplary embodiment, the PEG moiety has a molecular weight of 30 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In an exemplary embodiment, the glycosyl linking group is a linear 10 kDa-PEG-sialyl, and one or two of these glycosyl linking groups are covalently attached to the peptide. In an exemplary embodiment, the glycosyl linking group is a linear 20 kDa-PEG-sialyl, and one or two of these glycosyl linking groups are covalently attached to the peptide. In an exemplary embodiment, the glycosyl linking group is a linear 30 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide.

In a still further exemplary embodiment, a mutant FGF-21 peptide is pegylated in accordance with methods described herein. In a particular embodiment, the mutant FGF-21 peptide comprises the mutations $S^{173}T$ and $R^{176}A$, wherein the positions of the amino acids S and R are based on the amino acid sequence as depicted in SEQ ID NO: 1. More particularly, the mutant FGF-21 peptide comprises the amino acid sequence as depicted in SEQ ID NO: 2. As detailed herein above, the at least one glycosyl moiety attached to the threonine residue and linking the newly introduced threonine residue to the PEG moiety may virtually be any possible glycosyl moiety. The only limitation is that it should be able to attach to threonine and that it should be able to be attached to PEG or m-PEG, more particularly via a linker, e.g. an amino acid residue, particularly glycine. In particular embodiment, the at least one glycosyl moiety comprises N-acetylgalactosamine (GalNAc), galactose (Gal) and/or sialic acid (Sia). In a more particular embodiment, the at least one glycosyl moiety comprises the structure -GalNAc-Sia-, i.e. two glycosyl moieties, namely GalNAc and Sia, wherein the PEG residue may be attached to GalNAc or Sia, particularly to Sia. The glycosyl moiety which is not attached to the PEG moiety may be attached to the newly introduced threonine residue.

In another particular embodiment, the 20 kDa PEG moiety is attached to the at least one glycosyl linker via a linker, e.g. an amino acid residue, particularly a small amino acid, such as alanine or glycine, more particularly via glycine (Gly). Hence, the PEG or m-PEG moiety is attached to the amino acid and the amino acid is attached to a glycosyl moiety, such as Sia. The glycosyl moiety is attached to the amino acid linker, if present, and to the newly introduced threonine residue in the mutant FGF-21 amino acid sequence. The amino acid residue is attached to PEG and the glycosyl residue via a method described in WO 03/031464 which is incorporated herein by reference.

In a particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa.

In a more particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 21 kDa, 22 kDa, 23 kDa, 24 kDa, 25 kDa, 26 kDa, 27 kDa, 28 kDa, 29 kDa, or 30 kDa.

In a still more particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 25 kDa, or 30 kDa.

In a further particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa or 30 kDa.

In a still further particular embodiment, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa.

Figure 1:
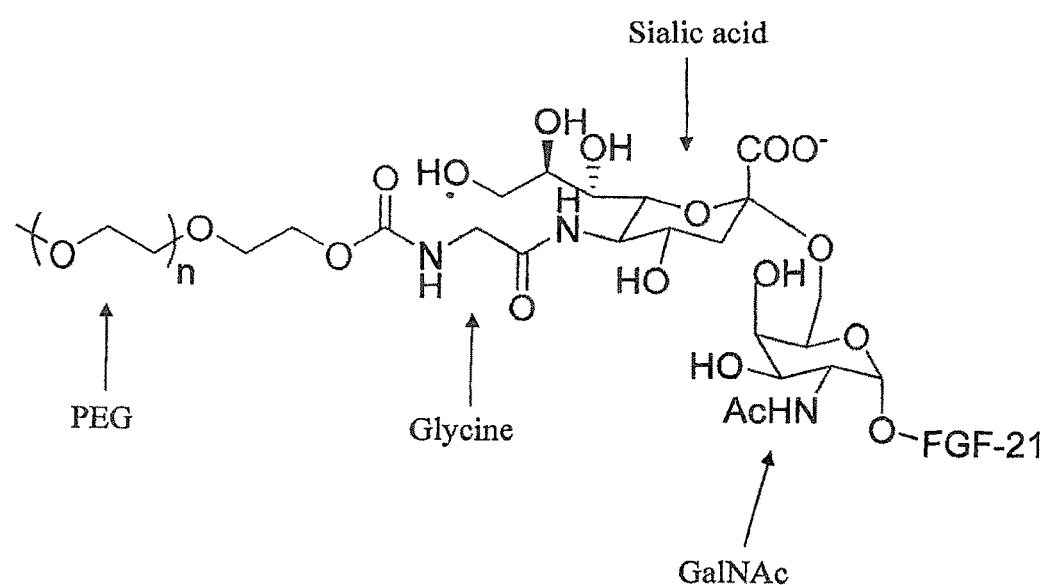
FIG. 1: Structure of a particular embodiment of the invention, namely of a mutant FGF-21 peptide conjugate comprising an exemplary structure of FGF-21(Thr)-GalNAc-Sia-Gly-PEG. n is chosen to give the desired molecular weight of PEG. With respect to 20 kDa PEG, n is in the range of selected from 450 to 460.

In a very particular embodiment, the mutant FGF-21 peptide conjugate comprises the structure:

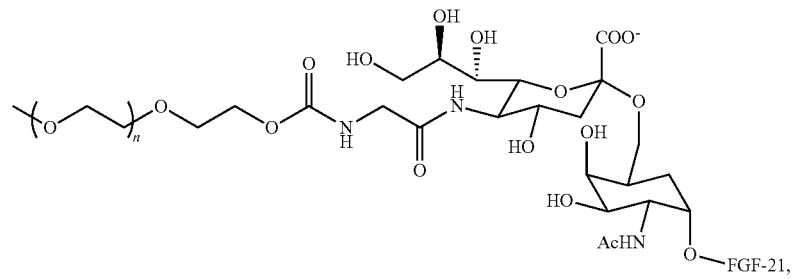

wherein n is an integer selected from 450 to 460 as also depicted in FIG. 1.

The 20 kDa PEG may be linear or branched, more particularly the 20 kDa PEG, is a linear 20 kDa PEG. Further, the 20 kDa PEG is particularly a 20 kDa methoxy-PEG (mPEG, m-PEG). PEG and mPEG of different molecular weight can be obtained from various suppliers, such as from JenKem Technology USA, Plano, Tex., USA, or Merckle Biotec, Ulm, Germany. It is understood in the art that PEG 20 kDa means that the size of the PEG residues is 20 kDa in average and that the majority of the PEG residues are 20 kDa in size.

Mutant FGF-21 Peptides and Conjugates Thereof

As described herein, the present inventors have made variants of Fibroblast Growth Factor-21 (FGF-21) having surprising properties, including variants having exceptionally long half-lives, which variants are peptide conjugates comprising i) a mutant FGF-21 peptide comprising at least one threonine (T) residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and ii) a 20-30 kDa polyethylene glycol (PEG), wherein said 20-30 kDa PEG is covalently attached to said mutant FGF-21 peptide at the at least one threonine residue via at least one glycosyl moiety.

For the attachment of the 20-30 kDa PEG residue, a threonine residue is introduced into the amino acid sequence of native FGF-21 adjacent to and on the C-terminal side of a proline residue which is already present in the amino acid sequence of native FGF-21, i.e. is a native proline residue. For this purpose, either (i) an additional threonine may be introduced immediately next to the native proline residue or (ii) the native amino acid which is present in the native amino acid sequence of FGF-21 adjacent to and located on the C-terminal side of a native proline residue is exchanged for a threonine residue. In the present invention, option (ii) is an exemplary embodiment. As described herein, more than one threonine residue may be introduced adjacent and C-terminal to a proline residue which is already present. A mutant FGF-21 of the present invention may thus comprise both threonine residues which have been additionally introduced and threonine residues which have been introduced instead of a native amino acid.

By the introduction of a new threonine residue on the C-terminal side and adjacent to a proline residue, a consensus sequence for O-glycosylation enzyme is formed. Because proline residues are typically found on the surface of proteins (in, e.g., turns, kinks, and/or loops), a design that calls for O-glycosylation and PEGylation thereto using a PEG-glycosyl moiety in close proximity to a proline residue benefits from the relative accessibility of the target attachment site for the glycosyl transferase that transfers the glycosyl or glycol-PEG moiety and the potential to accommodate the conjugated glycosyl and/or PEG structure without disruption of protein structure.

For introduction of the threonine residues into the native amino acid sequence of FGF-21, routine techniques in the field of recombinant genetics are used. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Ausubel et al., eds., Current Protocols in Molecular Biology (1994).

In a particular embodiment, the native FGF-21 amino acid sequence corresponds to the native amino acid sequence of human FGF-21 depicted in SEQ ID NO: 1.

In a particular embodiment, the mutant FGF-21 peptide comprises the amino acid sequence PT, i.e. a threonine residue C-terminally adjacent to a proline residue. The sequence PT is not present in the native FGF-21 amino acid sequence.

Optionally, the mutant FGF-21 peptide comprises at least one amino acid sequence selected from the group consisting of $P^{172}T$ (e.g. SEQ ID NO: 2 or 3), $P^{156}T$ (e.g. SEQ ID NO: 4), $P^{5}T$ (e.g. SEQ ID NO: 5), $P^{3}T$ (e.g. SEQ ID NO: 6), $P^{9}T$ (e.g. SEQ ID NO: 7), $P^{50}T$ (e.g. SEQ ID NO: 8), $P^{61}T$ (e.g. SEQ ID NO: 9), $P^{79}T$ (e.g. SEQ ID NO: 10), $P^{91}T$ (e.g. SEQ ID NO: 11), $P^{116}T$ (e.g. SEQ ID NO: 12), $P^{120}T$ (e.g. SEQ ID NO: 13), $P^{125}T$ (e.g. SEQ ID NO: 14), $P^{129}T$ (e.g. SEQ ID NO: 15), $P^{131}T$ (e.g. SEQ ID NO: 16), $P^{134}T$ (e.g. SEQ ID NO: 17), $P^{139}T$ (e.g. SEQ ID NO: 18), $P^{141}T$ (e.g. SEQ ID NO: 19), $P^{144}T$ (e.g. SEQ ID NO: 20), $P^{145}T$ (e.g. SEQ ID NO: 21), $P^{148}T$ (e.g. SEQ ID NO: 22), $P^{150}T$ (e.g. SEQ ID NO: 23), $P^{151}T$ (e.g. SEQ ID NO: 24), $P^{158}T$ (e.g. SEQ ID NO: 25), $P^{159}T$ (e.g. SEQ ID NO: 26), $P^{166}T$ (e.g. SEQ ID NO: 27), $P^{178}T$ (e.g. SEQ ID NO: 28), and combinations thereof, wherein the positions of proline and threonine are based on the native amino acid sequence of FGF-21 as depicted in SEQ ID NO: 1, particularly the mutant FGF-21 peptide comprises at least one amino acid sequence selected from the group consisting of $P^{172}T$, $P^{156}T$, $P^{5}T$ and combinations thereof, more particularly consisting of $P^{172}T$, $P^{156}T$ and combinations thereof, and even more particularly the mutant FGF-21 peptide comprises the sequence motif $P^{172}T$, based on the amino acid sequence as depicted in SEQ ID NO: 1, wherein the positions of proline and threonine are based on the amino acid sequence as depicted in SEQ ID NO: 1.

In a particular embodiment, the proline residue is located between amino acid 145 and the C-terminus of the mutant FGF-21 peptide, wherein the position of amino acid 145 is based on the amino acid sequence as depicted in SEQ ID NO: 1. As demonstrated by results presented herein, the C-terminus of FGF-21 surprisingly tolerates attachment of PEG and in particular of glycosyl-PEG moieties. This was unexpected since the literature reports that the intact C-terminus is necessary for β-Klotho binding of FGF-21.

In a particular embodiment, the mutant FGF-21 peptide comprises the mutations $S^{173}T$ and $R^{176}A$, wherein the positions of the amino acids S and R are based on the amino acid sequence as depicted in SEQ ID NO: 1, particularly the mutant FGF-21 peptide comprises the amino acid sequence as depicted in SEQ ID NO: 2. The mutation $R^{176}A$ has been found beneficial to the protein's overall stability after introducing the O-linked glycosylation site at threonine 173. By this mutation, the relatively large arginine side chain was removed and replaced by the small side chain of alanine. It is assumed that the smaller side chain of alanine interferes less with the voluminous glycosyl-PEG moiety to be attached to thindicae mutated FGF-21 peptide.

In an alternative embodiment, the mutant FGF-21 peptide comprises the mutation $Q^{157}T$, wherein the position of the amino acid Q is based on the amino acid sequence as depicted in SEQ ID NO: 1, particularly the mutant FGF-21 peptide comprises the amino acid sequence as depicted in SEQ ID NO: 4, or the mutation $D^{6}T$, wherein the position of the amino acid D is based on the amino acid sequence as depicted in SEQ ID NO: 1, particularly the mutant FGF-21 peptide comprises the amino acid sequence as depicted in SEQ ID NO: 5.

In a particular embodiment, the mutant FGF-21 peptide conjugate comprises an amino acid sequence selected from the group consisting of SEQ ID NOs: 2 to 28, more particularly an amino acid sequence selected from the group consisting of SEQ ID NOs: 2 to 5, even more particularly an amino acid sequence selected from the group consisting of SEQ ID NOs: 2 to 4, and most particularly the mutant FGF-21 peptide comprises the amino acid sequence as depicted in SEQ ID NO: 2.

Further provided is a pharmaceutical composition comprising the mutant FGF-21 peptide conjugate and a pharmaceutically acceptable carrier, such as water or a physiologically compatible buffer. The pharmaceutical composition typically comprises a therapeutically effective or pharmaceutically active amount of the mutant FGF-21 peptide conjugate as active agent.

Pharmaceutical compositions of the invention are suitable for use in a variety of drug delivery systems. Suitable formulations for use in the present invention are found in Remington's Pharmaceutical Sciences, Mack Publishing Company, Philadelphia, Pa., $17^{th}$ ed. (1985). For a brief review of methods for drug delivery, see, Langer, Science 249: 1527-1533 (1990). The pharmaceutical compositions are intended for parenteral, intranasal, topical, oral, or local administration, such as by subcutaneous injection, aerosol inhalation, or transdermal adsorption, for prophylactic and/or therapeutic treatment. Commonly, the pharmaceutical compositions are administered parenterally, e.g., subcutaneously or intravenously. Thus, the invention provides compositions for parenteral administration which comprise the mutant FGF-21 peptide conjugate dissolved or suspended in an acceptable carrier, particularly an aqueous carrier, e.g., water, buffered water, saline, phosphate buffered saline (PBS) and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

The pharmaceutical compositions of the invention may be sterilized by conventional sterilization techniques, or may be sterile filtered. The resulting aqueous solutions may be packaged for use as is, or lyophilized, the lyophilized preparation being combined with a sterile aqueous carrier prior to administration. The compositions containing the FGF peptide conjugates can be administered for prophylactic and/or therapeutic treatments, in particular for the treatment of diabetes or diabetes related diseases, particularly for the treatment of diabetes type 2, NASH and metabolic syndrome. In therapeutic applications, compositions are administered to a subject already suffering from a disease or condition related to diabetes, in an amount sufficient to cure or at least partially arrest the symptoms of the disease and its complications. An amount adequate to accomplish this is defined as a "therapeutically effective amount" and usually depends the patient's state of health and weight. Efficacious doses range from 0.1 mg/kg to 6 mg/kg when tested in various animal models of NASH and type 2 diabetes.

The present invention provides methods for treating a disease and/or a disorder or symptoms thereof which comprise administering a therapeutically effective amount of a compound (a mutant FGF-21 peptide conjugate described herein) or a pharmaceutical composition comprising same to a subject (e.g., a mammal such as a human). Thus, one embodiment is a method for treating a subject suffering from diabetes or a diabetes related disease (e.g., diabetes type 2, NASH or metabolic syndrome) or a symptom thereof. The method includes the step of administering to the mammal an amount of a compound described herein in an amount sufficient to treat the disease or disorder or symptom thereof or a composition comprising same, under conditions such that the disease or disorder is treated.

Single or multiple administrations of the compositions can be carried out with dose levels and pattern being selected by the treating physician. In any event, the pharmaceutical compositions should provide a quantity of the mutant FGF-21 peptide conjugate of this invention sufficient for an effective treatment of the subject in need of such treatment.

In the pharmaceutical composition, the mutant FGF-21 peptide conjugate is typically present in a concentration in the range from 0.1 mg/mL to 50 mg/mL, particularly from 1 mg/mL to 45 mg/mL, more particularly from 10 mg/mL to 40 mg/mL, most particularly in a concentration of 26±4 mg/mL. In a more particular embodiment, the concentration of the mutant FGF-21 peptide conjugate in a pharmaceutical composition is 33±7 mg/mL or even more particularly 26±4 mg/mL.

All components of the pharmaceutical composition as well as the specific concentrations of the components have carefully selected after testing very many different conditions, compounds and concentrations thereof. Hence, the pharmaceutical composition disclosed herein is not an arbitrary selection of compounds and compound concentrations but a specific and rational selection of conditions which have been found to be most optimal for an aqueous pharmaceutical composition containing the mutant FGF-21 peptide conjugate or mutant FGF-21 peptide according to the invention for use as a medicament.

Further, the pharmaceutical composition particularly comprises a buffering agent, particularly a phosphate or Tris buffer, more particularly a Tris buffer, e.g. Tris(hydroxymethyl)aminomethane (THAM). Optionally, the buffering agent is present in a concentration from 1 mM to 100 mM, particularly from 2 mM to 75 mM, more particularly from 5 mM to 50 mM, even more particularly from 10 mM to 25 mM, most particularly of 16±2 mM. Tris buffer was selected since solubility of the protein was found to be better than for other buffer systems and it is suitable to keep the pH at pH 7.5. This pH seems the most optimal one for prolonged storage of the PEGylated mutant FGF-21 peptide conjugate. Moreover, probability of Tris cristallization at lower temperatures is lower than that of phosphate based buffering agents.

It was found by the inventor that the mutant FGF-21 peptide conjugate may undergo precipitation of the pH is below 6.0. Optionally, the pH of the pharmaceutical composition is in the range from 6.0 to 8.5, particularly from 6.5 to 8.0, more particularly from 6.75 to 8.0, even more particularly from 7.0 to 8.0, and most particularly is 7.5±0.3 as lowest fragmentation in SDS-PAGE and least aggregation in SEC was observed if the pH is in the range of 7-8. This pH has also been identified to be optional with respect to viscosity. As the pH of a solution may depend on the temperature of the solution, the pH should particularly be adapted and measured at 25±2° C. The pH is adjusted with HCl. The pharmaceutical composition may further comprise a salt, particularly an inorganic salt, more particularly NaCl. Optionally, the salt is present in a concentration from 30 mM to 200 mM, particularly from 40 mM to 150 mM, more particularly from 50 mM to 100 mM, most particularly of 56±2 mM.

The presence of a salt, particularly NaCl, is beneficial to reduce viscosity which is increased in PEG containing samples. For the same reason, it is also beneficial to include sorbitol and/or glycine.

The pharmaceutical composition may further comprise a tonicity modifying agent. The tonicity modifying agent may be selected from the group consisting of glycerol, amino acids, sodium chloride, proteins, sugars and sugar alcohols. In a particular embodiment, the tonicity modifying agent is a sugar, more particularly the tonicity modifying agent is sucrose. A tonicity modifying agent, in particular sucrose, was found to have an advantageous effect on the pharmaceutical composition as it reduces aggregation of the active agent, namely the mutant FGF-21 peptide (conjugate).

The tonicity modifying agent, particularly sucrose, may be present in a concentration of 50 mM to 200 mM, more particularly in a concentration of 100 mM to 175 mM, even more particularly in a concentration of 135 mM to 160 mM, and most particularly in a concentration of 150±2 mM.

Further, the pharmaceutical composition may comprise a surfactant, particularly a non-ionic surfactant. The surfactant or non-ionic surfactant particularly is a polysorbate-based non-ionic surfactant, more particularly polysorbate 20 or polysorbate 80, and even more particularly polysorbate 20. A surfactant, in particular polysorbate 20, was found to reduce sub-visible particles below 10 µm and thus seems to have a stabilizing effect on the pharmaceutical composition.

The surfactant or non-ionic surfactant, particularly polysorbate 20 or 80, more particularly polysorbate 20, is optionally present in a concentration of 0.01 mg/mL to 1 mg/mL, particularly in a concentration of 0.05 to 0.5 mg/mL and most particularly in a concentration of 0.2±0.02 mg/mL. Polysorbate 20 or 80, particularly polysorbate 20, were found to stabilize the formulation to aggregation.

In a particular embodiment, a pharmaceutical composition comprises 0.1 to 50 mg/mL, particularly 33±7 mg/mL of mutant FGF-21 peptide conjugate; 1 mM to 100 mM, particularly 20±2 mM, buffering agent, particularly a Tris buffer; 30 mM to 200 mM, particularly 70±2 mM, salt, particularly NaCl; and has a pH of 7.5±0.3 (particularly measured at 25±2° C.

A more particular pharmaceutical composition comprises 0.1 to 50 mg/mL, particularly 26±4 mg/mL of mutant FGF-21 peptide conjugate; 1 mM to 100 mM, particularly 16±2 mM, buffering agent, particularly a Tris buffer; 30 mM to 200 mM mM, particularly 56±2 mM, salt, particularly NaCl; 50 mM-200 mM tonicity modifying agent, particularly sucrose; and 0.01 to 1 mg/mL, particularly 0.2±0.02 mg/mL, surfactant or non-ionic surfactant, particularly polysorbate 20; and has a pH of 7.5±0.3 (particularly measured at 25±2° C.

Also provided herein is a pharmaceutical container comprising the mutant FGF-21 peptide conjugate of the invention and as described herein or the pharmaceutical composition of the invention and as described herein. In a particular embodiment, the pharmaceutical container is a syringe, vial, infusion bottle, ampoule, carpoule, a syringe equipped with a needle protection system, or a carpoule within an injection pen.

The present invention further provides a method of producing the mutant FGF-21 peptide conjugate of the invention, comprising the steps of:
  (1) recombinantly producing the mutant FGF-21 peptide, particularly in an expression host; and
  (2) enzymatically attaching to the mutant FGF-21 peptide of step (1) a PEG-glycosyl moiety, wherein the PEG is, for example, a 20 kDa PEG or a 30 kDa PEG, and wherein step (2) is particularly a cell free, in vitro process, thereby forming the mutant FGF-21 peptide conjugate.

In a particular embodiment, the method is as follows: First the mutation which introduces the threonine adjacent to and on the C-terminal side of a proline residue and optionally one or more further mutations are introduced into a nucleic acid sequence encoding for native or mutated FGF-21, such as of human FGF-21 as in SEQ ID NO: 1. The nucleic acid sequence encoding the mutated FGF-21 peptide is the introduced into an expression vector suitable for protein expression in an expression host. Methods for introducing mutations into nucleic acid sequences, such as site-directed mutagenesis, and the incorporation of the mutated nucleic acid sequence into an expression vector are well known to the skilled person (cf. e.g., "A Guide to Methods in the Biomedical Sciences" by R. B. Corley, Springer Science & Business Media, 2006).

After protein expression, optional purification, the PEG residue is attached to the mutant FGF-21 peptide, specifically at the newly introduced threonine residue via at least one glycosyl moiety and optionally via at least one amino acid residue which is present between the PEG and the glycosyl residue.

To obtain high yield expression of a nucleic acid encoding a mutant FGF-21 of the present invention, one typically subclones a polynucleotide encoding the mutant Fibroblast Growth Factor into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al, supra. Bacterial expression systems for expressing the native or mutant FGF-21 are available in, e.g., *Escherichia coli* (*E. coli*), *Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector. In a particular embodiment, the mutant FGF-21 peptide is recombinantly produced in *E. coli* cells, i.e. the expression host is *E. coli*.

An exemplary method of production is described in this paragraph: The mutant FGF-21 peptide is expressed in *E. coli* as inclusion bodies. Cells are recovered from the harvest by centrifugation, disrupted, and inclusion bodies are washed and recovered by centrifugation. Purification of the non-PEGylated mutant FGF-21 peptide begins with solubilizing the mutant FGF-21 peptide from the inclusion bodies and refolding of the peptide. The refolded mutant FGF-21 peptide is filtered and purified by two anion exchange chromatography operations, both utilizing Eshmuno Q chromatography resin and operated in bind and elute mode. If necessary, the purified mutant FGF-21 peptide may be concentrated by ultrafiltration using Pellicon 2 (5 kD MWCO) membranes. The purified mutant FGF-21 peptide is dispensed into sterile PETG bottles and may be stored at ≤70° C.

Figure 3:
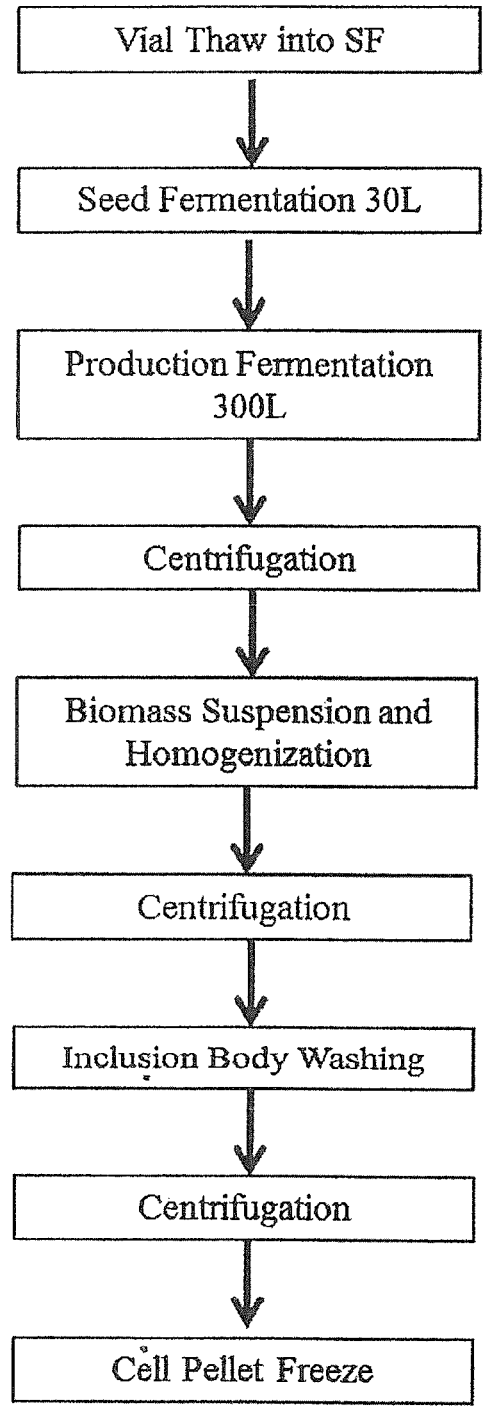
FIG. 3: Exemplary cell expansion, production, and harvest process flow diagram.
Figure 4:
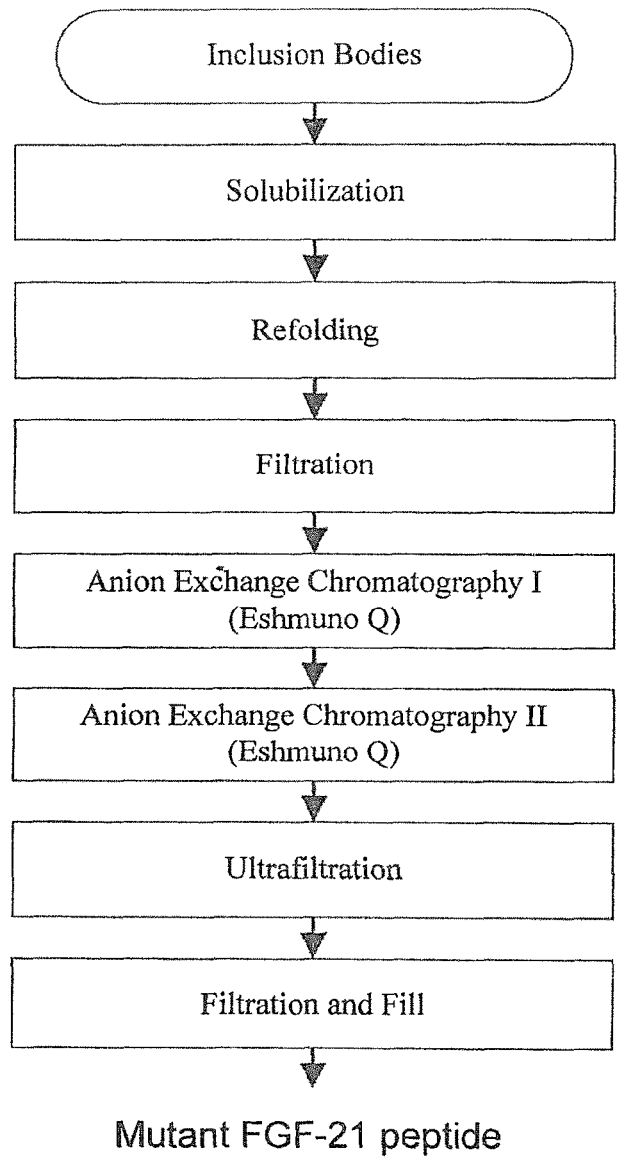
FIG. 4: Exemplary refolding and mutant FGF-21 peptide purification process flow diagram.
Figure 5:
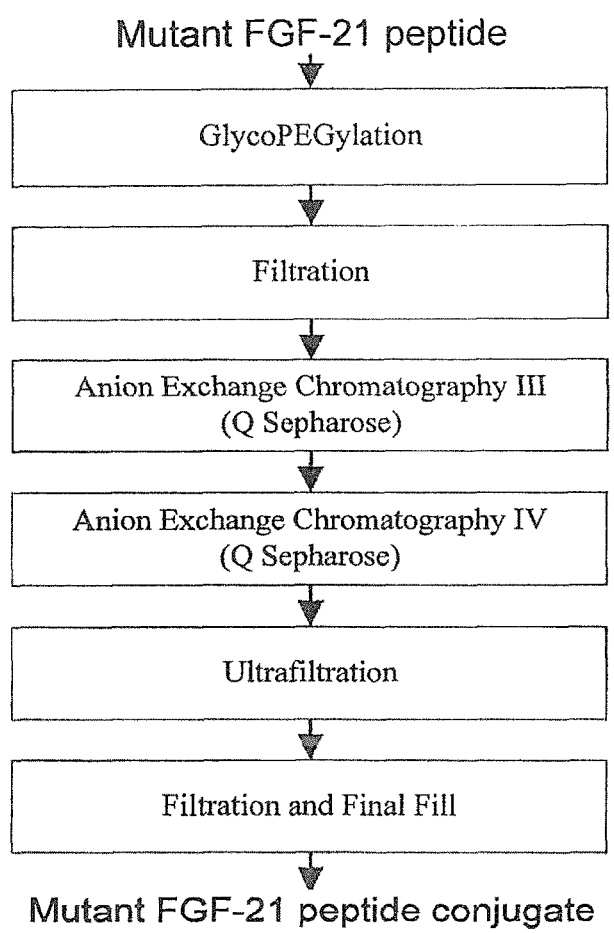
FIG. 5: Exemplary GlycoPEGylation and final purification process flow diagram.

GlycoPEGylation of mutant FGF-21 peptide may be performed by two enzymatic reactions performed in series or at the same time. This step may be followed by 0.2 µm filtration and two anion exchange chromatography operations, both utilizing Q Sepharose Fast Flow chromatography resin and operated in bind and elute mode. A final concentration step may be performed by ultrafiltration using Pellicon XL Biomax (10 kDa MWCO). FIGS. 3 to 5 illustrate an exemplary method of production.

Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., Curr. Opin. Chem. Biol. 2: 98-111 (1998). See also PCT Publication Nos: WO 2003/031464; WO 2005/089102; WO 2006/050247; and WO 2012/016984, the entire content of each of which is incorporated herein by reference.

In a particular embodiment, step (2) comprises a step (2a) of contacting the mutant FGF-21 peptide with a GalNAc donor and a GalNAc transferase under conditions suitable to transfer GalNAc from the GalNAc donor to the at least one threonine residue of the mutant FGF-21 peptide. Conditions for this transfer are described in the Example section. Optionally, the GalNAc donor is UDP-GalNAc and, particularly, the GalNAc transferase is MBP-GalNAcT2.

In a particular embodiment and more particularly in combination with the embodiment of the aforementioned paragraph, step (2) further comprises, particularly in combination with step (2a), a step (2b) of contacting the product of step (2a), if present, or of step (1), with, e.g., a 20 kDa PEG-Sia donor or 30 kDa PEG-Sia donor and a sialyltransferase under conditions suitable to transfer 20 kDa PEG-Sia from the 20 kDa PEG-Sia donor or the 30 kDa PEG-Sia from the 30 kDa PEG-Sia donor to the at least one threonine residue of the mutant FGF-21 peptide, if step (2a) is not present, or to the GalNAc at the mutant FGF-21 peptide, if step (2a) is present. Optionally, the 20 kDa PEG-Sia donor is 20 kDa PEG-Sia-CMP or the 30 kDa PEG-Sia donor is 30 kDa PEG-Sia-CMP and/or the sialyltransferase is ST6GalNAc1. As already explained in general above, the term "20 kDa PEG-Sia" also includes "20 kDa PEG-linker-Sia" and "20 kDa PEG-Gly-Sia" and the term "30 kDa PEG-Sia" also includes "30 kDa PEG-linker-Sia" and "30 kDa PEG-Gly-Sia".

In a more particular embodiment, the 20 kDa PEG-Sia donor comprises the structure Hence, optionally, the method further comprises a step (3), after step (1) and prior to step (2), of purifying the mutant FGF-21 peptide after recombinant production. Further, the method may comprise a step (4), after step (2), of purifying the mutant FGF-21 peptide conjugate formed in step (2).

The purification step (3) and/or (4) may comprise subjecting the mutant FGF-21 peptide to a method selected from the group consisting of ion exchange chromatography, affinity chromatography, filtration and combinations thereof. Step (3) and/or step (4) may comprise one or more steps of ion exchange chromatography, affinity chromatography, filtration or combinations thereof.

Step (3) and/or step (4) may particularly comprise subjecting the mutant FGF-21 peptide to one or more steps of ion exchange chromatography, more particularly to at least two steps of ion exchange chromatography, even more particularly anion exchange chromatography. In a more particular embodiment, the mutant FGF-21 peptide is subjected to two anion exchange chromatography steps, more particularly to two strong anion exchange chromatography steps in step (3) and in step (4).

The anion exchange chromatography particularly employs a member selected from the group consisting of a hydrophilic polyvinyl ether base matrix, diethylaminoethanol (DEAE), trimethylammoniumethyl (TEAE), agarose, polystyrene/divinyl benzene polymer matrix, a quaternary ammonium (Q) strong anion exchange chromatography and combinations thereof, even more particularly in step (3) two columns using a hydrophilic polyvinyl ether base matrix are used, highly particularly in step (3) two Eshmuno®-Q columns are used. Eshmuno®-Q resins having a hydrophilic polyvinyl ether base matrix are e.g. available from Merck Millipore, Merck KGaA, Darmstadt, Germany. Source 15Q resins are also of use in the present invention (GE Health Care Life Sciences, Chalfont St Giles, UK). The affinity chromatography may be an anionic anthraquinone dye affinity chromatography and filtration may employ a modified hydrophilic polyethersulfone (PES) membrane. In another embodiment, two weak anion exchange chromatography steps are performed or one strong and one weak anion exchange chromatography step.

In an alternative embodiment, the purification in step (3) is performed as below, optionally in the given order:

1. ion exchange chromatography, particularly anion exchange chromatography,

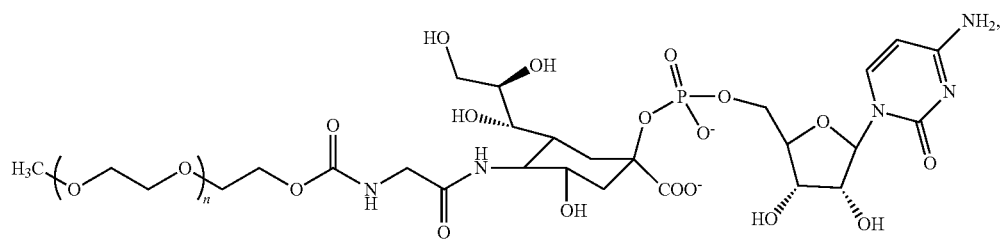

wherein n is an integer selected from 450 to 460, which results in a molecular weight of 20 kDa. This structure includes a Gly linker. The skilled person understands that methods for producing the same are described in PCT Publication No. WO 2003/031464, the entire content of which is incorporated herein by reference.

After expression and before the glycoPEGylation reaction, it is desirable to purify the mutant FGF-21 peptide.

2. optionally affinity chromatography, 3. optionally ion exchange chromatography, particularly anion exchange chromatography, and 3. filtration.

Exemplary purification is performed in the Example section. In general, the chromatography purification steps are to be performed according to the manufacturer's protocols.

Further information can e.g. be taken from "Protein Purification Protocols", Paul Cutler, Springer Science & Business Media, 2004).

In an optional embodiment, the method further comprises a step (4), after step (2), of purifying the mutant FGF-21 peptide conjugate formed in step (2), particularly by ion exchange chromatography, more particularly by strong anion exchange chromatography, even more particularly by quaternary ammonium (Q) strong anion exchange chromatography. In a particular embodiment, two anion exchange chromatography steps are performed in step (4). Q-sepharose is a more particular column material suitable for purifying the mutant FGF-21 peptide conjugate of the present invention in step (4). Q sepharose is e.g. available from GE Healthcare Life Sciences, Chicago, Ill., USA.

In a particular embodiment, arginine is added in steps (2) and (3), particularly at least 400 mM arginine. Arginine is optionally added to inhibit proteases which would otherwise degrade the protein. Hence, arginine helps to prevent protein loss.

Finally, endotoxin is removed which may originate from the expression host in an optional step (5), after step (3) and prior to step (2). In this step, the product of step (3) is filtered using an endotoxin removal filter, such as Mustang E, 0.2 micron filter.

Further, the mutant FGF-21 peptide conjugate may be sterile filtered.

Also provided are the mutant FGF-21 peptide conjugates obtainable by the method of the invention.

The present invention also provides the mutant FGF-21 peptide conjugate of the invention and/or the pharmaceutical composition of the invention for use as a medicament and for use in the treatment of diabetes and related diseases, particularly diabetes type 2, non-alcoholic steatohepatitis (NASH) and/or metabolic syndrome. The invention also provides the use of the mutant FGF-21 peptide conjugate of the invention and/or the use of the pharmaceutical composition of the invention for the treatment of diabetes and related diseases, particularly diabetes type 2, NASH and/or metabolic syndrome.

Further provided is a method of treating diabetes and related diseases, particularly diabetes type 2, NASH, non-alcoholic fatty liver disease (NAFLD), and/or metabolic syndrome comprising administering to a subject in need thereof an amount of the mutant FGF-21 peptide conjugate according to the invention or the pharmaceutical composition according to the invention. In a particular embodiment, the subject is a human subject.

NAFLD is a common chronic liver disease in Western countries, which can progress to cirrhosis and is associated with an increased mortality risk in general and an increased cardiovascular disease mortality risk in particular. Current pharmacological treatment of NAFLD has limited efficacy and therefore, there is a pressing need to develop more effective and safe agents for this common and life-threatening disease. Obeticholic acid (OCA), a selective agonist of the farnesoid X receptors, appears to have promise as a therapeutic agent for the management of NAFLD. The Farnesoid X Receptor Ligand Obeticholic Acid in NASH Treatment (FLINT) trial in patients with NASH, revealed that OCA administration is associated with improvements in liver histology, as well as weight loss and reduction in blood pressure. Although its adverse effects on lipid profile and insulin sensitivity are noteworthy, OCA might be considered in selected patients with NAFLD/NASH, particularly those with adequately controlled glucose and lipid levels.

With respect to indicators demonstrating clinical efficacy of compounds and compositions described herein, a variety of exemplary indicators are known in the art and described herein including, without limitation, a reduction in HbA1c, glucose and Insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein. See, for example, FIGS. 8-20 and descriptions thereof. Accordingly, a change (as indicated above) in at least one of the indicators reflects clinical efficacy of a compound or composition described herein.

In a particular embodiment, the therapeutic efficacy of a compound or composition described herein is determined based on a reduction in at least one of serum triglyceride levels or serum insulin levels. See, for example, Table 5.

HOMA-IR is, for example, is an indicator of the presence and extent of insulin resistance in a subject. It is an accurate indicator of the dynamic between baseline (fasting) blood sugar and insulin levels responsive thereto. It is referred to as an insulin resistance calculator. For humans, a healthy range is 1.0 (0.5-1.4). Less than 1.0 indicates that a subject is insulin-sensitive, which is ideal; above 1.9 indicates that a subject is exhibiting early insulin resistance; above 2.9 indicates that a subject is exhibiting significant insulin resistance. HOMA-IR blood code calculation is determined as follows: insulin uIU/mL (mU/L) X glucose (mg/dL)=HOMA-IR. The calculation requires U.S. standard units. To convert from international SI units: for insulin: pmol/L to uIU/mL, divide (±) by 6; for glucose: mmol/L to mg/dL, multiply (X) by 8.

Also presented herein are therapeutic regimen, whereby a therapeutically effective amount of a mutant FGF-21 peptide conjugate described herein or a pharmaceutical composition comprising a therapeutically effective amount of a mutant FGF-21 peptide conjugate is administered twice per day, once per day, every two days, three times per week, once per week, once every two weeks, once every three weeks, or once per month. Long duration efficacy of mutant FGF-21 peptide conjugates described herein is evidenced by the surprisingly long half-life determined for these conjugates in animal model systems. See, for example, Examples 11, 12, and 13 herein. Long duration efficacy of mutant FGF-21 peptide conjugates described herein, in turn, makes it possible to administer the mutant FGF-21 peptide conjugates less frequently. Accordingly, in a particular embodiment, a mutant FGF-21 peptide conjugate described herein or a composition comprising same is administered to a subject in need thereof at a frequency of equal to or greater than once per week. For example, the mutant FGF-21 peptide conjugate described herein or a composition comprising same may be administered to a subject in need thereof once every 7 days, once every 8 days, once every 9 days, once every 10 days, once every 11 days, once every 12 days, once every 13 days, once every 14 days, once every 15 days, once every 16 days, once every 17 days, once every 18 days, once every 19 days, once every 20 days, once every 21 days, once every 22 days, once every 22 days, once every 23 days, once every 24 days, once every 25 days, once every 26 days, once every 27 days, once every 28 days, once every 29 days, once every 30 days, or once every 31 days.

In another exemplary therapeutic regimen, compounds described herein and compositions comprising same are following a course of "induction" therapy, which calls for more frequent administration such as twice a week or weekly at the onset of the treatment regimen followed by maintenance therapy, which may involved bi-weekly or once a month administration. Such regimen are effective in that the initial induction therapy improves the subject's condition to a manageable level that is acceptable with regard to achieving a clinical state that is acceptable for maintenance of the disease/condition. Thereafter, the maintenance therapy is used to preserve the level of wellness at the maintenance level.

Therapeutic efficacy of a compound and/or composition for treating diabetes and related diseases, particularly diabetes type 2, non-alcoholic steatohepatitis (NASH) and/or metabolic syndrome may be evaluated using a variety of parameters and assays known by persons of skill in the art and described herein. Measuring HbA1C is considered a standard assay for measuring glycemic index of a subject over a long duration. It is, therefore, a stable indicator of glycemic index, reflecting glucose levels over the course of approximately the last 3-4 months. Accordingly, a subject who has diabetes (e.g., diabetes type 2) may be defined by the percent HbA1C determined in a suitable assay.

For a healthy person without diabetes, the normal range for the hemoglobin A1c level is between 4% and 5.6%. Hemoglobin A1c levels between 5.7% and 6.4% indicate that a person has a higher chance of developing diabetes. Levels of 6.5% or higher indicate that a person has diabetes.

In a particular embodiment, HbA1C is measured with HPLC by using the Glycated hemoglobin test system (BIO-RAD, Hercules, Calif., USA). Blood samples (e.g., 1.0 mL/per time) may be collected from the cephalic or saphenous vein into BD Vacutainer® K2-EDTA tubes. Samples may be stored immediately at 4 degrees C. or maintained on wet ice and analyzed on the same day the blood was collected. HbA1c levels in the blood may be measured by persons skilled in the art with HPLC by using the Glycated hemoglobin test system (BIO-RAD, Hercules, Calif., USA).

With regard to NASH, this condition is currently diagnosed only by biopsy. There are some serogate biomarkers however, that are considered predictive of NASH, such as liver fat (determined by MM), liver enzymes (ALT and ALT/AST ratio), and fibrosis biomarkers, such as pro-C3.

EXAMPLES

Example 1: Preparation of FGF-21 Mutants 1.1 Expression Vector and cDNA for FGF-21

The expression vector used for this project was designated pCWM3. The vector has the strong TAC promoter to drive expression with a GT10 translational enhancer. The sites selected for incorporation of the cDNA were NdeI and XhoI. A cDNA coding for the full length mature form of the human FGF21 gene was codon optimized for *E. coli* expression and synthesized by BlueHeron based on the published sequence (NCBI Accession # NM 019113). The gene was PCR amplified using 2 sets of oligonucleotides that would incorporate the desired mutations and restriction sites for constructing the expression vectors.

1.2 Overlapping PCR Reactions to Generate Mutant FGF-21 Constructs.

Oligonucleotide sequence with restriction sites underlined (NdeI and XhoI respectively).

5' oligo 5' GAGGTCATATGCATCCAATTCCAGATTC3' (second stage PCR, SEQ ID NO: 29).

3' oligo 5' ATTCCTCGAGTTATTAAGAGGCGTAG3' (second stage PCR, SEQ ID NO: 30).

The native human FGF-21 gene (5 µg) was supplied by BlueHeron in 200 µL of water (75 ng/µL).

| PCR Reaction | PCR Thermocycle Program |
|---|---|
| 0.2 µL DNA 15 ng | 1) 95° C. 5' |
| 4 µL 5' oligo 2.5 µM | 2) 95° C. 30" |
| 4 µL 3' oligo 2.5 µM | 3) 45° C. 30" |
| 2 µL 10× PCR buffer with MgCl$_2$ | 4) 72° C. 30" Return to 2) 5 times |
| 0.4 µL dNTPs 10 mM each | 5) 95° C. 30" |
| 0.4 µL Pfu Ultra 2.5 U/µl | 6) 50° C. 30" |
| 9 µL, H$_2$O | 7) 72° C. 30" Repeat to 5) 20 times |
| | 8) 72° C. 5' |

Mixture is assembled in sterile 0.2 mL thin walled PCR 96 well plates using sterile aerosol resistant pipet tips.

The PCR reactions (20 µL) were mixed with 5 µL of 6× loading dye in 96 well plates prior to loading agarose gel. A 1.5% agarose gel was subjected to electrophoresis at 100 V using a TAE buffer. A gel slice of the in gel PCR product was isolated and processed using the Qiaquick Gel extraction kit, following the manufacturer's instructions, and eluted with 50 µL of H$_2$O. To conserve space, the bands of each corresponding pair of the primary PCR products to be used in the second stage PCR to generate the full-length mutant were combined in the extraction well of the kit. Also mutants which were single step PCR reaction products were generated as described above for first stage PCR products.

The second step of the PCR reaction was carried out as follows:

| PCR Reaction | PCR Thermocycle Program |
|---|---|
| 10 µL DNA (from gel extraction) | 1) 95° C. 5' |
| 0.4 µL 5' oligo 25 µM | 2) 95° C. 30" |
| 0.4 µL 3' oligo 25 µM | 3) 45° C. 30" |
| 2 µL 10× PCR buffer with MgCl$_2$ | 4) 72° C. 30" Repeat to 2) 5 times |
| 0.4 µL dNTPs 10 mM each | 5) 95° C. 30" |
| 0.4 µL Pfu Ultra 2.5 U/µl | 6) 50° C. 30" |
| 3.6 µL H$_2$O | 7) 72° C. 30" Repeat to 5) 20 times |
| | 8) 72° C. 5' |

PCR products were purified by Qiaquick PCR purification kit and eluted with 50 µL of water according to the manufacturer's instructions. Restriction digests were performed in autoclaved 0.5 mL centrifuge tubes as follows on the purified PCR products and

| 14 µL DNA elution | 4 µL pCWM3 miniprep plasmid DNA |
|---|---|
| 2 µL 10× BSA | 2 µL 10× BSA |
| 2 µL NEB Buffer | 4 2 µL NEB Buffer 4 |
| 1 µL Nde 1 | 1 µL Nde 1 |
| 1 µL Xho1 | 1 µL Xho1 |
| | 10 µL water |

Reactions were incubated for 2 hrs at 37° C. Then 4 µL of 6×DNA loading buffer was added before loading a 1.5% agarose gel with SYBR Green and electrophoresed in TAE buffer for 60 minutes at 100 V.

A slice of the gel PCR product was isolated and processed with Qiaquick Gel extraction kit, following the manufacturer's instructions, and eluted with 50 µL of H₂O.

1.3 Ligation Reactions to Insert the Mutant FGF21 Genes into the Expression Vector pcMW3

Ligations were performed by combining the reagents listed below in autoclaved 0.5 mL eppendorf tubes:
- 0.2 µL pCWM3 (digested with Nde1 and Xho1 and agarose gel isolated)
- 1 µL PCR product (digested with Nde1 and Xho1 and agarose gel isolated)
- 1 µL 10×NEB ligase buffer
- 0.5 µL NEB T4 DNA ligase
- 7.3 µL water Incubate for 1 hr at room temperature.

1.4 Transform Competent TOP 10 E. coli with the Ligation Reaction.

Add 1 µL of each ligation reaction to 25 µL of thawed Top10 chemically competent cells in an autoclaved 1.5 µL microfuge tube. The cells were heat shocked by incubation at 42° C. for 1 minute. The cells were transferred to an ice bucket for 2 minutes. Next 175 µL of pre-warmed SOC were added and the tubes were incubated for 60 minutes at 37° C. on a rotating platform set at 250 rpm. Selection of transformants was accomplished on spreading the transformation reaction on Martone agar plates containing 50 mcg/mL of kanamycin sulfate. The plates were incubated overnight at 37° C. 3 colonies of each FGF21 mutant were restreaked onto two Martone agar-Kan50 plates with one being sent to Genewiz for colony amplification and sequencing. Correct sequences were identified for all 46 mutants.

Example 2: Miniprep DNA Preparation and Generation of Glycerol Stocks

The correct colony identified by sequencing was amplified overnight in 3 mL of Martone L broth supplemented with 50 mcg/ml Kanamycin sulfate. DNA was isolated from 1.5 mL of culture using Qiagen miniprep kit according to the manufacturers' instructions. Miniprep DNA was stored at -20° C. in 1.5 mL eppendorf tubes. 120 µL of culture were also frozen down with 80 µl of 50% glycerol solution to generate a 20% glycerol final concentration. The stocks were frozen at -80° C. in a 96 well plate.

Chemically competent Origami2 (25 µL) were transformed as described above with 1 µL of miniprep DNA from the constructs and selection of transformants was accomplished on Martone agar Kan50 plates also as described above. An overnight culture was grown from a scraping of several colonies into 2 mL of Martone L broth supplemented with 50 µg/mL kanamycin sulfate followed by growth overnight at 37° C. on a shaking platform set at 250 rpm. The following day, 120 µL of culture was mixed with 80 µL of 50% glycerol to generate a 20% glycerol final concentration. The glycerol stocks were frozen at -80° C. in a 96 well plate.

Example 3: Creation of FGF-21 Expressing Cell Lines

Plasmid DNA encoding FGF-21 (wild type, SEQ ID NO: 1) and each of the FGF-21 mutants was obtained from Teva (Petach Tikva, Israel). The preparation of the plasmid DNA using the pCWM3 vector is described in Example 1. All E. coli cell lines were prepared according to the following procedure. Chemically competent Origami-2 cells (Novagen) were thawed on ice and 10 µL of the cell suspension placed in an autoclaved 1.7 mL microfuge at 4° C. (ice). Plasmid DNA (1 µL) was diluted 1:10 with sterile water, added to the cells and then gently mixed by flicking the tube. The tube was left to incubate for 30 minutes while on ice. The microfuge tube was then placed into a water bath set at 42° C. and incubated for 45 seconds. The tube was then cooled on ice for two minutes. Three hundred microliters of SOC medium (TekNova, Hollister, Calif., USA) was then added to the tube and the tube incubated at 37° C. for one hour. This reaction mixture (100 µL) was then spread onto pre-warmed (37° C.) agar plates that contained 50 µg/mL of kanamycin sulfate. These agar plates were placed upside down in a 37° C. incubator and incubated for 16-24 hours. Plates were then parafilmed and stored at 4° C. Plates could be stored for several days using this method.

Three individual colonies from the agar plates were selected based on size and shape and inoculated (bactiloops) into 2 mL of LB-Broth (TekNova, Hollister, Calif., USA) containing 25 µg/mL of kanamycin sulfate. Inoculated tubes were incubated for 6-8 hrs in a shaker incubator set at 250 rpm of agitation and 37° C. Cells were then harvested by centrifuging (10,000×g for 2 minutes) an aliquot (50 µL) of the culture. The cell pellets were frozen and analyzed by SDS-PAGE analysis (designated as uninduced cell pellet). Glycerol stocks were created in a laminar flow hood by combining 200 µL of a 50% glycerol solution with 300 µL of cell culture in labeled sterile Nalgene cryovials. The vials were vortexed and stored at -80° C.

The remaining culture was transferred to a shaker incubator set at 20° C. and 250 revolutions per minute (rpm) and incubated for 30 minutes. IPTG (1 M solution) was added to the culture to yield a final concentration of 0.5 mM and the culture incubated for another 12-16 hours in the shaker incubator (20° C. and 250 rpm). A 50 aliquot was then removed from the fermentation tube, centrifuged (10,000×g for 2 minutes) and the cell pellet designated induced cell pellet. Un-induced and induced cell pellets were re-suspended in 50 µL of B-PER bacterial protein extraction reagent supplemented with DNAse and lysozyme, according to the manufacturer's instructions (Thermo Scientific, Waltham, Mass., USA). The cell suspensions were incubated for 1 hour at room temperature. The cell lysate from the induced culture was centrifuged at 20,000×g for 2 minutes. The supernatant was transferred to a new tube and designated induced cell lysate (S on gels). The remaining pellet was designated induced cell pellet (P on gels). The un-induced total cell lysate was designated UI on the gels. These samples were analyzed by SDS-PAGE as described below to determine FGF-21 expression levels. The colony that yielded the highest level of soluble FGF-21 (wild type and/or mutant) expression was selected to produce the proteins of interest in this study.

Example 4: Expression of FGF-21 (Wild-Type) and FGF-21 Mutants

The colony yielding the highest level of FGF-21 mutant expression was selected based on the staining intensity of the FGF-21 band from the induced two milliliter cultures described in Example 3. Tubes containing culture media (3 mL of LB-broth with animal free soytone supplemented with 25 µg/mL kanamycin sulfate) were inoculated with a scraping from the glycerol stock corresponding to the highest producer. The cultures grew overnight (12-16 hours) at 37° C. and 250 rpm. These starter cultures (1 mL) were used to inoculate 1 L of LB-broth containing 25 µg/mL kanamycin sulfate. The flask was incubated (37° C. at 250 rpm) until the $OD_{600}$ of the fermentation culture had reached 0.6-0.8. At this time, the flask was transferred to another shaker incubator set at 20° C. and 250 rpm and incubated for 45 to 60 minutes. The $OD_{600}$ was then measured and 500 μL of 1M IPTG solution was added to each flask and the fermentation continued at 20° C. and 250 rpm for 12-16 hours. Just prior to harvesting, the $OD_{600}$ of each flask was taken. The flasks were then transferred to 1 L centrifuge bottles and the cells were pelleted in a Sorvall RC-3B-PLUS by spinning at 4,657×g for 30 minutes and 4° C. The supernatant was carefully decanted into bleach and discarded. The cells were resuspended in 30 to 50 mL of distilled water and transferred into pre-weighed 50 mL conical centrifuge tubes. The cells were pelleted by centrifugation at 3220×g for 15 minutes and 4° C., the supernatants removed (decant) and the individual wet cell pellets were weighed and frozen at −80° C.

The expression of all FGF-21 wild-type and mutants resulted in sufficient yields between 11 and 70 mg per liter of fermentate based on the isolated yields calculated after purification and formulation (FIG. 2).

Example 5: Lysis and Purification FGF-21 (Wild-Type) and FGF-21 Mutants

FGF-21 and the FGF-21 mutants were purified using a combination of IEX chromatography (Source 15Q), affinity chromatography (Blue sepharose) and filtration through a Mustang Q membrane (process 1). An alternative purification strategy was also developed in which the FGF-21 mutant was re-purified using Source 15Q chromatography until the *E. coli* protease was removed (process 2). Using the later process, two IEX purification steps usually removed all of the residual protease; however, also three or four IEX chromatography steps may be performed if necessary.

Both processes removed any remaining protease and provided products that were greater than 98% pure.

5.1 Process 1
5.1.1 IEX Chromatography

The cell pellet (5 grams) from Example 4 is thawed and 20 mL of buffer (50 mM Tris, pH 7.5) is added. The pellet is resuspended by rotating end over end. The cell suspension is then passed through an Avestin emulsifier (Ottawa, ON, Canada) three times at a pressure of 25,000 psi to lyse the cells and the suspension centrifuged (14,502×g) for 25 min. The supernatant is removed by decanting and filtered through a 0.2 μm filter (TPP 150 mL vacuum Filtersystem) and the filtrate (conductivity ≤5 μS) loaded directly onto an ion exchange column (Source 15Q; 1.0 cm×30 cm; 24 mL) equilibrated with buffer (50 mM Tris-HCl, pH 7.5). The column was washed with 3 column volumes loading buffer and the FGF-21 eluted using a linear gradient of buffer (50 mM Tris-HCl, pH 7.5, 0 to 200 mM sodium chloride) over 20 column volumes at a flow rate of 2.0 mL/min. The eluted product is either frozen immediately and stored at −80° C. to prevent proteolysis or immediately processed through the next chromatography step.

5.1.2 Cibacron Blue Chromatography

The FGF-21 containing fractions are combined and diluted ten fold with buffer (50 mM HEPES pH 7.4) and immediately loaded onto a TosoGel Blue column (2 cm×12 cm; 25 mL). The column is then washed with ~100 mL (until baseline was obtained) of buffer to remove unbound material at a flow rate of 3.0 mL/min. The product was eluted using a step elution with buffer (50 mM HEPES, pH 7.4, 200 mM NaCl, 400 mM arginine) at 3 mL/min. The appropriate column fractions were then combined, buffer exchanged into a new buffer (20 mM HEPES, pH 6.8, 100 mM NaCl) and filtered through a Mustang Q membrane filter (Pall, Port Wash., N.Y., USA). The filtrate was then formulated and stored at −80° C. This process step removed protease for most of the FGF-21 proteins.

5.2 Process 2
5.2.1 IEX Chromatography—Step One

The cell pellet (5 grams) from Example 4 is thawed and 20 mL of buffer (50 mM Tris, pH 7.5) is added. The pellet is resuspended by rotating end over end. The cell suspension is then passed through an Avestin (Ottawa, ON, Canada) emulsifier three times at a pressure of 25,000 psi to lyse the cells and the suspension centrifuged (14,502×g) for 25 min. The supernatant is removed by decanting and filtered through a 0.2 μm filter (TPP 150 mL vacuum filter system) and the filtrate (conductivity <5 μS) loaded directly onto an ion exchange column (Source 15Q; 1.0 cm×30 cm; 24 mL) equilibrated with buffer (50 mM Tris-HCl, pH 7.5). The column was washed with 3 column volumes loading buffer and the FGF-21 eluted using a linear gradient of buffer (50 mM Tris-HCl, pH 7.5, 0 to 200 mM sodium chloride) over 20 column volumes at a flow rate of 2.0 mL/min. The eluted product is either frozen immediately and stored at −80° C. to prevent proteolysis or immediately processed through the next chromatography step.

5.2.2 IEX Chromatograph—Step Two

The FGF-21 containing fractions are combined and diluted four fold with buffer (50 mM HEPES pH 7.5) and immediately loaded onto an IEX column (Source 15Q; 1.0×30 cm; 25 mL) equilibrated with buffer (50 mM Tris-HCl, pH 7.5). The column was washed with 3 column volumes loading buffer and the FGF-21 eluted using a linear gradient of buffer (50 mM Tris-HCl, pH 7.5, 0 to 200 mM sodium chloride) over 20 column volumes at a flow rate of 2.0 mL/min. The fractions containing the eluted product are frozen immediately and stored at −80° C. to prevent proteolysis, if any remains. The protease assay is then performed using small samples from each column fraction to determine if protease remains. If protease is still present, the product is purified again using another IEX chromatography step (Source 15Q), as described above. The column fractions were then combined and formulated.

5.3 Large Scale Production

FIGS. 3, 4 and 5 illustrate production and purification of the inventive mutant FGF-21 peptide conjugates in large scale. FIG. 3 summarizes fermentation, cell harvest and obtaining of inclusion bodies. FIG. 4 illustrates the solubilization of inclusion bodies and the purification steps which may beneficially be used for purifying mutant FGF-21 peptides. The shown method of purification comprising two anion exchange chromatography steps was identified among many other purification protocols such as using DAE and SP Sepharose resins to give highest yields and most optimal purity of mutant FGF-21 peptides from large scale expression. FIG. 5 illustrates the glycoPEGylation procedure and subsequent purification protocol comprising two anion exchange chromatography steps which resulted in highest yields and most optimal purity of mutant FGF-21 peptide conjugates.

Example 6: Removal of Protease, Formulation of unPEGylated FGF-21s and Further Characterization All of the FGF-21s produced using this *E. coli* expression system were rapidly degraded by endogenous proteases upon storage at 4° C. using buffers from the purification process or formulation buffers. Therefore, during processing all of the partially purified samples were either processed immediately, or the intermediate fractions were stored frozen (−80° C.) until further processing was possible. Proteolysis can also be inhibited by the addition of high concentrations of arginine (≥400 mM) to the buffers.

All purified FGF-21s were tested for protease removal (stability) by incubating at 30° C. for three days. For FGF-21 mutants that still contained protease after the initial purification, either purification approach, a second, third or fourth IEX chromatography step (Source 15Q) was used to remove the remaining protease. Complete protease removal from all FGF-21 samples was essential since the GlycoPEGylation reaction requires incubation at 30° C. overnight. Inhibition of proteolysis during the GlycoPEGylation process is not possible using high salt concentrations (e.g. arginine, sodium chloride, etc.) as these conditions inhibit the GlycoPEGylation reaction.

Protease removal was determined by incubating the sample or column fraction (10-50 µL) that contained FGF-21 and potential protease at 30° C. for 1-3 days. Protease was deemed completely removed if no proteolysis of the FGF-21 had occurred after 3 days. SDS-PAGE was used to determine the extent of proteolysis. Complete protease removal was observed after purification of the IEX fractions using Cibacron Blue chromatography.

Figure 6:
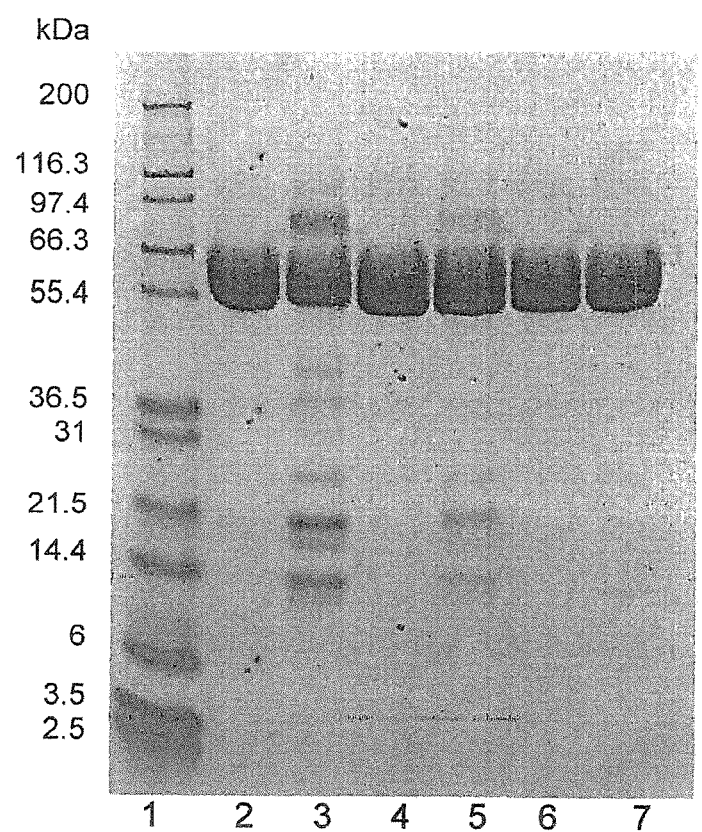
FIG. 6: Non-Reducing SDS-PAGE of 20 kDa PEG-FGF-21 (P(172)TQGAS) mutant conjugate samples stored at (2-8) ° C. and 40° C. for one week. Lane 1: Molecular Weight Marker, Lane 2: pH 5 Sample Stored at (2-8) ° C., Lane 3: pH 5 Sample Stored at 40° C., Lane 4: pH 6 Sample Stored at (2-8) ° C., Lane 5: pH 6 Sample Stored at 40° C., Lane 6: pH 7 Sample Stored at (2-8) ° C., Lane 7: pH 7 Sample Stored at 40° C. Sample compositions were as follows.

For SDS PAGE analysis, either 12% or 4-12% Bis-Tris NuPAGE pre-poured polyacrylamide gradient slab gels were used. Samples were mixed 1:1 with LDS Sample Buffer containing 0.1 M DTT, and heated at 95° C. for 3 min, unless otherwise noted. Gels were run at a constant voltage of 200 V for 40 min in MES buffer. After electrophoresis, the proteins were stained with Simply Blue safe stain (Life Technologies, Carlsbad, Calif., USA) solution for 2-24 hours while shaking at 50 rpm, at room temperature as necessary to visualize the proteins as described by the manufacturer. The standard proteins included masses of 188, 98, 62, 49, 38, 28, 17, 14, and 6 kDa (Invitrogen, Carlsbad, Calif., USA, SeeBlue® Plus-2 standards, Cat # LC5925) or 220, 150, 120, 100, 90, 80, 70, 60, 50, 40, 30, 25, 20, 15 and 10 kDa (Invitrogen, Carlsbad, Calif., USA, Novex® Sharp Prestained Protein standards). After destaining the gel with water, the protein bands were visualized and scanned on a Li-Cor Odyssey® Infrared Imager and recorded (LI-COR Inc., Lincoln, Nebr., USA). (FIG. 6)

Each FGF-21 (wild-type) and mutants (unPEGylated) was formulated in buffer (HEPES, 20 mM, pH 6.8; NaCl, 100 mM) to about 1 mg protein per mL and stored frozen (−80° C.). Endotoxin removal and sterile filtration were performed using an endotoxin removal filter disc unit (Mustang E, 0.2 micron filter). Vials were sealed and stored at −80° C. All samples were tested and released with tests that included ID (SDS PAGE), protein concentration (BCA), aggregation (SEC) and endotoxin.

In detail, the FGF-21s, collected after IEX chromatography were pooled, protein concentration determined (BCA) and concentrated using a spin filter (Pall, N.Y., USA, Macrosep® Advance Centrifugal Devices; 3K MWCO or Amicon Ultracel-3K spin filter) and centrifuging at 3220×g for about 45 minutes, or until the retentate protein concentration reached to 1-2 mg/mL. Formulation buffer for unmodified FGF-21 proteins was 20 mM HEPES, pH 6.8, 100 mM NaCl. Formulation buffer was then added to the retentate and the sample centrifuged as above until the retentate protein concentration was 1-2 mg/mL. This process was repeated two additional times. Formulation buffer was then added to the retentate to bring the protein concentration to about 1 mg/mL.

The formulation of all of the FGF-21 proteins was performed in a Labconco cabinet maintaining a sterile environment. The 0.2 µm Acrodisc® Mustang®-E syringe filter (PALL Corporation, NY, USA) was pretreated as per manufacturer's suggestions using 1 mL of sterile, endotoxin free water by filtering at 1-4 mL/min flow rate by hand at a controlled rate. The solutions were then filtered through the Mustang® E cartridges using a syringe at a flow rate of 1-4 mL/min. The filtrate was gently mixed and then aliquoted into 1.2 mL pyrogen-free cryovials into desired volumes. All products were stored frozen at −80° C.

Endotoxin contamination was determined using Limulus Amebocyte Lysate (LAL) assay (Genscript, Piscataway, N.J., USA, ToxinSensor™ Chromogenic LAL Endotoxin Assay Kit; Cat no. L00350). The LAL reaction is a quantitative in vitro endpoint assay which uses a modified LAL and a synthetic color producing substrate to detect endotoxin in a chromogenic assay. The concentration of endotoxin in a sample was calculated from its absorbance by comparison to the absorbance (405 nm) of solutions containing known amounts of endotoxin standard.

Protein concentration was determined using the Pierce Micro BCA™ Protein Assay Reagent Kit, part #23235 (ThermoFisher Scientific, Waltham, Mass., USA). BSA was used to prepare the standard curve. After incubating at 37° C. for 30 min, the plate was read on a microplate reader at 562 nm. Sample protein concentration is calculated by referring to the BSA standard curve. PEGylated proteins do not interfere with this assay.

The Tosoh Biosciences (Tokyo, Japan) column (TSK Gel G3000SW XL, 7.8 mm×30 cm, Cat # S7165-06R), size exclusion chromatography (SEC), was used to determine protein purity and the amount of aggregates. The column was equilibrated with running buffer (50 mM sodium phosphate, pH 6.8) and between 20-50 µL of sample (15-40 of protein) was injected. The method used a flow rate of 0.5 mL/min and absorbance at A280 was monitored.

All FGF-21 proteins were compared to the Bio-Rad protein reference standard mixture (Bio-RAD, Cat #151-19010) that contains bovine thyroglobulin (670,000), bovine γ-globulin (158,000), chicken ovalbumin (44,000), horse myoglobin (17,000), vitamin B12 (1,350). The reference standard was injected (~25 µL) either as a neat solution or a diluted solution with running buffer.

Example 7: Production of Mutant FGF21-GalNAc-SA-PEG-20/30 kDa

Glycosylation of each mutant was evaluated using an enzyme reaction composed of MBP-GalNAcT2 and UDP-GalNAc and GalNAc addition monitored by MALDI mass spectrometry.

The GlycoPEGylation of mutant FGF-21s was performed in a single step, one pot reaction using MBP-GalNAcT2, ST6GalNAc1, UDP-GalNAc and CMP-SA-PEG-20/30 kDa (either with 20 kDa PEG or with 30 kDa PEG). The purified FGF-21 mutants were buffered exchanged into reaction buffer (20 mM Bis-Tris, 50 mM NaCl, pH 6.7) using a Microsep® Advance Centrifugal Device (Pall, N.Y., USA, Concentrator, Cat # MAP003C37, 20 mL, 3K MWCO). After buffer exchange and concentration, the FGF-21 mutant protein concentration was between 3-5 mg/mL (BCA). CMP-SA-PEG-20/30 kDa (3 mol equiv) was dissolved into the solution of FGF-21 mutant (1 mole eq.). MBP-GalNAcT2 (14-15 mU/mg FGF-21), UDP-GalNAc (1.1 mol eq.), ST6GalNAc1 (100 mU/mg FGF-21) and $MnCl_2$ solution (10 mM final concentration) were added directly to the reaction tube and mixed gently. The final FGF-21 protein concentration should be between 2-4 mg/mL of reaction mixture. The reaction mixture was then incubated at 32° C. overnight (~16 hours). See also PCT Publication Nos: WO 2003/031464; WO 2005/089102; WO 2006/050247; and WO 2012/016984, the entire content of each of which is incorporated herein by reference.

The FGF-21-mutant-GalNAc-SA-PEG-20/30 kDa product was purified using IEX chromatography (Source 15Q; 1 cm×24 cm column) and the product eluted with a sodium chloride gradient [50 mM Tris buffer (pH 7.5), 0 to 100 mM sodium chloride gradient over 20 column volumes] at a flow rate of 2 mL/min. Fractions were analyzed by SDS-PAGE (4-12%), pooled, concentrated and formulated. All products were analyzed for content (BCA), purity (SDS-PAGE), aggregation (SEC) and endotoxin.

Conversion yields for this process were between 25 to 90% as determined by SDS PAGE. The PEGylation reaction mixtures were purified using IEX chromatography (Source 15 Q). Each PEGylated product was formulated and release tests performed. Release tests included ID (SDS PAGE), protein concentration (BCA), aggregation (SEC) and endotoxin. Each PEGylated product was greater than 98% pure with no detectable aggregates. The overall isolated yields were 15-44% (mono-PEG) based on starting FGF21 protein.

All of the GlycoPEGylated FGF-21 mutants were formulated by buffer exchanging the samples using spin filters, and then adjusting the formulation buffer volume to provide the desired protein concentration of about 1.0 mg/mL. During concentration, the protein concentration was never allowed to exceed 5 mg/mL to prevent protein aggregation. The formulation buffer used in this study was sodium phosphate (50 mM, pH 7.0), 100 mM NaCl. Endotoxin removal (Mustan E) and sterile filtration were performed using an endotoxin removal filter disc unit (0.2 micron filter). Vials were sealed and stored at −80° C. It was observed that Mustang® E filters significantly reduce overall isolated yields of product by binding FGF21.

Example 8: Micro Flow Imaging for Analysis of Subvisible Particles

To evaluate the effect of four excipients (sucrose, polysorbate 20, EDTA, and L-methionine) on the mutant FGF-21 conjugate quality attributes after repetitive freeze-thaw and shaking stress, conjugate samples were concentrated from approximately 1.0 mg/mL to 36 mg/mL by ultrafiltration (UF), and diluted to 25 mg/mL. Eleven formulations of TEV-47948 were prepared (Table 1), filled with 1.6 mL fill volume into 2 cc glass vials, and frozen at −20° C. All formulations were subjected to four cycles of stress: thawing at room temperature: shaking at 500 rpm for 6 hours at room temperature, and freezing at −20° C. After thawing, formulations were analyzed by micro-flow imaging (MFI) counting ≥2 µm, ≥5 µm, ≥10 µm, and ≥25 µm sub-visible particles. Sub-visible particles were measured using MFI5200 system from ProteinSimple (San Jose, Calif.) equipped with a 100 µm flow cell. Samples in 0.9 mL aliquots were loaded on a 96 well plate and transferred into an autosampler BotI. Illumination optimization was performed prior to each sample. The TEV-47948 samples were analyzed in duplicates with 0.2 mL purge volume, 0.6 mL imaged volume, 0.17 ml/min flor rate, and standard 5× magnification. Prior to analysis samples were homogenized in a well by atomatic mixing with a pipette tip. The image filter implemented in the MFI View System Software (MVSS) was used to separate images of air bubbles from proteinaceous particles.

TABLE 1

Composition of mutant FGF-21 peptide conjugate formulations

| Formulation | Mutant FGF-21 peptide Conjugate mg/mL | Tris/Tris-HCl, mM | NaCl, mM | Sucrose mM | PS20 mg/mL | Na2H2 EDTA-2H2O, mg/mL | L-Met, mg/mL |
|---|---|---|---|---|---|---|---|
| F1 | 26 | 16 | 56 | 0 | 0 | 0 | 0 |
| F2 | 26 | 16 | 56 | 0 | 0 | 0.25 | 1.5 |
| F3 | 26 | 16 | 56 | 0 | 0.3 | 0 | 1.5 |
| F4 | 26 | 16 | 56 | 0 | 0.3 | 0.25 | 1.5 |
| F5 | 26 | 16 | 56 | 0.075 | 0.15 | 0.125 | 0.75 |
| F6 | 26 | 16 | 56 | 0.075 | 0.15 | 0.125 | 0.75 |
| F7 | 26 | 16 | 56 | 0.075 | 0.15 | 0.125 | 0.75 |
| F8 | 26 | 16 | 56 | 0.15 | 0 | 0 | 1.5 |
| F9 | 26 | 16 | 56 | 0.15 | 0 | 0.25 | 0 |
| F10 | 26 | 16 | 56 | 0.15 | 0.3 | 0 | 0 |
| F11 | 26 | 16 | 56 | 0.15 | 0.3 | 0.25 | 1.5 |

MFI results show substantially more sub-visible particles in formulations without polysorbate 20 (F1, F2, F8, F9), i.e. polysorbate 20 reduces the concentration of sub-visible particles (FIG. 7). As a result, the following formulation composition of mutant FGF-21 peptide conjugate drug product is recommended to minimize sub-visible particles by MFI: 26 mg/mL mutant FGF-21 peptide conjugate, 16 mM Tris, 56 mM NaCl, 0.15 M sucrose, and 0.2 mg/mL polysorbate 20; pH 7.5.

Example 9: Testing of FGF-21 Mutants and glycoPEGylated Conjugates In Vitro

The FGF-21 mutants and glycoPEGylated FGF-21 conjugates were screened in a cell-based assay that measured glucose uptake in mouse adipocytes. Increased glucose uptake in mouse adipocytes via increased glucose transporter expression is a reported function of FGF-21 (Kharitonenkov et al., 2005, *Journal of Clin Invest*, 115(6):1627-1635). In this assay, the potency of a test compound is expressed as an $EC_{50}$ value, which is the concentration of the mutant or conjugate that gave a half maximal response. Test samples with a lower EC50 are more active.

For this purpose, mouse 3T3-L1 pre-adipocytes were differentiated for 21 days in 96-well plates in preparation for testing as similarly described (Kharitonenkov et al., 2005, *Journal of Clin Invest*, 115(6):1627-1635). Serial dilutions of the FGF-21 mutants and glycoPEGylated conjugates were prepared and added to the adipocytes for a 72 hr incubation. During the last 4 hours of the incubation, cells were changed into media containing reduced glucose concentration and then labeled with [$^3$H]-2-deoxyglucose (Perkin Elmer, Waltham, Mass., USA) for 1 hr. Cells were washed to stop uptake and to remove unincorporated glucose. Adipocytes were lysed with 0.1 N NaOH and scintillation cocktail (Ultima Gold™, Perkin Elmer, Waltham, Mass., USA). Nonspecific uptake of [$^3$H]-2-deoxyglucose was determined in the presence of 50 µM cytochalasin. Plates were read on a Microbeta® LSC counter (Perkin Elmer, Waltham, Mass., USA).

The potency of non-glycoPEGylated FGF-21 mutants is summarized in Table 2 and was evaluated to determine whether the mutations alone affected FGF-21 activity. Potency values ranged from 0.4-4.3 nM, as compared to the potency of 2.0 nM for wild type FGF-21. These data demonstrate that mutating the FGF-21 sequence at certain locations in order to create the glycosylation consensus site was well tolerated. A value of about 30 nM or higher would have been considered inactive.

TABLE 2

Potency evaluation of FGF-21 mutants by glucose uptake in mouse adipocytes. The position of the proline residue in the FGF-21 amino acid sequence according to SEQ ID NO: 1 is given in brackets.

| Mutated Sequence | Glucose uptake in differentiated mouse adipocytes $EC_{50}$ values (nM) Non-glycoPEGylated[1] |
|---|---|
| P(148)TP | 1.4 |
| P(172)TQGAS | 0.7 |
| P(156)TP | 2.2 |
| M(1)FPTP | 3.0 |
| P(5)TSSP | 3.4 |
| P(5)TQAP | 4.3 |
| P(151)TINT | 2.0 |
| P(151)TTVS | 2.4 |
| P(125)TQA | 0.4 |
| P(125)TEI | 0.8 |
| P(3)TP | 0.7 |
| Wild Type | 2.0 |

[1]Screened in a single assay.

The potency of the glycoPEGylated FGF-21 mutant conjugates ranged from 9 nM to 20 nM (Table 3). The most potent glycoPEGylated analogs ($EC_{50}$~10 nM) demonstrated less potency than the wild type FGF21 (2 nM), likely reflecting some hindrance caused by incorporation of the bulky PEG moiety. A range of attachment sites (from near the N-terminus to proline 172) suggests that addition of the glycoPEG to either end of the molecule was tolerated well. This data is consistent with a report showing that an alternative approach to PEGylation at the N-terminus was also tolerated, as evidenced by increased glucose uptake in mouse adipocytes (Huang et al., 2011, *PLoS One*, 6(6): e20669). However, the observation that attachment of the glycoPEG moiety to residues near the C-terminal region was also tolerated was not expected. Several reports have demonstrated that the C-terminal end of FGF-21 is required for binding to β-Klotho, and deletion of C-terminal amino acid residues is not well tolerated for binding and potency (Yie et al., 2008, *FEBS Letters*, 583:19-24; Goetz et al., 2012, *Molecular and Cellular Biol*, 32(10): 1944-54).

TABLE 3

Potency evaluation of glycoPEGylated FGF-21 conjugates PEGylated with 30 kDa PEG by glucose uptake in mouse adipocytes. The position of the proline residue in the FGF-21 amino acid sequence according to SEQ ID NO: 1 is given in brackets.

| Mutant sequence motif | Glucose uptake in differentiated mouse adipocytes $EC_{50}$ values (nM) GlycoPEGylated[1] |
|---|---|
| P(148)TP | 9 |
| P(172)TQGAS | 10 |
| P(156)TP | 10 |
| M(1)FPTP | 10 |
| P(159)TINT | 20 |

[1]Data represent the average of between 2 and 5 independent assays.

Initially, only 30 kDa PEGylated mutant conjugates were tested as it was expected that those would be the most promising candidates for further development. However, as explained herein above and below, the mutant conjugates with 20 kDa PEG exhibited surprising properties based on available experimental data.

Example 10: Testing of 20 kDa Versus 30 kDa glycoPEGylated FGF-21 Mutant Conjugates in Mouse Glucose Uptake Assay and Human Cell Extracellular Signal-Regulated Kinases (ERK) Phosphorylation Assay Selected FGF-21 mutants were prepared with either a 20 kDa or a 30 kDa PEG moiety and tested for potency in mouse and human cell lines (Table 4). Mouse 3T3-L1 adipocytes were used to evaluate potency in a glucose uptake assay as described in Example 9.

In order to evaluate mutant conjugate activity in a human cell line, human embryonic kidney (HEK-293) cells were transiently transfected with human β-Klotho, the co-receptor for FGF-21. Receptor activation was evaluated using an assay to detect phosphorylation of extracellular signal-related kinase (ERK). Cells were plated in 96 well plates, incubated overnight, and serial dilutions of the FGF-21 mutant conjugates applied for 20 minutes. Cells were lysed and measured by ELISA for phospho-ERK (R&D Systems catalog no. DYC1018B; R&D Systems, Inc., Minneapolis, Minn., USA). Resulting fluorescence was read on a Flexstation® Microplate reader (Molecular Devices, Sunnyvale, Calif., USA).

Surprisingly, the conjugates comprising a 20 kDa PEG moiety were more active than the 30 kDa PEG conjugates.

Additionally, it was observed that the two assays used were differentially sensitive to modifications. The conjugate P(5)TSSP which is glycoPEGylated near the N-terminus showed acceptable activity in the human phospho-ERK assay while showing a good activity in the mouse glucose uptake assay. However, conjugates modified near the C-terminus maintained very high potency in both human and mouse cell lines (cf. data of P(156)TP and P(172)TQGAS in Table 3).

TABLE 4

Comparison of FGF-21 mutant conjugates comprising either 20 kDa or 30 kDa PEG moieties. The position of the proline residue in the FGF-21 amino acid sequence according to native FGF-21 sequence according to SEQ ID NO: 1 is given in brackets.

| Mutant sequence motif | Glucose uptake in differentiated mouse adipocytes $EC_{50}$ values (nM) PEG Size (kDa) | | ERK phosphorylation in HEK-293 cells expressing[1] β-Klotho $EC_{50}$ values (nM) PEG Size (kDa) | |
|---|---|---|---|---|
| | 20 | 30 | 20 | 30 |
| P(5)TSSP | 33 | 71 | 293 | >3000 |
| P(156)TP | 38 | 38 | 109 | 188 |
| P(172)TQGAS | 47 | 54 | 86 | 177 |

[1]HEK-293 cells transiently expressed β-Klotho co-receptor for FGF-21.

Example 11: In Vivo Testing of Conjugates of Example 10 with 20 kDa and 30 kDa PEG Moieties The conjugates of Example 10, each with a 20 kDa or a 30 kDa PEG moiety, were chosen for a more detailed investigation in vivo (results are given in Table 4). The selected conjugates had good activity in the in vitro cell assays and were expressed in suitable quantities for in vivo testing.

Pharmacokinetic (PK) half-life extension and exposure in normal Sprague Dawley rats and efficacy in the db/db diabetic mouse model were used as criteria to identify the most potent conjugates.

For determining PK half-life extension in Sprague Dawley rats, FGF-21 conjugates were diluted in sterile phosphate buffered saline and administered subcutaneously to male Sprague Dawley (~0.3 kg) rats at 0.25 mg/kg. Blood was drawn at 1, 2, 4, 6, 24, 30, 48, 54, 72, 78, and 96 hours after administration from the lateral tail vein. Blood samples were held at room temperature for 20 minutes and then centrifuged to separate serum. The serum fraction was transferred into clean tubes, frozen on dry ice, and stored at −80° C. pending analysis. FGF-21 conjugates were detected in serum by ELISA according to manufacturer's directions (BioVendor, Brno, Czech Republic, human FGF-21 ELISA, cat # RD191108200R), except that each conjugate was used to prepare the standard curve. Composite pharmacokinetic parameters were estimated by non-compartmental analysis of the serum concentration versus time data using WinNonlin software (Professional Version 5.2, Pharsight Corporation, Palo Alto, Calif., USA).

The circulating half-life of the glycoPEGylated conjugates was extended (range 15-30 hours) when compared to wild-type FGF-21 (2 hours). Both 20 kDa and 30 kDa PEGylation had a similar impact on conjugate half-life and exposure demonstrating the value of PEGylation for half-life extension of FGF-21.

TABLE 5

Efficacy of glycoPEGylated FGF-21 conjugates in vivo. The position of the proline residue in the FGF-21 amino acid sequence according to SEQ ID NO: 1 is given in brackets.

| Conjugate- | In vivo PK[1] | | In vivo efficacy range (mg/kg)[2] | | |
|---|---|---|---|---|---|
| PEG size | Half-life (hours) | AUC (mg * h/mL) | Blood Glucose | Triglycerides | Insulin |
| P(172) TQGAS-20 | 22 ± 3 | 35 ± 1 | 0.125-2.5 | 0.125-0.25 | 2.5 |
| P(172) TQGAS-30 | 21 ± 2 | 42 ± 5 | 0.125-5 | 5 | >5[4] |
| P(156)TP-20 | 15 ± 1 | 25 ± 1 | 0.25-2.5 | 0.125-2.5 | >2.5 |
| P(156)TP-30 | 18 ± 1 | 30 ± 4 | 0.125-4 | 1 | 2.5-4 |
| P(5)TSSP-20 | 24 ± 0.4 | 24 ± 1 | 2.5 | 1 | >2.5 |
| P(5)TSSP-30 | 30 ± 1 | 17 ± 1 | 4 | >4 | >4 |
| FGF-21 WT | 2 ± 0.2 | 0.3 ± 0.01 | 3[3] | >3 | >3 |

PK = pharmacokinetic, WT = wild type, AUC = area under the curve.
[1]Sprague Dawley rats were dosed subcutaneously with 0.25 mg/kg of each conjugate or wild-type FGF-21.
2Range of doses that showed significant improvement for each parameter. Conjugates were dosed on days 1 and 4, with data collected on day 6.
[3]FGF-21 was dosed daily at 3 mg/kg for 14 days.
[4]Data was trending but did not reach significance by ANOVA.

The db/db diabetic mouse is a genetic model with a mutation in the leptin receptor which results in high blood glucose and dyslipidemia. The determination of pharmacodynamic effects in the db/db mouse model was performed at HD Biosciences (Shanghai, China). Male db/db mice (BKS.Cg-Dock7m+/+Lep/$^{db}$/J) and age-matched littermates (non-diabetic control) were purchased from Model Animal Research Center of Nanjing University, China. Animals were acclimatized for one week after the arrival under a standard condition with room temperature at 21-23° C., 30-70% relative humidity, and a 12 h:12 h light:dark cycle. Diet and water were available ad libitum. All experimental procedures were approved by the institutional animal care and use committee (IACUC) at HD Biosciences. For conjugate screening, mice were dosed at 0, 0.125, 0.25, 1, 2.5 mg/kg on days 1 and 4. Blood glucose was determined during the study using a glucometer. On day 6, animals were sacrificed, and serum triglycerides (EnzyChrom™ assay, cat#ETGA-200, Bioassay Systems, Hayward, Calif., USA) and insulin levels (Mouse Insulin Kit, MesoScale Discovery, Rockville, Md., USA) were evaluated.

GlycoPEGylated conjugates were examined in db/db mice for effects on blood glucose, serum triglycerides and insulin levels (Table 5). Doses that significantly improved these parameters are shown in Table 5. While both 20 kDa and 30 kDa glycoPEGylated conjugates were similarly efficacious at reducing blood glucose levels, the 20 kDa PEGylated conjugates generally outperformed the 30 kDa conjugates by improving triglycerides at lower doses and across broader dose ranges.

Table 6 below demonstrates that the 20 kDa conjugate of each mutant decreased triglyceride levels to a greater extent than did the 30 kDa conjugate when each data set was compared to its vehicle control group the value of which is considered to be 100% (hence, the lower the results, the better the performance).

TABLE 6

Decrease in Triglycerides (% of Vehicle Control). 0.125 mg/kg dose administered on days 1 and 4, triglycerides determined on day 6.

| | 20 kDa PEG | 30 kDa PEG |
|---|---|---|
| P(172) TQGAS | 69 ± 16 | 72 ± 35 |
| P(156) TP | 66 ± 20 | 117 ± 37 |
| P(5) TSSP | 86 ± 33 | 96 ± 15 |

Serum insulin levels were altered across a broad range by administration of glycoPEGylated FGF-21 conjugates (Table 7). It was anticipated that as insulin resistance was ameliorated by FGF-21 conjugates, serum hyperinsulinemia would be resolved. All db/db mice showed significant hyperinsulinemia as compared to nondiabetic littermate controls. Administration of P(172)-20 resulted in the greatest reduction of insulin, with a 73% decrease at 2.5 mg/kg. Furthermore, P(172)-20 demonstrated a trend towards decreased serum insulin at 0.25-1.0 mg/kg doses.

TABLE 7

Reduction in serum insulin levels for glycoPEGylated conjugates in the db/db mouse model.

| | Serum insulin levels (ng/mL) for 20 kDa PEG-FGF-21 conjugates | | |
|---|---|---|---|
| Dose (mg/kg) | P(172)-20 | P(156)-20 | P(5)TSSP-20 |
| Non-diabetic | 0.4 ± 0.1*** | 0.4 ± 0.1* | 0.4 ± 0.1** |
| db/db + vehicle | 5.6 ± 1.0 | 3.6 ± 0.5 | 3.6 ± 0.5 |
| 0.125 | 6.0 ± 0.6 | 9.3 ± 1.1*** | 3.5 ± 0.5 |
| 0.25 | 3.9 ± 0.7 | 4.8 ± 0.8 | 4.5 ± 0.4 |
| 1 | 3.8 ± 0.6 | 3.7 ± 0.7 | 6.1 ± 0.7* |
| 2.5 | 1.5 ± 0.1*** | 3.1 ± 0.7 | 5.6 ± 0.7 |

*$p < 0.05$, $p < 0.01$, *$p < 0.001$ as determined by one-way ANOVA

In summary, all mutants and mutant conjugates were expressed in suitable amounts and are biologically active. 20 kDa-PEG conjugates showed better performance in in vitro glucose uptake and ERK phosphorylation assays and in in vivo experiments while half-life was similarly improved in 20 kDa-PEG and 30 kDa PEG mutant conjugate species. Hence, since apparently no further increase in half-life is achieved when attaching a larger 30 kDa PEG residue in contrast to a smaller 20 kDa PEG residue to a mutant FGF-21, it is beneficial to attach the smaller 20 kDa PEG as smaller PEG residues are less likely to create hindrance of receptor binding or shielding of parts of the FGF-21 mutant protein, which are required for natural biological interaction, (which would lead to a reduced biological activity) is expected to occur. Moreover, 20 kDa PEGylated conjugates generally outperformed the 30 kDa conjugates by improving triglycerides at lower doses and across broader dose ranges.

Example 12: Efficacy of Administration of Multiple Doses of 20 kDa PEG-FGF-21 P(172)TQGAS (in this Example 12 Referred to as "Mutant FGF-21 Peptide Conjugate") to Diabetic Cynomolgus Monkeys Cynomolgus monkeys (age range 6-28 years old) were randomized into groups (n=6) at the beginning of the experiment based on their endogenous FGF21 levels. The average serum level of FGF-21 between groups ranged from 229±58 pg/mL to 312±88 pg/mL. After an acclimatization phase and a 2-week baseline collecting phase, monkey groups were dosed with vehicle, 0.1 mg/kg, 0.3 mg/kg or 1 mg/kg mutant FGF-21 peptide conjugate, s.c., once per week over a course of 8 weeks. Monkeys were evaluated for an additional 10 weeks during the washout phase of the study. Study endpoints included body weight, food consumption, fasted blood glucose, HbA1c level, ALT, and serum lipids.

12.1 Effect of Mutant FGF-21 Peptide Conjugate on Body Weight and Food Intake

Diabetic cynomolgus monkeys demonstrated reduced food intake at all dose levels (Table 8). However, only animals treated with the highest dose of the mutant FGF-21 peptide conjugate (1.0 mg/kg) displayed a significant reduction in percentage body weight, with the maximal effect of approximately 10% at the end of the treatment phase (Table 8). The effects did not plateau before the treatment ended, and animals regained their body weights to the baseline levels around 4 weeks after the last treatment (data not shown).

TABLE 8

Effect of mutant FGF-21 peptide conjugate on body weight and food intake in diabetic Cynomolgus monkeys

| Parameter | Day on Test | Vehicle | FGF-21 mutant conjugate (mg/kg) s.c. | | |
|---|---|---|---|---|---|
| | | | 0.1 | 0.3 | 1.0 |
| Body Weight (kg) Mean (SEM) | 0 56 % Change from Baseline | 8.2 (1.3) 8.1 (1.3) −1.2% | 9.4 (0.7) 9.3 (0.8) −1.1% | 10.1 (1.7) 9.8 (1.7) −3.0% | 8.0 (0.8) 7.2 (0.8) −10.0%$^a$ |
| Food Intake (g) Mean (SEM) | 0 56 % Change from Baseline | 185 (22) 188 (20) 1.8% | 214 (24) 160 (28) −25.4%$^a$ | 201 (22) 141 (15) −29.7%$^a$ | 223 (25) 126 (36) −43.7%$^a$ |

$^a$p < 0.05; kg = kilogram; SEM = standard error of the mean 12.2 Effect of the Mutant FGF-21 Peptide Conjugate on Glycemic Control in Diabetic Cynomolgus Monkeys The efficacy of the mutant FGF-21 peptide conjugate was evaluated on several parameters of glycemic control including fasting blood glucose, glycosylated hemoglobin A1c (HbA1c), serum insulin levels, and tolerance in an oral glucose tolerance test (OGTT). Previous reports have suggested that FGF-21 analogs may not impact glycemic control in NHP or humans (Talakdar et al., 2016, Gaich et al., 2014). Administration of the short acting FGF-21 analog LY2405319 to obese type 2 diabetics demonstrated reduced body weight, insulin, and triglycerides but did not significantly reduce blood glucose (Gaich et al., 2014). Similarly, the long acting FGF-21 analog PF-05231023 reduced body weight and triglycerides but showed no effect on glucose tolerance in obese cynomolgus monkeys (Talakdar et al., 2016). No change was observed in fasting glucose and insulin levels in type 2 diabetic patients (Talakdar et al., 2016). Researchers assessed the efficacy of a 12 week trial of BMS-986036 (Bristol-Myers Squibb) in 120 patients with type 2 diabetes. Patients who received BMS-986036 showed improved N-terminal type III collagen propeptide but did not show improvements in HbA1c or body weight (Charles E D, et al. Abstract 33. Presented at: The Liver Meeting; Nov. 11-15, 2016; Boston; Charles E D, et al. Abstract 1082. Presented at: The Liver Meeting; Nov. 11-15, 2016; Boston).

Once weekly administration of the tested mutant FGF-21 peptide conjugate to diabetic monkeys improved fasting blood glucose levels in a dose dependent manner (Table 9). Insulin levels were variable among groups at the outset of the study, but significant decreases as compared to baseline were observed at the highest dose (Table 9).

Consistent with the change in fasting blood glucose was the concomitant improvement in HbA1c levels (FIG. 8), which is a reliable index for evaluating blood glucose levels over time. It is noteworthy that improved HbA1c has not been reported for any other FGF-21 analog or mutant in the art to date. In particular, improved HbA1c has not been reported for product candidates based on FGF-21, namely BMS-986036 of BMS or PF-05231023 of Pfizer or LY2405319 of Lilly.

TABLE 9

Effect of the mutant FGF-21 peptide conjugate on Fast Blood Glucose in Diabetic Cynomolgus Monkeys

| Parameter | Day on Test | Vehicle | FGF-21 mutant conjugate (mg/kg) s.c. | | |
|---|---|---|---|---|---|
| | | | 0.1 | 0.3 | 1.0 |
| Blood Glucose (mg/dL) Mean (SEM) | 0 56 % Change from Baseline | 210 (42) 246 (46) 16.7%$^a$ | 201 (37) 141 (30) −29.9%$^a$ | 197 (37) 120 (19) −39.4%$^a$ | 250 (18) 115 (16) −53.9%$^b$ |
| Serum Insulin (mIU/L) Mean (SEM) | 0 56 % Change from Baseline | 78 (33) 66 (18) −16% | 124 (76) 55 (27) −56% | 137 (64) 53 (18) −61% | 51 (10) 15 (3) −72%$^a$ |

$^a$p < 0.05, $^b$p < 0.01; kg = kilogram; mIU = milli-international units; SEM = standard error of the mean Blood samples (1.0 mL/per time) were collected from the cephalic or saphenous vein into BD Vacutainer® K2-EDTA tubes at time points indicated. The samples were stored immediately in a refrigerator at 4° C. or wet ice. Samples were analyzed at the same day when blood was collected.

HbA1c was measured with HPLC by using the Glycated hemoglobin test system (BIO-RAD, Hercules, Calif., USA).

The OGTT was performed on day −11 (baseline), and on days 31 and 52 post-dosing (FIG. 9). The mutant FGF-21 peptide conjugate improved oral glucose tolerance on both days 31 and 52 and at all doses tested. It appears that the maximal effect of the mutant FGF-21 peptide conjugate on glucose tolerance was surprisingly reached by day 31 and at the lowest dose, as differences in glucose tolerance within each treatment group on day 31 and 52 were similar. Divergent effects of FGF21 analogs on OGTT in NHP have been observed and may reflect variations in the pharmacology of FGF21 analogs. Improvements in OGTT were not observed for a long acting FGF21 in obese cynomolgus (Talakdar et al., 2016) but were reported for a long acting FGF21 analog in obese rhesus monkey (Murielle M. Véniant, Renee Komorowski, Ping Chen, Shanaka Stanislaus, Katherine Winters, Todd Hager, Lei Zhou, Russell Wada, Randy Hecht, and Jing Xu (2012) Endocrinology 153:4192-4203).

Glucose was administered to animals by placing 1.0 g/kg glucose+10 g/kg banana: glucose was buried in the middle of banana and then fed to animals. Blood was obtained via tail vein puncture for blood glucose measurement by glucometer (ACCU-CHEK® Performa, Roche). Data are shown as the area under the curve (AUC) for each treatment. *p<0.05, **p<0.01 (FIG. 9).

12.3 Serum ALT Levels in Diabetic Cynomolgus Monkeys Treated with the Mutant FGF-21 Peptide Conjugate Serum ALT levels were measured weekly during the course of the study. ALT levels were reduced in the 0.3 mg/kg and 1.0 mg/kg dose groups on day 7 and 14, respectively. A trend of reduced ALT levels were observed out to day 14 for the 0.3 mg/kg dose group (p=0.056) and out to day 28 in the 1.0 mg/kg group (p=0.073). In contrast, ALT concentration rose modestly in the vehicle group by the end of the treatment period (FIG. 10).

Serum chemistry parameters (TG, TC, HDL, LDL, ALT, glucose) were measured by using the ADVIA® R2400 (SIEMENS) system.

12.4 Serum Lipid Concentrations in Diabetic Cynomolgus Monkeys Treated with the Mutant FGF-21 Peptide Conjugate Serum lipid levels (triglyceride (TG), total cholesterol (TC), high density cholesterol (HDL) and low density cholesterol (LDL) were measured weekly during the course of the study. Treating animals with the mutant FGF-21 peptide conjugate for 4 days led to a dramatic decrease in serum TG levels at all doses tested which remained stabilized for the duration of the treatment phase. Serum TG levels recovered during the washout phase to their baseline levels (FIG. 11). By contrast, only an insignificant increase in TG levels was observed in the animals treat with vehicle.

TG levels were normalized to baseline values for each individual (FIG. 11). Serum chemistry parameters (TG, TC, HDL, LDL, ALT, glucose) were measured by using the ADVIA® R2400 (SIEMENS) system.

Total cholesterol levels and LDL cholesterol were modestly lowered by 29 and 39 percent, respectively, at the highest dose of the mutant FGF-21 peptide conjugate. HDL cholesterol levels were significantly elevated with the mutant FGF-21 peptide treatment and returned to baseline during the washout phase (FIG. 12).

Serum chemistry parameters (TC, HDL, LDL) were measured by using the ADVIA R4200® (SIEMENS) system. HDL cholesterol levels were normalized to baseline values for each individual.

12.5 Adiponectin Biomarker Evaluation in Diabetic Cynomolgus Monkeys Treated with the Mutant Peptide FGF-21 Peptide Conjugate High molecular weight (HMW) Adiponectin levels elevations trended in the 0.1 mg/kg and 0.3 mg/kg groups and were significantly elevated 1.0 mg/kg doses by day 21 (FIG. 13).

Adiponectin in monkey serum was detected using a commercial kit for Human HMW Adiponectin/Acrp30 Immunoassay, Catalog No. DHWADO (R&D Systems).

Example 13: Efficacy of Administration of 20 kDa PEG-FGF-21 P(172)TQGAS (in this Example 13 Referred to as "TEV-47948") in a Mouse Model of Nonalcoholic Steatohepatitis (NASH)

13.1 Efficacy in a Mouse Model of Nonalcoholic Steatohepatitis (NASH)

The Stelic Animal Model (STAM) mouse develops NASH, fibrosis and finally hepatocellular carcinoma. This model demonstrates pathological progression that is very similar to the human disease; in particular, STAM mice manifest NASH at 8 weeks, which progresses to fibrosis at 12 weeks, and finally develop hepatocellular carcinoma (Saito et al., 2015). The mutant FGF-21 peptide conjugate was evaluated in STAM mice and its effect on body weight, liver to body weight ratio, liver steatosis, inflammation, fibrosis, and the composite NAFLD Activity Score (NAS) was evaluated.

NASH was induced in 40 C57BL/6 male mice by a single subcutaneous injection of 200 μg streptozotocin (STZ, Sigma-Aldrich, USA) 2 days after birth and feeding with high fat diet (HFD, 57 kcal % fat, cat#: HFD32, CLEA Japan, Japan) after 4 weeks of age. The mice were randomized into 5 groups of 8 mice at 6 weeks of age. Phosphate buffered saline (PBS) was used as the vehicle. Eight male mice, fed with normal diet and without STZ treatment, were used for the Normal group. The mutant FGF-21 peptide conjugate was administered once every 72 hours, s.c., from 6-9 weeks of age at doses of 0.1, 0.5, 2.0 and 6.0 mg/kg.

The mutant FGF-21 peptide conjugate significantly improved liver weight and liver to body weight ratio over the course of the study (Table 10). Mean body weight, liver weight and the liver-to-body weight ratio on the day of sacrifice significantly decreased in the mutant FGF-21 peptide conjugate-0.5 mg/kg, -2.0 mg/kg and -6.0 mg/kg groups compared with the vehicle group.

TABLE 10

Body and Liver Weights in the STAM Model afer Mutant FGF-21 Peptide Conjugate Treatment. Data shown are the average ± standard deviation for each group (n = 8 animals per group) at the end of the study.

| Parameter | Normal | Vehicle | mutant FGF-21 peptide dose (mg/kg) | | | |
| --- | --- | --- | --- | --- | --- | --- |
| | | | 0.1 | 0.5 | 2.0 | 6.0 |
| Body Weight (g) | 22.6 ± 0.9 | 20.3 ± 0.9 | 19.0 ± 1.7 | 17.5 ± 1.9[1] | 15.8 ± 0.9[1] | 14.5 ± 1.2[1] |
| Liver weight (mg) | 1013 ± 95 | 1310 ± 179 | 992 ± 193[1] | 892 ± 151[1] | 753 ± 182[1] | 632 ± 109[1] |

TABLE 10-continued

Body and Liver Weights in the STAM Model afer Mutant FGF-21 Peptide
Conjugate Treatment. Data shown are the average ± standard deviation for each group
(n = 8 animals per group) at the end of the study.

| Parameter | Normal | Vehicle | mutant FGF-21 peptide dose (mg/kg) | | | |
|---|---|---|---|---|---|---|
| | | | 0.1 | 0.5 | 2.0 | 6.0 |
| Liver-to-body (%) | 4.5 ± 0.5 | 6.5 ± 1.0 | 5.3 ± 1.4 | 5.1 ± 0.7[2] | 4.8 ± 1.0[3] | 4.4 ± 0.5[1] |

[1] = $p < 0.001$ as compared to vehicle group;
[2] = $p < 0.05$ as compared to vehicle group;
[3] = $p < 0.01$ as compated to vehicle group.

The mutant FGF-21 peptide conjugate improved biochemistry parameters in the STAM model (Table 11). On Days 7 and 16, non-fasting blood glucose levels significantly increased in the Vehicle group compared with the Normal group. On Day 16, non-fasting blood glucose levels significantly decreased in the mutant FGF-21 peptide conjugate-6.0 mg/kg group compared with the Vehicle group. On day 22, fasting blood glucose levels significantly decreased in the mutant FGF-21 peptide conjugate –6.0 mg/kg group and tended to decrease in the mutant FGF-21 peptide conjugate –0.1 mg/kg and –2.0 mg/kg groups compared with the Vehicle group. There was no significant difference in 4-hour fasting blood glucose levels between the Vehicle group and the mutant FGF-21 peptide conjugate –0.5 mg/kg group.

Serum Alanine Transaminase (ALT) levels serve as a marker of liver damage and were significantly increased in the Vehicle group compared with the Normal group in the STAM model. Serum ALT levels significantly decreased in the mutant FGF-21 peptide conjugate-2.0 mg/kg and -6.0 mg/kg groups and tended to decrease in the mutant FGF-21 peptide conjugate-0.5 mg/kg group compared with the Vehicle group. There was no significant difference in serum ALT levels between the Vehicle group and the mutant FGF-21 peptide conjugate-0.1 mg/kg group.

The NAFLD Activity Score (NAS) is a measure of steatosis (oil red O staining), ballooning of apoptotic hepatocytes (HE staining), and inflammation (F4/80 immunostaining) and was developed as a tool to measure changes in NAFLD during therapeutic trials. Liver sections from the Vehicle group in the current study exhibited severe micro- and macro-vesicular fat deposition, hepatocellular ballooning and inflammatory cell infiltration. Consistent with these observations, NAS significantly increased in the Vehicle group compared with the Normal group. All doses of the TEV-47948 group showed marked improvements in steatosis, hepatocellular ballooning and inflammatory cell infiltration, with a significant reduction in NAS compared with the Vehicle group (FIG. 14).

13.2. Efficacy in the DIN (Diet Induced NASH) Mouse Model of Nonalcoholic Steatohepatitis (NASH)

In an alternative animal model, the DIN model induces NASH using changes to diet as understood in the art and described below. The DIN Nash model is an accepted animal model of type II diabetes. It, therefore, differs from that of the STAM NASH model described above in which NASH was induced in mice by a injection of streptozotocin, followed by a high fat diet (STAM NASH). STAM NASH is an accepted animal of type I diabetes.

In the DIN model described in this example, the acclimation phase comprises a standard diet (RM1 (E) 801492, SDS) and normal drinking water, which were provided ad libitum. Mice were then fed a 60% high fat/2% cholesterol diet (Research Diets Inc., NJ, USA) and 10% fructose in drinking water (DIN diet). The fat content of the diet is 60%

TABLE 11

Biochemical Parameters in the STAM Model after Mutant FGF-21 Peptide
Conjugate Treatment. Data shown are the average ± standard deviation for each group
(n = 8 animals per group) at the end of the study.

| Parameter | Normal | Vehicle | mutant FGF- 21 peptide conjugate dose (mg/kg) | | | |
|---|---|---|---|---|---|---|
| | | | 0.1 | 0.5 | 2.0 | 6.0 |
| Blood glucose (Day 7, mg/dL) | 164 ± 25 | 346 ± 124[2] | 265 ± 76 | 351 ± 127 | 334 ± 119 | 274 ± 133 |
| Blood glucose (Day16,mg/dL) | 165 ± 26 | 376 ± 107[2] | 371 ± 82 | 388 ± 139 | 342 ± 164 | 220 ± 113[1] |
| Fasted Blood glucose (Day 22, mg/dL) | 193 ± 19 | 409 ± 722 | 274 ± 90 | 333 ± 157 | 284 ± 172 | 204 ± 692 |
| ALT (U/L) | 20 ± 2 | 225 ± 193[2] | 153 ± 160 | 85 ± 60 | 56 ± 43[1] | 58 ± 45[1] |
| AST (U/L) | 68 ± 26 | 295 ± 149[2] | 252 ± 166 | 238 ± 101 | 225 ± 84 | 239 ± 58 |
| Liver Triglyceride (mg/g liver) | 15.8 ± 8.9 | 25.8 ± 9.9 | 15.1 ± 8.0 | 12.6 ± 7.3[1] | 12.9 ± 14.4[1] | 8.3 ± 4.1[2] |

ALT = serum alanine transaminase.
AST = asparatate aminotransferase.
[1] = $p < 0.05$ as compared to vehicle group;
[2] = $p < 0.01$ as compared to vehicle group.

kcal from fat. On a % g basis, fat represents 35% g with 3% g from soybean oil and 32% g from lard Methods:

After the acclimation period, mice were fed DIN diet for 25 weeks. Mice body weight was measured weekly until the end of the 25-week diet period. At 6 weeks of diet period, mice were weighed and 4-hour fasted (10% fructose replaced by normal water) at 09:00 AM. Blood was then collected at 1:00 PM to measure blood glucose and plasma insulin, as well as plasma ALT and AST levels. HOMA-IR was calculated from blood glucose and plasma insulin values. 15 mice with the lowest HOMA-IR and ALT/AST values were excluded. Mice were divided into 5 homogenous groups according to their HOMA-IR, ALT/AST and body weight and treated with vehicle or 3 different doses of TEV-47498 injections s.c every 3 days. The OCA was given in the diet.

At 6, 10, 15, and 19 weeks of treatment, mice were 4-hour fasted (10% fructose replaced by normal water) at 9:00 AM and blood was collected to measure glycaemia, plasma insulin, ALT and AST, total cholesterol and triglycerides levels. At week 19 of treatment, all mice were bled (~100 µL blood) at 4 different time points (0, 6, 24, 48 h) after the last dose to isolate serum that was stored at −80° C. prior to shipment in dry ice for analysis. 5 mice per group were bled at 0 h and 24 h and the other 5 were bled at 6 h and 48 h post dosing. After the last blood collection, mice were sacrificed by cervical dislocation under 4% isoflurane anesthesia and exsanguinated with sterile saline.

Results:

In this study, the effect TE-47948 was evaluated in the DIN mouse model as described herein above, with the following particulars. After 6 weeks of a diet inducing NASH, a subgroup of C57B16 mice were treated with TE-47948 at three different doses (20 µg/kg, 100 µg/kg, and 500 µg/kg) via sub-cutaneous administration, every 3 days for 19 weeks. To compare the efficiency of TE-47948 on NASH progression to relative controls, a subgroup of C57B16 mice induced to have NASH was treated with vehicle control and a subgroup of C57B16 mice induced to have NASH was treated with the FXR agonist obeticholic acid (OCA), which was admixed into the diet (25 mg/kg), and these subgroups were assessed in parallel. OCA was used as a reference for its anti-NASH properties.

TEV-47948 significantly reduced liver damage induced in the DIN mouse model in a dose dependent manner. This observation was evidenced by a significant reduction of the histological NAS score, as well as a strong reduction of hepatic transaminases, liver lipids and inflammatory and fibrotic markers. See, for example, FIGS. 15 and 16.

In addition to the beneficial effects on the liver, TE-47948 revealed also significant anti-diabetic and anti-obesogenic properties. See, for example, FIGS. 17-20. Taken together, these observations confirmed the beneficial effects of TE-47948 in the treatment of diet-induced NASH.

Example 14: Different Treatment Regimens and Effect Thereof on Efficacy of Administration of 20 kDa PEG-FGF-21 P(172)TQGAS (in this Example 14 Referred to as "Glycol-PEG-FGF-21") to Diabetic Cynomolgus Monkeys The objective of this example is to investigate the pharmacological effects of glyco-PEG-FGF21 and its systemic exposure in spontaneous diabetic cynomolgus monkeys when administered using different treatment regimens. More particularly, the experiments are directed to examining the pharmacological effects of glyco-PEG-FGF21 when administered once a week or once every 2 weeks by subcutaneous injection.

Experimental Design 14.1. Animal Housing

Spontaneous diabetic monkeys are housed and maintained in accordance with the guidelines approved by the Association for Assessment and Accreditation of Laboratory Animal Care (AAALAC). The targeted conditions for animal living environment and photoperiod are as follows:

Temperature: 23±3° C.
Humidity: 50±20%
Light cycle: 12 hours light and 12 hours dark 14.2. Monkey Dietary All animals have free access to water and are fed twice daily with a complete nutritionally balanced diet enriched with seasonal fruits.

Diet Composition (%)

| Carbohydrate | ~51.8% |
| Crude Protein | ≥16.0 |
| Crude Fat | ≥4.0 |
| Moisture | ≤10.0 |
| Ash | ≤7.0 |
| Fiber | ≤4.0 |
| Calcium | 0.8~1.2 |
| Phosphorus | 0.6~0.8 |

14.3. Compound, Formulation, and Supplies

The formulated compound comprises 25 mg/mL glyco-PEG-FGF21 in 20 mM Tris HCL, 70 mM sodium chloride, pH 7.5.

14.4. Grouping, Experimental Procedure and Treatment 14.4.1. Grouping

Thirty spontaneous diabetic cynomolgus monkeys will be screened to select 24 diabetic monkey subjects that fit the study inclusion criteria. Serum from at least thirty (30) animals will be collected and several parameters, such as glucose, insulin, lipids, liver enzymes, etc. will be measured. Selected animals (n=24) will be enrolled into the study and evenly distributed among the experimental groups with respect to their body weight, glucose, lipids, and insulin levels.

The selected diabetic animals for the study will be treated with either the vehicle or with the test article as described in Table 12.

TABLE 12

Group design, dose, frequency, and route of administration

| Group | N | Treatment | Dose Level (mg/kg) | Conc. (mg/mL) | Dose Volume (mL/kg) | Route of Administration | Dosing Days |
|---|---|---|---|---|---|---|---|
| 1 | 6 | Vehicle (PBS) | 0 | | 0.2 | S.C. | 0, 7, 14, 21, 28 |
| 2 | 6 | glyco-PEG-FGF21 | 1 | 5 | 0.2 | S.C. | 0, 7, 14, 21, 28 |
| 3 | 6 | glyco-PEG-FGF21 | 1 | 5 | 0.2 | S.C. | 0, 14, 28 |
| 4 | 6 | glyco-PEG-FGF21 | 2 | 10 | 0.2 | S.C. | 0, 14, 28 |

14.4.2. Experimental Procedures and Treatment Regimen with Glycol-PEG-FGF-21

A flowchart of the experimental design and data collection for Example 14 is shown in FIG. 21.

The study comprises two phases: a pre-treatment phase and a treatment phase. The effects will be observed after subcutaneous (sc) administration of either the vehicle or the glyco-PEG-FGF21 formulated compound. The time course of observation, data collection and treatment are shown in FIG. 21 and also summarized in Table 13.

Pre-Treatment—

All of the experimental animals will have 1 week to acclimate followed by 2 weeks for collecting baseline data of oral glucose tolerance test (GTT), biochemistry (triglycerides, HDL, LDL, ALT, Glucose) body weight (BW), FGF-21 and food intake. The animals will be fasted overnight for BW measurement and blood sample collection for lipid measurement and blood glucose. Oral glucose-banana GTT (1.0 g/kg glucose+10 g/kg banana: glucose buried in the middle of banana and then fed to animals) (0, 15, 30, 60, 120, 180 min) will be conducted day 0 as baseline.

Treatment—

Animals will be treated by sc administration with the vehicle (PBS) or glyco-PEG-FGF21 according to Table 12. Animals will be fasted overnight before the treatment. After the 1st and last (day 28) sc dosing, a series of blood samples will be collected for pharmacokinetics (PK) at pre-dose, 6, 24, 48, 72, 120, and 168 hours post dose. On day 14, all animals will be bled for PK prior to the next dosing. Blood for PK bioanalysis (2 ml/per time) will be drawn into a suitable tube from a saphenous or cephalic vein which is inserted with a butterfly needle for pharmacodynamic (PD) assay. All samples will be permitted to clot briefly at room temperature and then centrifuged at 4° C. at 3500 rpm for 10 minutes. The serum will be transferred into pre-labeled polypropylene screw-cap vials and immediately stored in a freezer at −80° C. until analyzed. Food consumption will be conducted weekly; Oral glucose-banana GTT will be conducted at week 4.

Washout—

During the 2-week washout, BW, food intake will be conducted weekly and blood collection for biochemistry and PK (day 42, 43 and 44) will be collected at the end of the washout period. Oral glucose-banana GTT will be conducted at week 6.

Clinical observation, such as animal activity, behavior, appetite and diarrhea, will be followed during the study. Any abnormal changes will be recorded and reported.

14.5. Blood Sampling and Serum Harvesting

TABLE 13

Time points and blood volumes for PK/PD Study

| Study Week | Study Day | Dosing | PD* | HbA1c | PK | Oral glucose-banana GTT |
|---|---|---|---|---|---|---|
| −2 | −14 | | 2.5 | 1.0 | | |
| −1 | −7 | | 2.5 | | | One blood drop × 5 |
| 0 | 0 | x | 2.5 | 1 0 | 2.0 × time points | |
| 1 | 7 | x** | 2.5 | | | |
| 2 | 14 | x | 2.5 | 1.0 | 2.0 × 1 time point | |
| 3 | 21 | x** | 2.5 | | | |
| 4 | 28 | x | 2.5 | 1.0 | 2.0 × time points | One blood drop × 5 |
| 5 | 35 | | 2.5 | | | |
| 6 | 42 | | 2.5 | 1.0 | 2.0 × time points | One blood drop × 5 |

*insulin, triglycerides, TC, HDL, LDL, ALT, glucose, adiponectin
**only to group 1 and 2
Oral glucose-banana GTT: Blood glucose will be measured by glucometer via tail vein puncture without blood collection following the time points: 0', 15', 30', 60', 120', 180'.

14.5.1. Samples for PK and Adiponectin Assay

Blood samples (2 mL/per time) will be collected from the cephalic or saphenous vein into BD Serum Separator Vacutainer® Tubes immediately before dosing and at a serial time points (pre-dose, 6, 24, 48, 72, 120, and 168 hours post dose). All samples will be permitted to clot for a minimum of 30 minutes at room temperature and then centrifuged in a refrigerated centrifuge (4° C.) at 3,500 rpm for 10 minutes. The serum will be transferred into pre-labeled polypropylene screw-cap vials and immediately stored in a freezer at −80° C. until analyzed as described herein above.

In this sample analysis study (Alliance Pharma), mouse anti-human FGF21, IgG1 monoclonal antibody (capture antibody) were coated onto a 96-well microplate. The analyte (TEV-47948) present in the standards, quality controls (QCs), and the tested animal serum test samples bound to the capture antibody on the plate. TEV-47948 further bound to mouse anti-PEG, IgM monoclonal antibody labeled with horseradish peroxidase (HRP) which catalyzed the chromogenic HRP substrate 3,3',5,5'-tetramethylbenzidine (TMB) yielding a blue color. The blue color then changed to yellow via the addition of stop solution containing sulfuric acid, resulting in maximum absorbance at 450 nm. The absorbance at 450 nm minus the background reading at 562 nm was proportional to the amount of TEV-47948 in the calibration standards, QC samples, and test samples.

14.5.2. Samples for PD and Adiponectin Assay

Blood samples (2.5 mL/per time) will be collected from the cephalic or saphenous vein into BD Serum Separator Vacutainer® Tubes following above Table 13. All samples will be permitted to clot for a minimum of 30 minutes at room temperature and then centrifuged in a refrigerated centrifuge (4° C.) at 3,500 rpm for 10 minutes. The serum will be transferred into pre-labeled polypropylene screw-cap vials and immediately stored in a freezer at −80° C. until analysis.

Serum chemistry parameters (triglycerides, HDL, LDL, ALT, Glucose) will be measured by using the ADVIA®R2400 (SIEMENS) system. Serum insulin will be measured with chemiluminescence by using the ADVIA Centaur®R XP Immunoassay System (SIEMENS).

For adiponectin, venous blood (1 mL/per time) will be collected into a serum collection tube from an appropriate vein of each animal. Blood will be centrifuged at 2400 g for 10 minutes under refrigerated conditions (set to maintain+4° C.). The resultant serum will be separated into 2 aliquots (1st aliquot of 200 μL; 2nd aliquot: remaining volume of approximately 100 μL to be noted), and will be kept on wet ice until transferred into individual tubes and stored at −80° C. The 2 aliquots will be kept at −80° C. until dispatch (with a temperature recorder) assayed.

In this sample analysis study (Alliance Pharma), HMW adiponectin in the assay calibration standards, matrix quality control (mQC) samples, and tested animal serum test samples bound to the mouse monoclonal antibody (MoAb) on the microplate and immobilized. After washing away any unbound substances, a horseradish peroxidase (HRP)-conjugated MoAb specific for UMW adiponectin was added to the wells to which the HMW adiponectin further bound. The HRP-conjugated MoAb catalyzed the chromogenic HRP substrate 3,3',5,5'-tetramethylbenzidine (TMB), yielding a blue color. The addition of a stop solution halted the HRP and TMB reaction and changed the color from blue to yellow with a maximum absorbance at 450 nm. The absorbance at 450 nm minus the background reading at 562 nm was proportional to the amount of HMW adiponectin in the calibration standards, mQC samples, and test samples.

14.5.2 Samples for HbA1c Assay

Blood samples (1.0 mL/per time) will be collected from the cephalic or saphenous vein into BD Vacutainer® K2-EDTA tubes following above Table 13. The samples will be transferred immediately into a refrigerator at 4° C. for storage or placed on wet ice and sent for same day analysis. HbA1c will be measured with HPLC by using a standard assay such as, e.g., the Glycated hemoglobin test system available from BIO-RAD.

14.5.3. Samples for Oral Glucose-Banana GTT Assay

One drop of blood will be obtained via tail vein puncture for blood glucose measurement by glucometer.

14.5.4. Samples for Endogenous FGF21

Samples will be collected for the potential analysis of endogenous FGF-21. Assays for measuring FGF-21 are commercially available may be performed using, e.g., the anti-FGF-21 kit sold by BioVendor LLC, NC, USA (Cat. No.: RD191108200R) according to the manufacturer's protocol.

All publications mentioned herein are hereby incorporated by reference in their entireties. While the foregoing invention has been described in some detail for purposes of clarity and understanding, it will be appreciated by one skilled in the art from a reading of the disclosure that various changes in form and detail can be made without departing from the true scope of the invention in the appended claims.

Specific examples of methods and kits have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The embodiments of the invention described above are intended to be exemplary only. Those skilled in this art will understand that various modifications of detail may be made to these embodiments, all of which come within the scope of the invention.

The invention claimed is:

1. A mutant Fibroblast Growth Factor-21 (FGF-21) peptide conjugate comprising
   i) a mutant FGF-21 peptide comprising the amino acid sequence of SEQ ID NO: 2,
   ii) a glycosyl moiety, and
   iii) a 20 kDa polyethylene glycol (PEG),
   wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; or a pharmaceutical composition comprising the mutant FGF-21 peptide conjugate and a pharmaceutically acceptable carrier.

2. The mutant FGF-21 peptide conjugate according to claim 1, wherein the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof.

3. The mutant FGF-21 peptide conjugate according to claim 1, wherein the glycosyl moiety comprises at least one of an N-acetylgalactosamine (GalNAc) residue, a galactose (Gal) residue, a sialic acid (Sia), or a combination thereof.

4. The mutant FGF-21 peptide conjugate according to claim 3, wherein the at least one Sia residue is a nine-carbon carboxylated sugar.

5. The mutant FGF-21 peptide conjugate according to claim 4, wherein the at least one Sia residue is N-acetylneuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxynonulosonic acid (KDN), or a 9-substituted sialic acid.

6. The mutant FGF-21 peptide conjugate according to claim 5, wherein the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac.

7. The mutant FGF-21 peptide conjugate according to claim 1, wherein the glycosyl moiety comprises the structure -GalNAc-Sia-.

8. The mutant FGF-21 peptide conjugate according to claim 1, wherein the 20 kDa PEG moiety is attached to the glycosyl moiety by a covalent bond to a linker, wherein the linker comprises at least one amino acid residue.

9. The mutant FGF-21 peptide conjugate according to claim 8, wherein the at least one amino acid residue is a glycine (Gly).

10. The mutant FGF-21 peptide conjugate according to claim 1 comprising the structure -GalNAc-Sia-Gly-PEG(20 kDa).

11. The mutant FGF-21 peptide conjugate according to claim 1, comprising the structure:

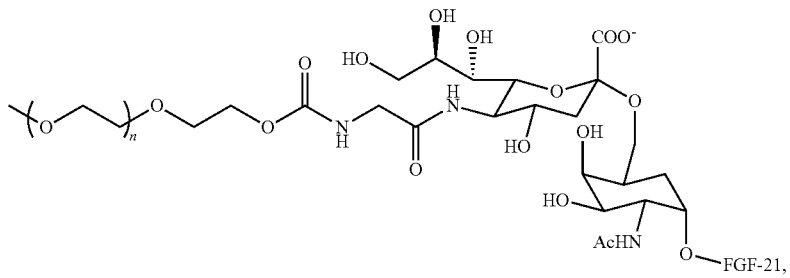

wherein n is an integer selected from 450 to 460.

12. The mutant FGF-21 peptide conjugate according to claim 1, wherein the 20 kDa PEG is a linear or branched PEG.

13. The mutant FGF-21 peptide conjugate according to claim 1, wherein the 20 kDa PEG is a 20 kDa methoxy-PEG.

14. A method of producing the mutant FGF-21 peptide conjugate according to claim 1, comprising the steps of:
    (1) recombinantly producing the mutant FGF-21 peptide in an expression host; and
    (2) enzymatically attaching to the mutant FGF-21 peptide of step (1) a PEG-glycosyl moiety, wherein the PEG has 20 kDa, thereby forming the mutant FGF-21 peptide conjugate.

15. A method for reducing blood glucose in a subject in need thereof, comprising administering to the subject in need thereof an amount of the mutant FGF-21 peptide conjugate according to claim 1 or the pharmaceutical composition according to claim 1.

16. The method of claim 15, wherein the subject in need thereof has a disease comprising at least one of diabetes type 2, non-alcoholic steatohepatitis (NASH), or metabolic syndrome.

17. The method according to claim 15, wherein the subject is a human subject.

18. The method according to claim 15, wherein the administering reduces HbA1C levels, wherein reducing HbA1C levels is indicative of a durable reduction in blood glucose levels over time.

19. The method of claim 15, wherein the mutant FGF-21 peptide conjugate is administered once a week or once every two weeks.

20. A method for reducing HbA1C in a subject in need thereof, comprising administering to the subject in need thereof an amount of the mutant FGF-21 peptide conjugate according to claim 1 or the pharmaceutical composition according to claim 1.

21. The method of claim 20, wherein the subject in need thereof has a disease comprising at least one of diabetes type 2, non-alcoholic steatohepatitis (NASH), or metabolic syndrome.

22. The method according to claim 20, wherein the subject is a human subject.

23. The method according to claim 20, wherein the administering reduces HbA1C levels, wherein reducing HbA1C levels is indicative of a durable reduction in blood glucose levels over time.

24. The method of claim 20, wherein the mutant FGF-21 peptide conjugate is administered once a week or once every two weeks.

25. A method for treating non-alcoholic steatohepatitis (NASH) or metabolic syndrome, comprising administering to a subject in need thereof an amount of the mutant FGF-21 peptide conjugate according to claim 1 or the pharmaceutical composition according to claim 1.

26. The method according to claim 25, wherein the subject is a human subject.

27. The method of claim 25, wherein the mutant FGF-21 peptide conjugate is administered once a week or once every two weeks.

* * * * *

UNITED STATES PATENT AND TRADEMARK OFFICE
CERTIFICATE OF CORRECTION

PATENT NO. : 10,407,479 B2
APPLICATION NO. : 16/225640
DATED : September 10, 2019
INVENTOR(S) : Karla K. Kopec and Patrick Mengyuan Liu Page 1 of 1

It is certified that error appears in the above-identified patent and that said Letters Patent is hereby corrected as shown below:

In the Claims

Column 100, Claim 11, replace:
"11. The mutant FGF-21 peptide conjugate according to claim 1, comprising the structure:

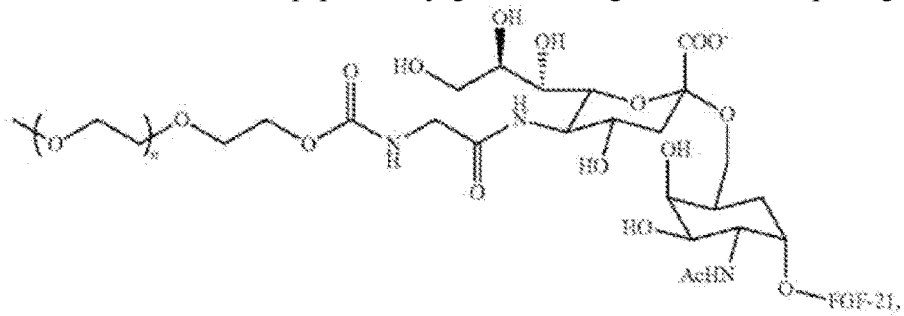

wherein n is an integer selected from 450 to 460"

With:
-- 11. The mutant FGF-21 peptide conjugate according to claim 1, comprising the structure:

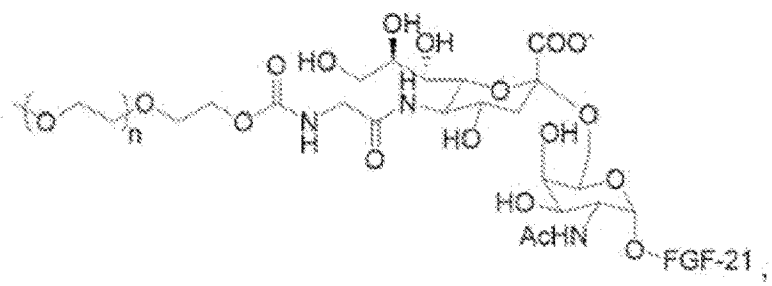

wherein n is an integer selected from 450 to 460 --.

Signed and Sealed this
Seventh Day of February, 2023

Katherine Kelly Vidal
*Director of the United States Patent and Trademark Office*